(12) United States Patent
Scott et al.

(10) Patent No.: US 8,342,042 B2
(45) Date of Patent: Jan. 1, 2013

(54) DEVICE FOR COLLECTING CHEMICAL COMPOUNDS AND RELATED METHODS

(75) Inventors: Jill R. Scott, Idaho Falls, ID (US); Gary S. Groenewold, Idaho Falls, ID (US); Catherine Rae, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 226 days.

(21) Appl. No.: 12/777,951

(22) Filed: May 11, 2010

(65) Prior Publication Data

US 2011/0277564 A1 Nov. 17, 2011

(51) Int. Cl.
*G01N 1/22* (2006.01)
(52) U.S. Cl. .................................................. 73/863.21
(58) Field of Classification Search .................. None
See application file for complete search history.

(56) References Cited

U.S. PATENT DOCUMENTS

| | | | |
|---|---|---|---|
| 3,438,179 A | 4/1969 | Jouault | |
| 3,748,905 A * | 7/1973 | Fletcher et al. | 73/863.25 |
| 3,925,022 A | 12/1975 | Showalter et al. | |
| 5,266,496 A | 11/1993 | Dacruz | |
| 5,286,651 A | 2/1994 | Smith | |
| 5,374,250 A | 12/1994 | Dixon | |
| 5,859,375 A | 1/1999 | Danylewych-May et al. | |
| 6,174,732 B1 | 1/2001 | Ong et al. | |
| 6,324,927 B1 | 12/2001 | Ornath et al. | |
| 6,405,608 B1 * | 6/2002 | Lindgren et al. | 73/863.21 |
| 6,408,701 B1 * | 6/2002 | Fujita | 73/864.71 |
| 6,619,143 B2 | 9/2003 | Danylewych-May et al. | |
| 6,817,227 B2 * | 11/2004 | Thompson et al. | 73/40.7 |
| 6,979,363 B2 * | 12/2005 | Boyd et al. | 96/413 |
| 7,121,157 B2 * | 10/2006 | Lean et al. | 73/864.71 |
| 7,140,265 B2 * | 11/2006 | McGill et al. | 73/863.21 |
| 7,384,457 B2 * | 6/2008 | Emmons et al. | 96/106 |
| 7,386,957 B2 | 6/2008 | Duffney | |
| 7,665,374 B2 * | 2/2010 | Akinbo et al. | 73/863.21 |
| 2002/0033058 A1 | 3/2002 | McGee et al. | |
| 2002/0150504 A1 | 10/2002 | Nunes et al. | |
| 2005/0032237 A1 | 2/2005 | Sandra et al. | |

OTHER PUBLICATIONS

Rodacy et al. "Underwater Chemical Sensing of Explosive Targets Using Ion Mobility Spectroscopy" Explosive Subsystems and Materials Department, Sandia National Laboratories, Albuquerque, New Mexico 87185-1452 and Coastal Systems Station, Dahlgren Division, Naval Surface Warfare Center, Panama City, Florida 32407-7001.

(Continued)

*Primary Examiner* — Robert R Raevis
(74) *Attorney, Agent, or Firm* — TraskBritt

(57) ABSTRACT

A device for sampling chemical compounds from fixed surfaces and related methods are disclosed. The device may include a vacuum source, a chamber and a sorbent material. The device may utilize vacuum extraction to volatilize the chemical compounds from the fixed surfaces so that they may be sorbed by the sorbent material. The sorbent material may then be analyzed using conventional thermal desorption/gas chromatography/mass spectrometry (TD/GC/MS) instrumentation to determine presence of the chemical compounds. The methods may include detecting release and presence of one or more chemical compounds and determining the efficacy of decontamination. The device may be useful in collection and analysis of a variety of chemical compounds, such as residual chemical warfare agents, chemical attribution signatures and toxic industrial chemicals.

26 Claims, 39 Drawing Sheets

OTHER PUBLICATIONS

Smith et al. "Detection of Gas-phase Chemical Warfare Agents Using Field-portable Gas Chromatography-mass Spectrometry Systems: Instrument and Sampling Strategy Considerations" Trends in Analytical Chemistry, vol. 23, No. 4, 2004.

Rodacy et al. "Underwater Chemical Sensing of Explosive Targets Using Ion Mobility Spectroscopy" Explosive Subsystems and Materials Department, Sandia National Laboratories, Albuquerque, New Mexico 87185-1452 and Coastal Systems Station, Dahlgren Division, Naval Surface Warfare Center, Panama City, Florida 32407-7001, IJIMS 5(2002)3, pp. 59-62.

Groenewold et al., "Recovery of phosphonate surface contaminants from glass using a simple vacuum extractor with a solid-phase microextraction fiber," Analytica Chimica Acta. vol. 697, Issues 1-2, p. 38-47; Jul. 4, 2011.

PCT International Search Report and Written Opinion of the International Searching Authority for PCT/US11/36126, dated Aug. 25, 2011, 10 pages.

* cited by examiner

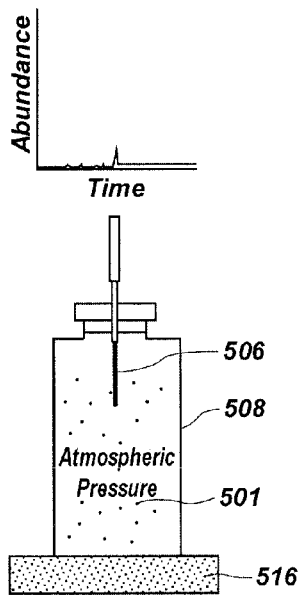 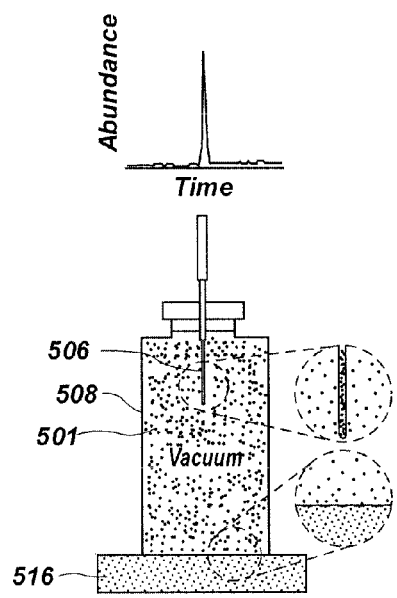
FIG. 5A          FIG. 5B
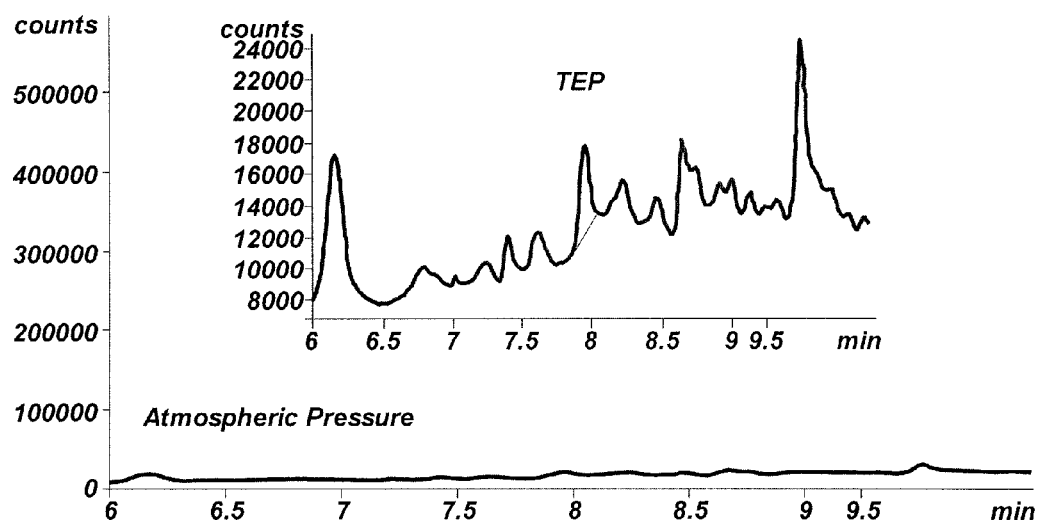
FIG. 6A

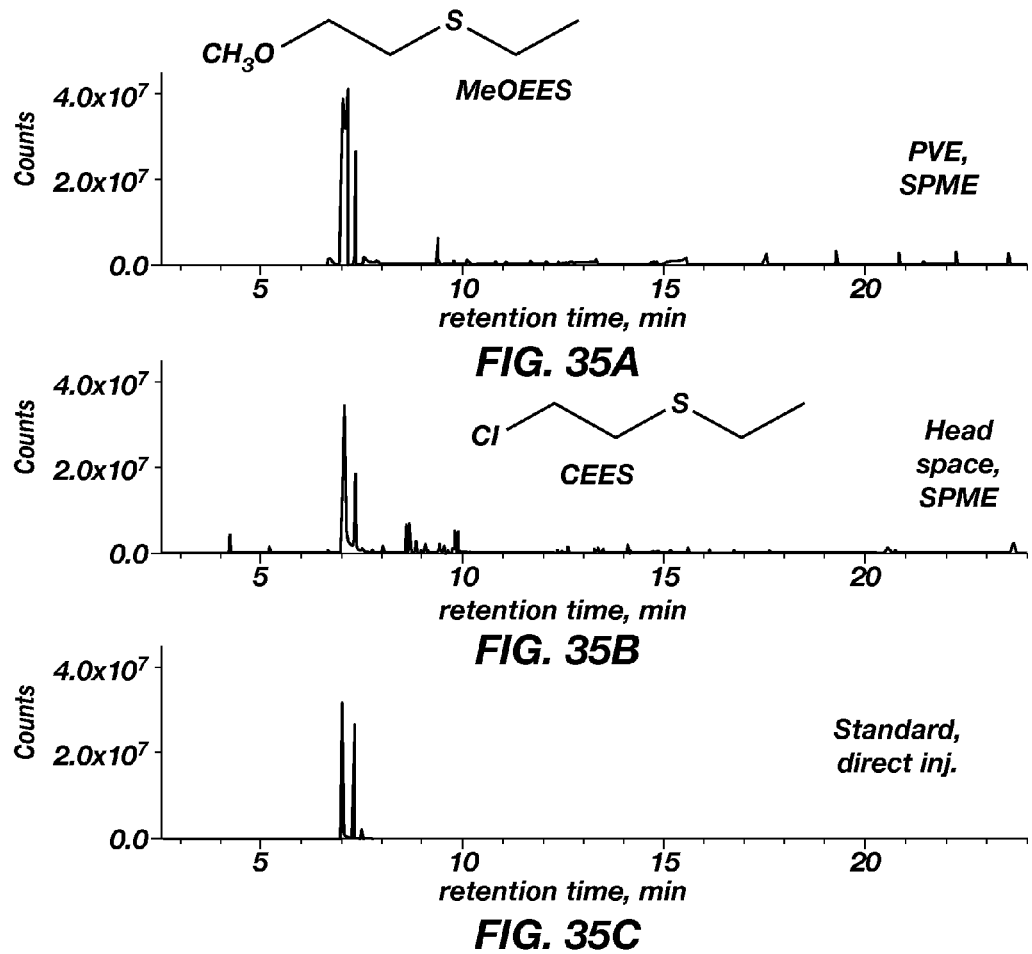
FIG. 35A
FIG. 35B
FIG. 35C
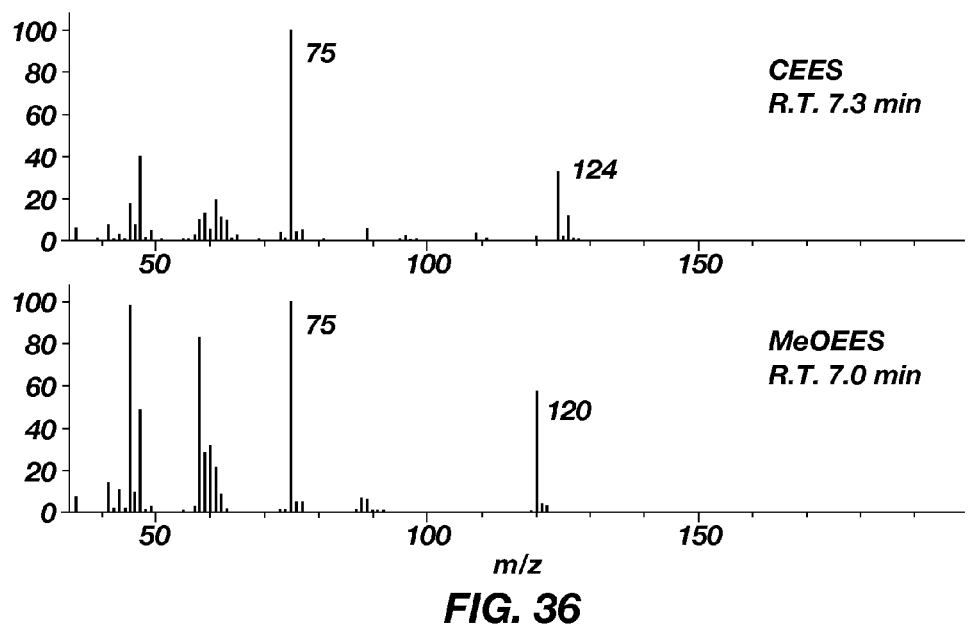
FIG. 36

RT, 5.1 min

RT, 6.5 min

RT, 7.8 min

DEVICE FOR COLLECTING CHEMICAL COMPOUNDS AND RELATED METHODS

GOVERNMENT RIGHTS

This invention was made with government support under Contract No. DE-AC07-05ID14517 awarded by the United States Department of Energy. The government has certain rights in the invention.

CROSS-REFERENCE TO RELATED APPLICATIONS

The present application is related to U.S. patent application Ser. No. 13/104,853, entitled "Devices for Collecting Chemical Compounds" filed on May 10, 2011, which is a continuation-in-part application of the present application.

TECHNICAL FIELD

The present invention relates to devices and methods for collecting chemical compounds. More specifically, embodiments of the present invention relate to a portable extraction device for collecting and transporting chemical compounds for analysis and related methods.

BACKGROUND

In a release of toxic chemicals into an urban or indoor environment, a wide range of compounds will be dispersed in addition to the principal toxin. These compounds, often referred to as "chemical attribution signature" (CAS) compounds, are derived from the synthesis and degradation of the toxin mixture, thus, they are highly indicative of the synthetic route, stabilization, storage, and methods of release. CAS compounds may have significant forensic value, provided they may be effectively collected at the event site.

For example, during the release of a chemical warfare agent (CWA) as an act of terrorism, there is a potential for a significant number of casualties from exposure to one or more toxins in the CWA. Such casualties may occur by inhalation or by dermal contact with aerosols or contaminated surfaces. In the aftermath of a CWA release, treatment of the victims, and decontamination and re-entry of the affected area will be high recovery priorities. Another activity of high priority will be fast and accurate identification of the perpetrators.

The identification of the CWA is the first and most important objective, since this dictates treatment of the victims and provides guidance for the amount of time an affected area will remain toxic due to residual agent. CWA identification is expected to be straightforward because analytical approaches are well developed. However, identification of the agent alone is not likely to provide substantial forensic information. A more detailed analysis having greater forensic value may be gained by identifying synthetic byproduct compounds that may be present in the agent. Synthetic byproduct compounds are indicative of a synthetic route that was used to synthesize the CWA, and may also contain information on how the agent was stored, stabilized, and released. Because the synthetic byproducts present in the CWAs are unique to synthetic routes used in their formation, these compounds may be used as CAS compounds.

The characterization of CAS compounds on fixed surfaces may be analytically challenging for several reasons. The chemical background in an anthropogenic environment includes a large number of compounds that may be present in high concentrations. For example, virtually any polymeric material will contain a large quantity of plasticizers and solvents, which will produce analytical responses that may be distinguished from those of the CAS compounds. The CAS compounds that are of highest value for identifying synthetic approaches will frequently be present at trace concentrations. These compounds are not formed intentionally, and their concentrations may have been reduced by purification steps used in synthesis. The concentrations of some of the toxins and the CAS compounds may decrease quickly after release, on account of volatilization and loss to the atmosphere, diffusion into a bulk solid, and/or degradation reactions. The CAS compounds may undergo degradation by hydrolysis, photolysis, oxidation, or condensation with other compounds in the chemical environment. Hydrolysis and oxidation reactions may be enhanced by treatment with decontamination solutions during recovery efforts. These degradation reactions may result in changes to the chemical nature of the CAS compounds that drives the need for effective sampling of exposed surfaces.

A method of analyzing organic compounds, such as phosphoryl compounds, sulfide compounds, and amine compounds, may be performed without sample preparation by bombarding surfaces with energetic molecules. More specifically, surface-adsorbed compounds are sputtered into the gas phase where they may be detected using mass spectrometry (MS). The drawback to this method is that it requires acquisition of a sample of the solid surface.

More recently, new approaches have emerged that enable direct interrogation of surfaces using a mass spectrometer. One such approach is desorption electrospray ionization (DESI) mass spectrometry, which utilizes energetic droplets to impact contaminated surfaces. The droplets pick up surface contaminants that are then analyzed, and the technique has recently been demonstrated for analysis of chemical warfare agents. Another approach, referred to as "direct analysis in real time" (DART), utilizes an energetic noble gas plasma to remove surface contaminants that are then analyzed using mass spectrometry. Although these techniques enable on-site analysis, they are expensive, difficult to transport, and hence are not viable options for most law enforcement organizations.

CWA and associated CAS compounds may contact multiple fixed surfaces, and cannot be readily sampled using conventional approaches involving removal and transport to a forensic laboratory for analysis. There is a need for facile, rapid collection of samples containing chemical warfare agent (CWA) attribution signatures after a CWA release.

BRIEF SUMMARY OF THE INVENTION

These and other aspects of the present disclosure will be discussed in greater detail hereinafter.

An embodiment of the present disclosure includes a portable vacuum extraction device that includes a chamber, a plunger slidably inserted from one end of the chamber and having an aperture therethrough, the end of the plunger and aperture covered with a perforable stopper material, the plunger fitted within the chamber such that retraction thereof results in a decrease in pressure within the chamber, at least one sorbent material sized and configured to be inserted through the aperture, and the stopper in the plunger that will sorb chemicals volatilized in the chamber.

Another embodiment of the present disclosure includes a portable vacuum extraction device that includes a vacuum source, a chamber having a first end coupled to the vacuum source and a second, opposite end fitted with a seal and at least one sorbent material disposed within the chamber.

Yet another embodiment of the present disclosure includes a method of detecting one or more chemical compound(s). The methods may include sealing a chamber to a surface having at least one chemical compound thereon, reducing pressure within the chamber to volatilize at least a portion of at least one chemical compound, introducing at least one sorbent material to the volatilized chemical compound within the chamber and analyzing the sorbent material to detect the at least one chemical compound.

BRIEF DESCRIPTION OF THE DRAWINGS

While the specification concludes with claims particularly pointing out and distinctly claiming that which is regarded as the present invention, advantages of this invention may be more readily ascertained from the following detailed description when read in conjunction with the accompanying drawings in which:

FIGS. 5A and 5B are schematic illustrations of a portable vacuum extraction during collection of a chemical compound according to the present disclosure and corresponding gas chromatographic (GC) profiles demonstrating the efficiency of chemical compound collected and show a detection comparison of collection at atmospheric pressure and under vacuum pressure.

FIGS. 6A through 6C are chromatograms obtained from a solid-phase microextraction (SPME) fiber exposed to triethyl phosphate using a device according to an embodiment of the present disclosure.

FIG. 7A, 7 µm polydimethyl-siloxane; FIG. 7B, 65 µm polydimethyl-siloxane-divinylbenzene, and FIG. 7C, 85 µm carboxen-polydimethylsiloxane.

FIGS. 35A through 35C show TD/GC/MS profiles of methoxyethyl ethyl sulfide (MeOEES) and CEES collected from glass using a device according to an embodiment of the present disclosure (plastic syringe body).

FIG. 36 shows mass spectra of CEES and methoxyethyl ethyl sulfide (MeORES) eluting at retention times of about 7.3 minutes and 7.0 minutes shown in FIGS. 35A through 35C.

FIGS. 46 through 74 are TD/GC/MS chromatograms and mass spectra of samples obtained from glass or painted wallboard exposed to chemical compounds using a device according to an embodiment of the present disclosure.

DETAILED DESCRIPTION

Figure 1:
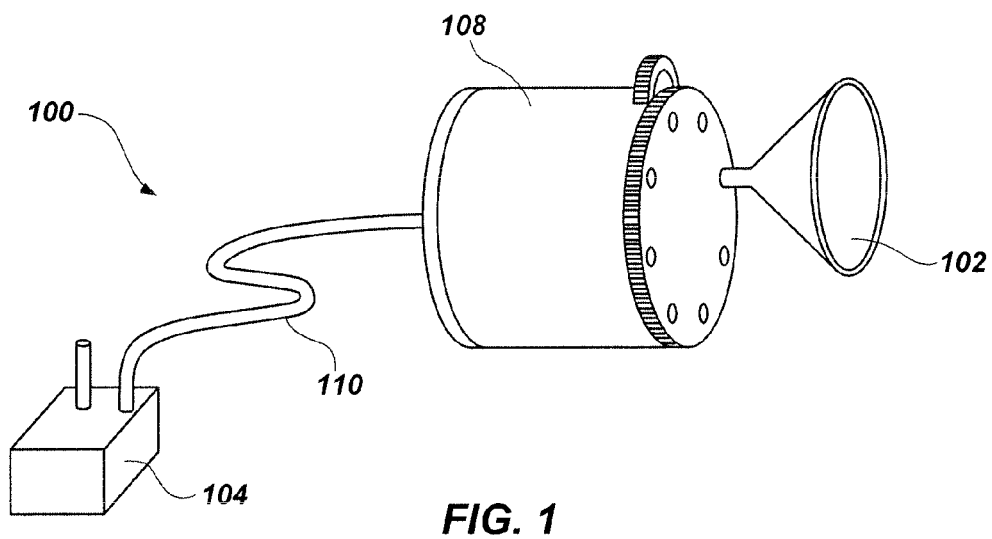
FIG. 1 is an illustration of a portable vacuum extraction device according to an embodiment of the present disclosure.

A portable extraction device and methods of performing extraction are disclosed. In some embodiments, the portable extraction device includes a chamber fitted with a plunger and an absorptive fiber. The portable extraction device may be placed in an area to be sampled and a pressure within the chamber may be reduced by retracting the plunger. In other embodiments, the portable extraction device may be placed over an area to be sampled and a pressure within the chamber may be reduced using a vacuum pump, which increases rates of volatilization of one or more chemical compounds, such as toxic industrial chemicals (TICs), semi-volatile organic or organometallic compounds, or other chemicals of interest. The term "target compound," as used herein, means and includes any chemical compound(s) of interest. A fraction of the volatilized target compounds may be partitioned into the absorptive fiber, which may then be analyzed at a forensic laboratory using a detection method, such as, thermal desorption (TD)/gas chromatography (GC)/mass spectrometry (MS). The portable extraction device enables efficient and cost-effective collection of multiple samples compatible with automated instrumentation and detection methods currently utilized in forensic laboratories. For example, the portable extractor device may be used to quickly collect multiple samples from fixed surfaces after exposure to the target compounds.

Since the target compounds may have limited volatility, they may overwhelmingly partition onto or in fixed surfaces of a release environment and may, thus, be inefficiently sampled in the ambient air. In addition, the target compounds tend to be lipophilic and have a significant dipole moment, which are properties that result in strong surface adsorption or absorption into bulk materials. Thus, they may not be easily detected by direct surface sampling or the use of swipes that are then analyzed. The portable extraction device includes a vacuum to enhance a rate of volatilization of the target compounds and, thus, improves collection. As used herein, the term "vacuum" means and includes a pressure below atmospheric pressure and is expressed with respect to zero pressure (or absolute mode) and not with respect to ambient pressure or some other pressure. It is noted that atmospheric pressure is nominally $1 \times 10^5$ Pa (Pascal) in absolute mode. It is appreciated by a person of ordinary skill in the art that the degree of vacuum may be pressures in a range between about $10^5$ and about $10^{-10}$ Pa, but preferably in a range between about $10^5$ and about $10^{-7}$ Pa, and more preferably in a range between about $10^5$ to about $10^{-4}$ Pa. It is appreciated by a person of ordinary skill in the art that the vacuum may be produced by any conventional vacuum generating equipment.

Many chemical compounds, such as those in chemical warfare agents (CWAs) absorb into or adsorb onto surrounding materials. For example, when the CWA surrogate compounds were applied to polymeric materials, a significant fraction diffused into the polymeric material and could not be detected either on the surface or in the headspace. However, when these samples were analyzed using vacuum extraction mass spectrometry, the direction of diffusion was reversed, and the compounds were volatilized and detected. These studies demonstrated the utility of a vacuum for increasing rates of volatilization over an absorptive surface, and suggested that a vacuum extraction approach might be highly effective for a portable device to collect CWAs and/or target compounds from fixed surfaces.

While inexpensive, hand-held devices according to embodiments of the disclosure may be used for forensics at chemical warfare agent release events, these devices and related methods are useful for detecting any chemicals (industrial, drugs, explosives, etc.) that have been exposed to surfaces, and especially useful for those chemicals with lower vapor pressures. Thus, while the devices may be useful for law enforcement type laboratories (CSI types for state and FBI as well as DHS), the devices may also be useful for the EPA and other agencies that need to detect chemicals from surfaces. These devices may also be useful for private environmental consulting firms that may need to determine if contamination exists at a site, or if remediation strategies have been successful.

While not wishing to be bound by a particular theory, application of a modest vacuum to a contaminated surface may increase rates of volatilization of compounds, such as target compounds, providing efficient, sensitive and cost-effective sampling approaches. Increased volatilization rates may be exploited by coupling a vacuum with an absorptive fiber for capturing volatilized compounds. Use of a sorbent material, such as solid-phase microextraction (SPME) fibers, may be used for capturing vapors in a modest vacuum environment. As used herein, the term "sorbent material" means and includes a material that sorbs another substance and that has the capacity or tendency to take up the substance by either absorption or adsorption. The sorbent material provides a sampling medium compatible with thermal desorption/gas chromatography/mass spectrometry (TD/GC/MS) instrumentation found in most forensic laboratories. The term "TD/GC/MS," as used herein, means and includes thermal desorption (TD) coupled with gas chromatography-mass spectrometry (GC-MS). The combination of a modest vacuum, vacuum extractor, high efficiency SPME fibers, and TD/GC/MS analysis will provide a methodology for effective sampling and analysis for target compounds collected from fixed surfaces.

The portable extraction device of embodiments of the present disclosure takes advantage of increased rates of volatilization at reduced pressures. Current studies show that configuration of the portable extraction device in a static mode is effective for effecting diffusion of absorbed compounds to the surface, and subsequent volatilization. A fraction of the vapors that are generated are captured by absorbent fibers, which are then analyzed using TD/GC/MS.

Collection and identification of the target compounds may pose substantial problems, because they are likely to be inhomogeneously distributed on fixed surfaces that frequently cannot be removed for transport to a forensic laboratory (e.g., walls, windows, etc.). The target compounds will likely be present in low concentrations in an environment that contains high concentrations of background chemicals, and they may be depleted by degradation reactions, volatilization, or diffusion into solid bulk matrices. The device enables rapid and efficient collection of multiple samples of target compounds from fixed surfaces, in order to accurately characterize and attribute origins of released CWA.

The portable vacuum extraction device of embodiments of the disclosure consists of a small pre-evacuated chamber that is placed over the surface to be sampled, a solid-phase microextraction (SPME) fiber, and a valve. Opening the valve modestly reduces the pressure over the surface and increases the rate of target compound volatilization. A fraction of the volatilized target compounds partition into the fiber, which is subsequently analyzed using a thermal desorption/gas chromatography/mass spectrometer, which is instrumentation common to many forensic laboratories. Recovery of target compounds and related impurities was demonstrated from glass and paper surfaces, and the most recent studies indicate efficacy for recovering target signatures from painted wallboard.

Disclosed herein are several embodiments for a portable extraction device prototype. In some embodiments, the portable extraction device includes a pump to provide the continuous vacuum during sampling and may be referred to herein as a "dynamic portable vacuum extractor" (d-PVE). In another embodiment, the portable extraction device includes a pre-evacuated chamber such that a pump is not necessary during the sampling process and may be referred to herein as a "static portable vacuum extractor" (s-PVE). In yet another embodiment, the portable vacuum extraction device may include dual chambers and a suction fan for creating a modest vacuum and may be referred to herein as a "hybrid portable vacuum extractor" (h-PVE). In yet another embodiment, the portable vacuum extraction device may include a syringe with a plunger to create the modest vacuum and may be referred to herein as a "field portable vacuum extractor" (f-PVE).

FIG. 1 is a simplified illustration of an embodiment of a portable extraction device 100 that may be used to collect samples of one or more chemical compounds from a material. The device 100 may include a collector 102, a vacuum pump 104 and a sorbent material (not shown) within a chamber 108. The vacuum pump 104 may be coupled with an end of the chamber 108 opposite an end coupled with the collector 102. Tubing 110 or other similar apparatus may be used to connect the vacuum pump 104 to the chamber 108. The collector 102 may be pressed onto a surface and the vacuum pump 104 may be initiated to reduce a pressure over the surface and volatilize the chemical compounds, such as CWA compounds and chemical attribution signature compounds. The collector 102 may have a seal on an end that contacts the surface. Surfaces may include, for example, glass, plastic, polymeric materials, painted wallboard, paper, and the like. Internal parts of a toy car designed to use vacuum suction created by a fan to crawl on walls, such as an AIR HOGS® toy car, which is available commercially from Spin Master, Ltd. (Toronto, Canada), may be used as the vacuum pump 104 in the device 100. For example, the collector 102 may include a funnel that may be placed over the surface while the vacuum pump 104 is initiated such that volatilized chemicals may pass over the sorbent material and may be captured thereon. The sorbent material may include one or more materials having the capacity to absorb or adsorb chemical compounds of interest. As a non-limiting example, the sorbent material may include an SPME fiber or other suitable sorbent, such as activated carbon, synthetic zeolite, or TENAX®.

Figure 2:
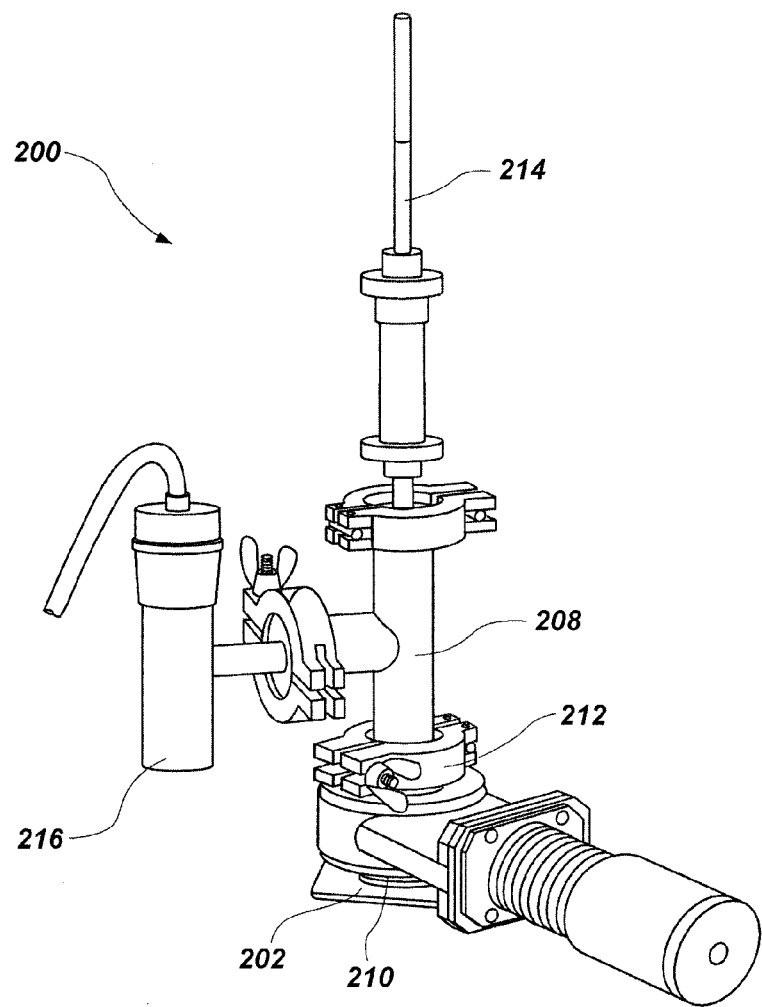
FIG. 2 is an illustration of a portable vacuum extraction device according to another embodiment of the present disclosure.

Referring to FIG. 2, another embodiment of a portable extraction device 200 is shown. The device 200 includes a collector 202, a vacuum pump (not shown), a sorbent material (not shown) within a chamber 208, a seal 210, a valve 212, a sorbent material injector 214 and, optionally, a conventional pressure transducer 216. The seal 210 may be formed from a polymer material, such as polyvinyl ether or SORBOTHANE®, which is commercially available from Sorbothane, Inc. (Kent, Ohio). In some embodiments, the vacuum pump may be initiated to reduce a pressure over a surface (not shown) of a material and volatilize the chemical compounds such that the device 200 functions as a d-PVE. The chamber 208 may be seated over the surface to be sampled, forming a seal over the surface. Pressure within the chamber 208 volume may be reduced using, for example, the vacuum pump, to increase rates of volatilization of the chemical compounds within the chamber 208.

In other embodiments, the chamber 208 may be evacuated before collection rather than being continuously connected to the vacuum pump such that the device 200 functions as an s-PVE. The valve 212 enables the vacuum within the chamber 208 housing the sorbent material to be maintained prior to use of the device 200 to sample the surface. Once the device 200 is placed on the surface, the valve 212 may be opened to expose the surface to the reduced (i.e., vacuum) pressure within the chamber 208. Exposure of the surface to the reduced pressure within the chamber 208 may result in volatilization of chemical compounds on the surface. The s-PVE may be allowed time to equilibrate, enabling partitioning of a significant fraction of the chemical compound into the sorbent material. The sorbent material may be fitted within the chamber 208 and may include, for example, a high capacity, fast absorbing SPME fiber. A fraction of the volatilized chemical compounds may partition into the sorbent material, which may then be analyzed at a forensic laboratory by inserting the sorbent material into a heated injector of a TD/GC/MS.

The first end of the chamber 208 may be placed over a target material before opening the valve 212 to the chamber 208. Thereafter, the valve 212 is opened, which evacuates the atmosphere over the sampled area and contained within the chamber 208. This creates a pressure drop over the surface. A sorbent material, such as an SPME may be inserted into a second end of the chamber 208 to absorb volatilized compounds within the chamber.

Figure 3:
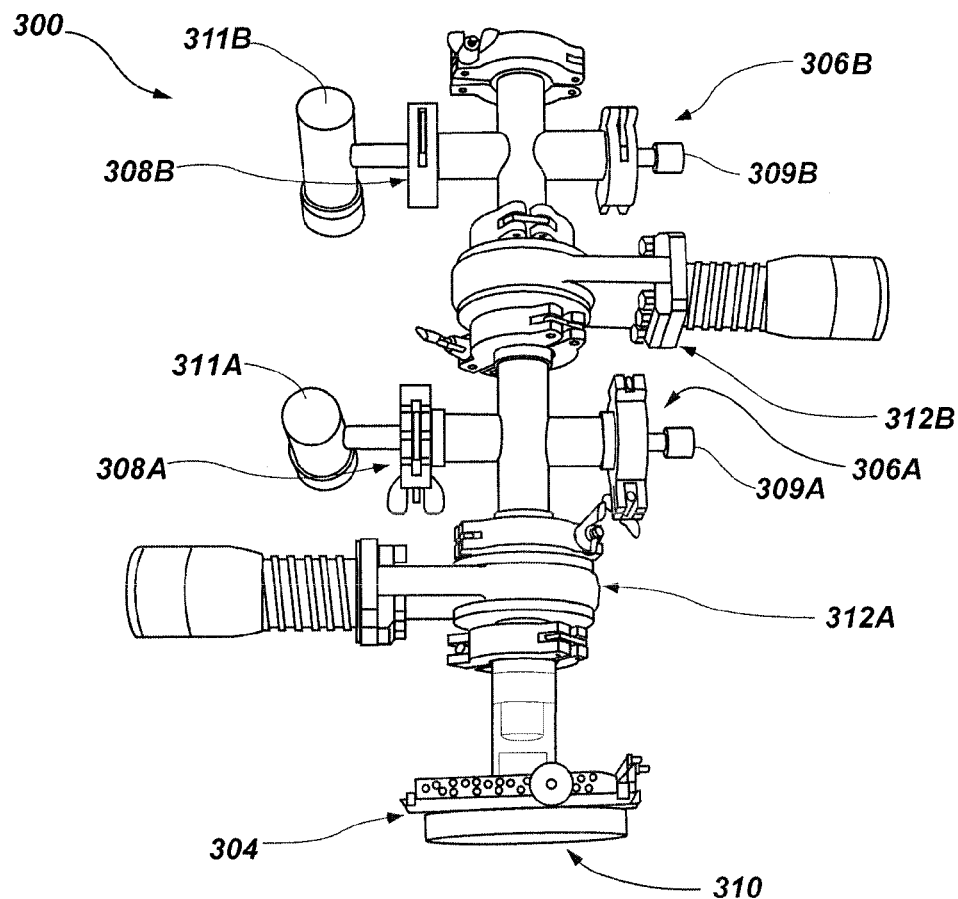
FIG. 3 is an illustration of a portable vacuum extraction device according to another embodiment of the present disclosure.

Referring to FIG. 3, another embodiment of a portable extraction device 300 is illustrated. The device 300 includes a first chamber 308A and a second chamber 308B, each including one or more ports 306A and 306B for introducing a sorbent material (not shown), a vacuum source 304, and a collector 310. The device 300 may also include one or more valves 312A and 312B above the vacuum source at the bottom of the diagram, and respectively between the first chamber 308A and the second chamber 308B. For example, the vacuum source 304 may be any pump or fan device capable of lowering the pressure in the first chamber 308A and second chamber 308B. After placing the vacuum source 304 of the device 300 over a target material, the vacuum source 304 may be used to reduce pressure over the target material and funnel the vapors into the first chamber 308A. The device 300 can be integrated with a simple robotic device capable of climbing the walls to enable vacuum extraction of chemical compounds on remote surfaces. After the pressure over the surface beneath a sampling flange of the collector 310 has been reduced, a first valve 312A may be closed to seal vapors of volatilized chemical compounds in the first chamber 308A, which was actually slightly over atmospheric pressure. The sorbent material, such as an SPME, may then be injected or inserted into the first chamber 308A via a first septum 309A disposed opposite a first convection gauge 311A to absorb the chemical compounds. The second valve 312B may then be opened to expose the contents in the first chamber 308A to the vacuum that had previously been created in the second chamber 308B. Another SPME may then be inserted into the second chamber 308B via a second septum 309B disposed opposite a second convection gauge 311B. The second SPME exposed to the reduced pressure environment showed a greater collection of target compounds than did the first SPME under higher pressure.

Figure 4A:
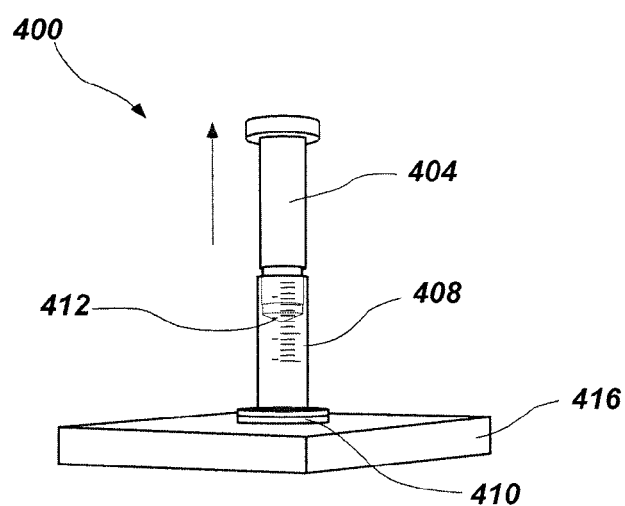
FIGS. 4A through 4C illustrate a portable vacuum extraction device according to another embodiment of the present invention and illustrate a method of collecting one or more chemical compound(s) according to an embodiment of the present disclosure.
Figure 4B:
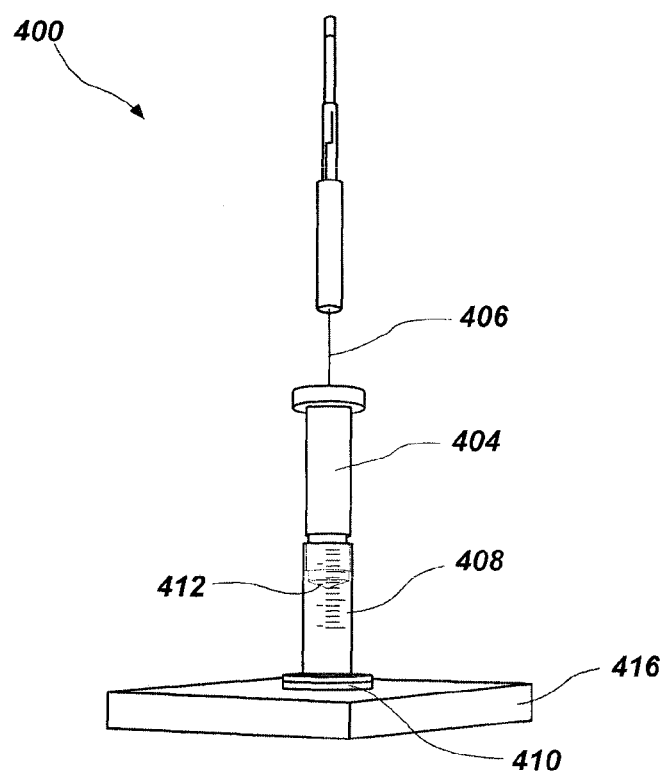
Figure 4C:
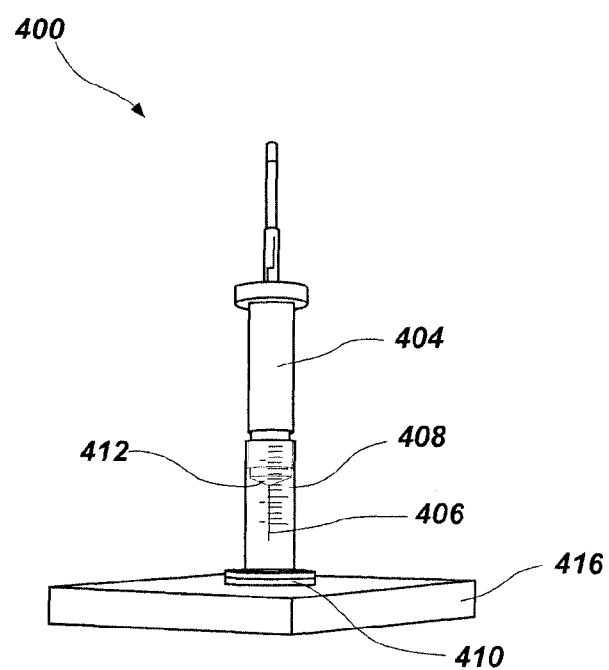

FIGS. 4A through 4C show an embodiment of a field vacuum extraction device 400 that includes a chamber 408, a plunger 404, a sorbent material 406 and a seal 410. The plunger 404 has a diameter equivalent to the inside diameter of the chamber 408, such that the plunger 404 is slidably insertable into the chamber 408. A cavity is formed through the plunger 404 by, for example, drilling, longitudinally such that the plunger 404 contains an open, cylindrical void or space extending along a length of the plunger 404, which is thus open on both ends. The end of the plunger 404 is fitted with a stopper material (e.g., stopper 412) that is perforable by a sampling fiber or device, such as an SPME pen (Supelco, St. Louis, Mo.) for delivering the sampling fiber. The seal 410 may be formed from a polymer material, such as polyvinyl ether (PVE) or SORBOTHANE®. The aforementioned cylindrical space extends through the plunger 404 and may have a diameter sufficient to pass the sorbent material 406 therethough. For example, the field vacuum extraction device 400 may be formed from a polymeric (i.e., plastic), metal or glass syringe modified by removing a constriction and a needle lock from a barrel thereof (i.e., the chamber 408), adding a sealing gasket (i.e., the seal 410) between a sample surface 416 and the chamber 408, and replacing a conventional plunger with the plunger 404, which is sized and configured to accommodate a sorbent material 406, such as a conventional solid-phase microextraction (SPME) fiber. Use of a plastic syringe provides a lightweight, inexpensive and rugged field vacuum extraction device 400.

The plunger 404 may be formed from a material such as plastic, TEFLON® (i.e., polytetrafluoroethylene) or other material, such as metal. As shown in FIG. 4A, the field vacuum extraction device 400 may be placed over the surface 416 to be sampled and the plunger 404 may be retracted to create a modest vacuum over the surface 416, which is made possible by the seal 410. Having retracted the plunger 404, the sorbent material 406 (i.e., the SPME fiber) may be inserted through the cylindrical open space within the plunger 404, as shown in FIG. 4B. The sorbent material 406 may be extended into the chamber 408 by perforating a stopper 412 on the end of the plunger 404, such that a portion of volatilized chemical compounds within the chamber 408 may be absorbed by the sorbent material 406, as shown in FIG. 4C. The sorbent material 406 may be retracted and stored for transport back to a laboratory for analysis using standard gas chromatography (GC) or gas chromatography mass spectrometry (GC/MS) instruments that are common to most forensic laboratories.

As a non-limiting example, two or more SPME pens with sorbent material may be used with a single field vacuum extraction device 400 with modifications to the plunger 404. Additional sorbent materials of the same type may provide duplicate samples for verification or storage for future reference, such as for forensic evidence. Additional sorbent materials of different types, such as having different chemical selectivity, may be used to broaden the range of chemical compounds being analyzed.

The field vacuum extraction device 400 may be used to collect or recover a single chemical compound or multiple types of chemical compounds from the surface 416 of the sample. For example, the field vacuum extraction device 400 may be used to recover samples having vapor pressures at about 20° C. of between about 0.01 torr and about 1 torr, and more particularly, between about 0.1 torr and about 0.8 torr. For example, the field vacuum extraction device 400 may be used to collect alcohols, acids, esters, halo compounds, sulfides, phosphoryl derivatives, amines, and phosphates. Examples of compounds that may be collected using the field vacuum extraction device 400 include diisopropylaminoethane thiol (DIPAE), 2,3-dimercapto-1-propanol (DM-1-P), 3-mercapto-1,2-propanediol (3M1,2PD), N-ethyl diethanol amine (NEDEA), N-methyl diethanolamine (NMDEA), 1,3-propanedithiol (PDT), dithiolane, 2,2'-thiodiethanol (thiodiglycol or TDG), diethyl dithiophosphate (DEDTP), diethyl methylphosphonate (DEMP), diisopropyl methylphosphonate (DIMP), dipinacolyl methylphosphonic acid (DPMP), diethyl ethylphosphonate (DEEP), diethyl phosphite (DEPt), O-ethyl methylphosphonothioate (EMPT), triethyl phosphite (TEPt), 2-chloroethylethylsulfide (CEES), ethyl dichlorothiophosphate (EDCTP), esters of ethyl dichlorophosphate (EDCP), 1,3-propanedithiol (1,3-PDT), 2,2-tetrachlorodiphenylethane (2,2-TDE), and N-methylethylenediamine (NMEDA). Analysis of recovered samples was performed primarily on a GC/MS, but also on a GC only instrument. There are some differences in the response of the two analytical instruments, which is due to the difference in columns each instrument used and not to the PVE device itself. The parts exposed to the volatilized chemical compounds are disposable and inexpensive, so there is no carry over from one sample to the next. Because the field vacuum extraction device 400 requires only operator power (i.e., no external power source), includes lightweight, inexpensive and disposable parts, and does not required large apparatus such as valves, pumps or fans, the field vacuum extraction device 400 is well suited for collection of chemical compounds in the field. Although examples of materials that may be used to form the field vacuum extraction device 400 are provided herein, the present disclosure is not limited to particular materials.

EXAMPLES

Example 1

To standardize comparison, test samples were prepared including 400 µg of tributyl phosphate (TBP) on filter paper (WHATMAN® Grade 41 quantitative filter paper, which is commercially available from Whatman Inc., Piscataway, N.J.) and/or glass.

FIGS. 5A and 5B show a schematic comparison of design and function of extraction of compounds of interest 501 using an SPME fiber 506 overlying test samples 516 at atmospheric pressure and in the presence of a vacuum pressure. There are multiple interactions that have different equilibrium and kinetic rates. There is the rate of volatilization of the target compounds from the surface material, the rate that the target compounds sorb onto the parts of the device (i.e., the wall of the chamber), and the rate that the target compounds sorb to the SPME fiber 506. FIG. 5A illustrates that the amount of target compound that could be sorbed onto the SPME fiber 506 in the headspace at atmosphere would be rather low, if seen at all. However, a small vacuum placed over the sample as illustrated in FIG. 5B increases the volatilization of the analyte or target compounds from the surface of test samples 516. While reducing the pressure will increase the volatilization of target compound(s), there are other competing processes that affect the design of a vacuum extraction device, such as the equilibrium and kinetics associated with the sorption of the target compound(s) onto the SPME fiber 506 as illustrated in the expanded view in FIG. 5B. The interaction of the target compound(s) with the wall 508 of the vacuum chamber is not illustrated.

The devices described herein may be optimized to balance the interactions. As a non-limiting example, the chamber of any of the embodiments of the devices of the present disclosure may be heated to substantially reduce or eliminate sorption or adherence of the target compound to surfaces of the chamber.

Figure 6B:
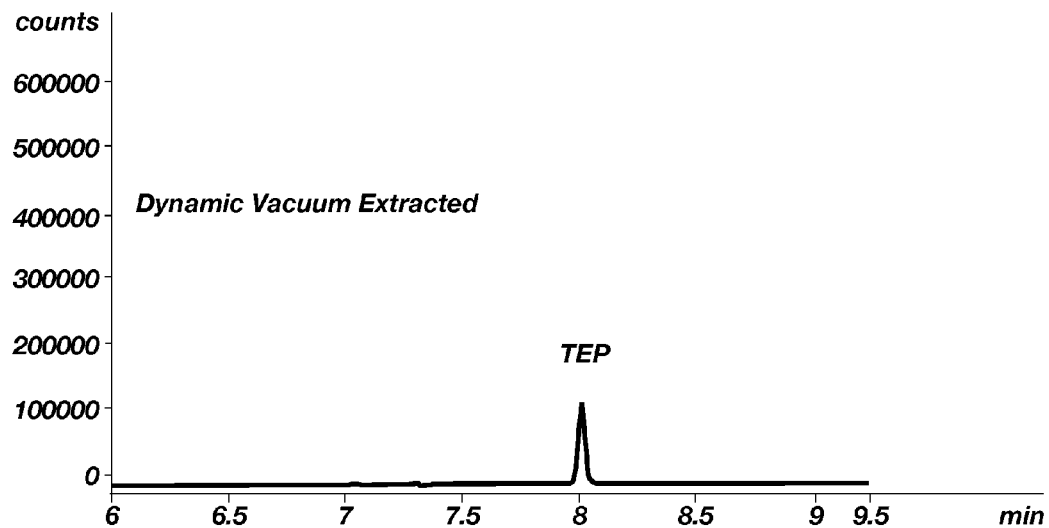
Figure 6C:
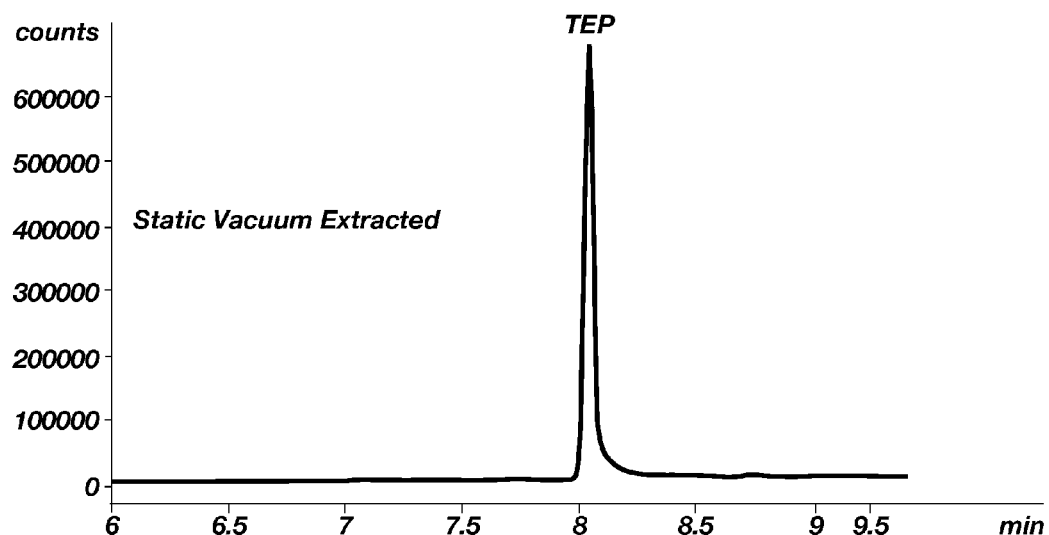

FIGS. 6A through 6C provide a comparison of sample collection from a test sample using an SPME as a sorbent material in the devices described with respect to FIGS. 2 and 3 with sample collection at atmospheric pressure. FIG. 6A is a chromatogram of the sample collected with the SPME at atmospheric pressure. FIG. 6B is a chromatogram of the sample collected using the device similar to that shown in FIG. 1 using a vacuum pump (i.e., a d-PVE) to reduce pressure over the sample surface and an SPME used as the sorbent material placed within a flow path between a sample surface and the vacuum pump. FIG. 6C is a chromatogram of the sample collected using the device 200 shown in FIG. 2 having a pre-evacuated chamber (i.e., an s-PVE) used to reduce pressure of the sample surface. As shown in FIGS. 6B and 6C, an increased amount of sample is detected using either embodiment (i.e., d-PVE or s-PVE) in comparison to an amount of sample collected at atmospheric pressure (FIG. 6A). While not wishing to be bound by any particular theory, the device 200 described with respect to FIG. 2 may have increased efficiency using a pre-evacuated chamber in comparison to using a device with a continuous vacuum pump, as described with respect to FIG. 1, because there is more time for the target compounds to equilibrate with the sorbent fiber in the s-PVE design, while the amount of time required to establish equilibrium between the volatilized chemical compounds and the SPME may exceed the residence time of the target compounds in a d-PVE chamber.

Figure 6D:
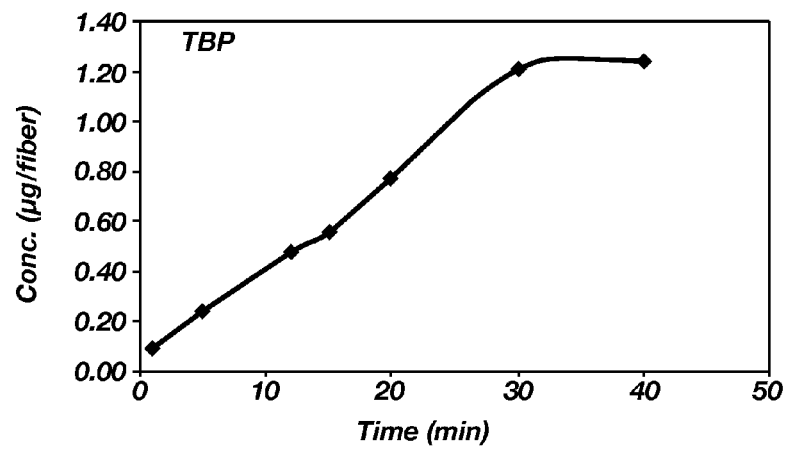
FIG. 6D is a plot illustrating collection of TBP according to an embodiment of the present disclosure with increasing sampling time.

In a dynamic portable vacuum extractor (d-PVE) device, the chemical compounds may stream past the SPME and ultimately into and out of the vacuum pump resulting in a decrease in collection by the sorbent fiber. Thus, even though the pressure readings for both experiments were the same above the sample, the s-PVE device 200 having the pre-evacuated chamber, may have increased effectiveness due to the increase of residence time of the vapors with the SPME. The effect is shown in dramatic fashion by the experiment represented by FIG. 6D, in which a tributyl phosphate (TBP) response increases steadily over a thirty (30) minute timeframe when sampled using the portable extraction device 200 shown in FIG. 2 as an s-PVE. These experiments suggest that a minimum pressure that the pre-evacuated chamber of the static device should be at about 50 torr when exposed to the SPME.

Example 2

Figure 7A:
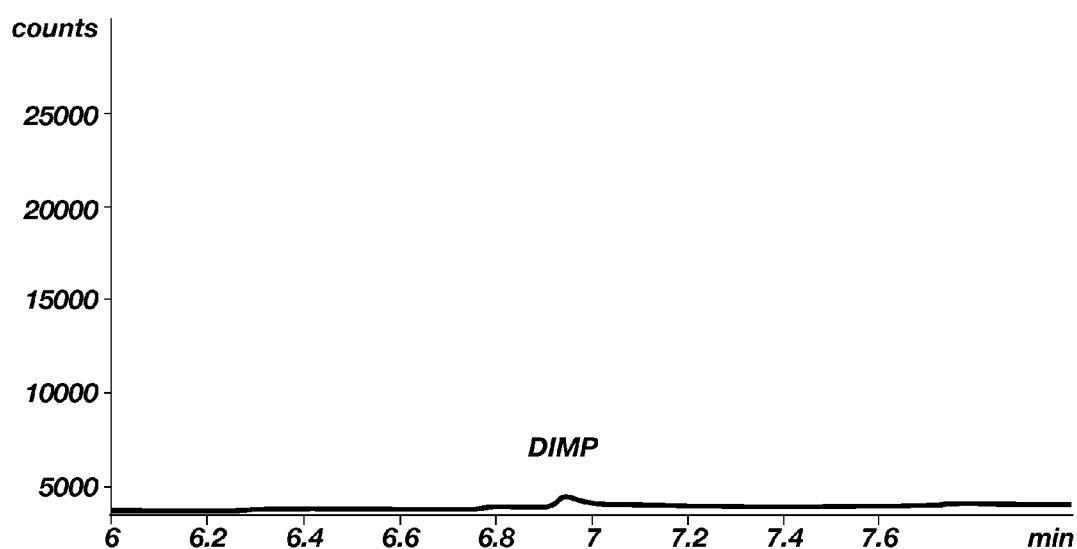
FIG. 7A through 7C are gas chromatograms obtained during collection of DIMP comparing different SPME fibers, according to an embodiment of the present disclosure (metal body PVE). SPME fiber composition.
Figure 7B:
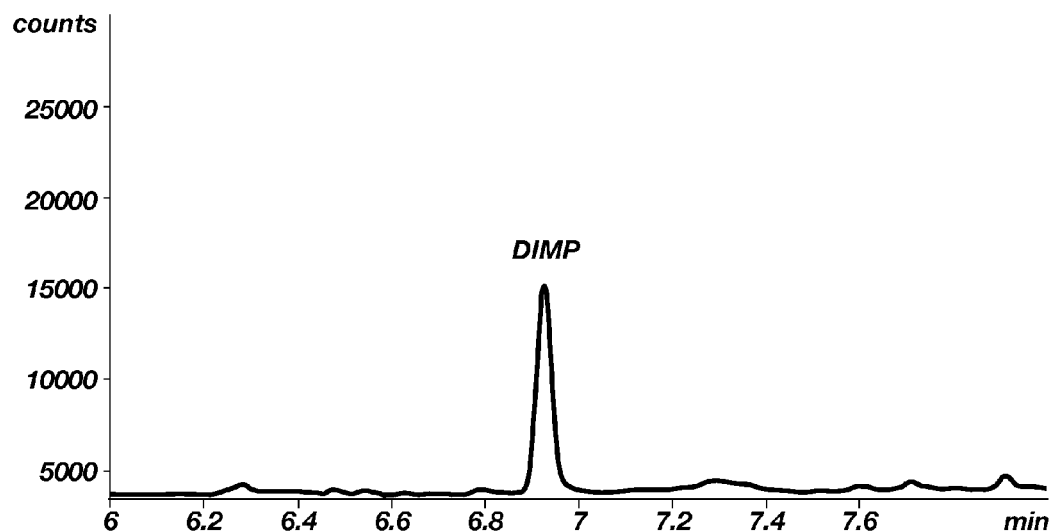
Figure 7C:
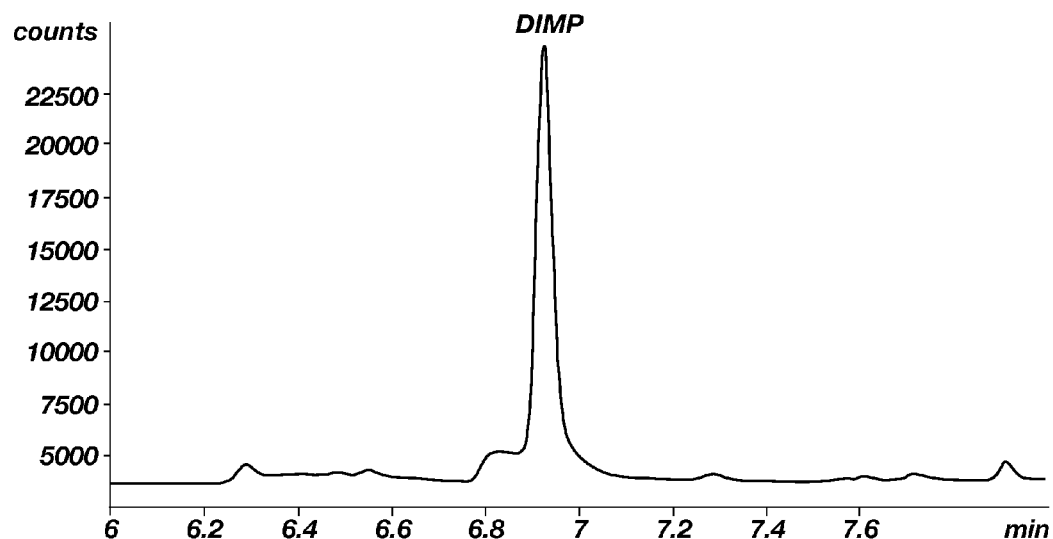

Tests were conducted to determine which type of SPME fiber works best for detecting the CAS of interest. Some of the SPME fiber types tested include 100 µm polydimethylsiloxane, 85 µm polyacrylate, 75 µm carboxen-polydimethylsiloxane, 85 µm carboxen-polydimethylsiloxane, 65 µm polydimethylsiloxane-divinylbenzene, and 7 µm polydimethylsiloxane. Even for a given fiber material (e.g., polydimethylsiloxane), the physical characteristics also play a role in how well the SPME absorbs an analyte. As illustrated in FIGS. 7A through 7C, there may be a substantially significant difference in response for the same CAS analyte for different fiber types. FIG. 7A is a gas chromatogram obtained for DIMP using the 7 µm polydimethylsiloxane. FIG. 7B is a gas chromatogram obtained for DIMP using the 65 µm polydimethylsiloxane-divinylbenzene. FIG. 7C is a gas chromatogram obtained for DIMP using the 85 µm carboxen-polydimethylsiloxane. The 85 µm carboxen-polydimethylsiloxane demonstrated improved performance over the other SPMEs tested, which may be generally applied to absorption of organic analytes.

Example 3

Trace quantities of CAS compounds were applied to surfaces and were sampled using the portable extraction device 200 described with respect to FIG. 2, which produced exposed SPME fibers that were analyzed using TD/GC/MS. Glass was chosen for a non-absorptive surface because it is a matrix that is of significant forensic value, and because its surface could be effectively cleaned, removing background from the subsequent GC/MS analyses that were performed. This latter consideration is important because it simplified the analyses and subsequent interpretations, easing identification of signature compounds, impurities and degradation products.

Diethylphosphite (DEPt) is a relatively small molecule, which may lead to the expectation that it may readily partition into the gas phase, and perhaps volatilize before it could be effectively sampled. However, DEPt also has a significant P—O (phosphorous-oxygen) dipole that may produce very strong bonding with both Lewis and Brønsted acid/base sites found on matrix surfaces. This factor may result in longer persistence on surfaces.

Figure 8A:
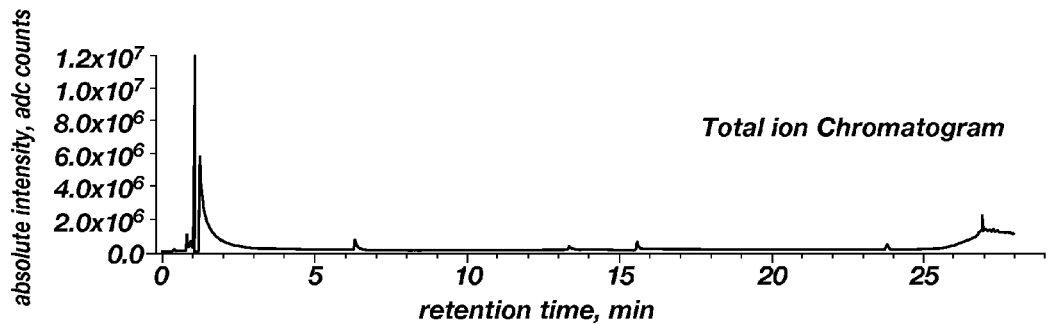
FIGS. 8A through 8C are TD/GC/MS profiles of diethylphosphite (DEPt) eluting from the GC at about 13.4 min, collected from glass using a device (metal body) according to an embodiment of the present disclosure.
Figure 8B:
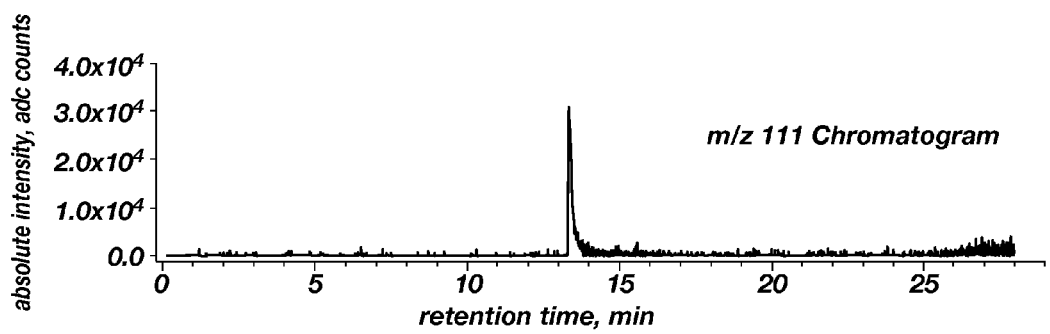
Figure 8C:
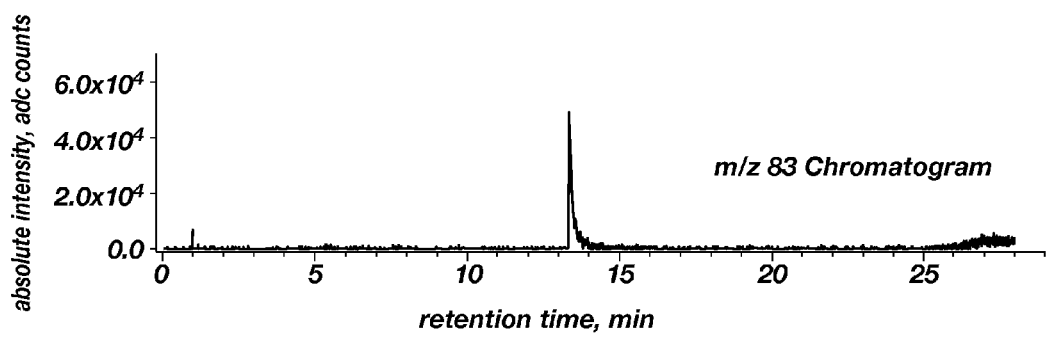
Figure 9:
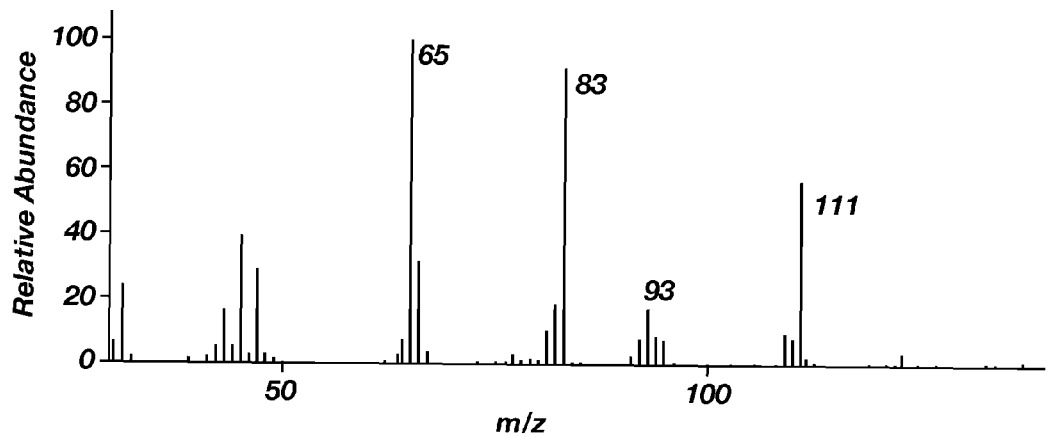
FIG. 9 is a mass spectrum of DEPt collected from glass at a RT of about 13.4 minutes using a device (metal body) according to an embodiment of the present disclosure.
Figure 10:
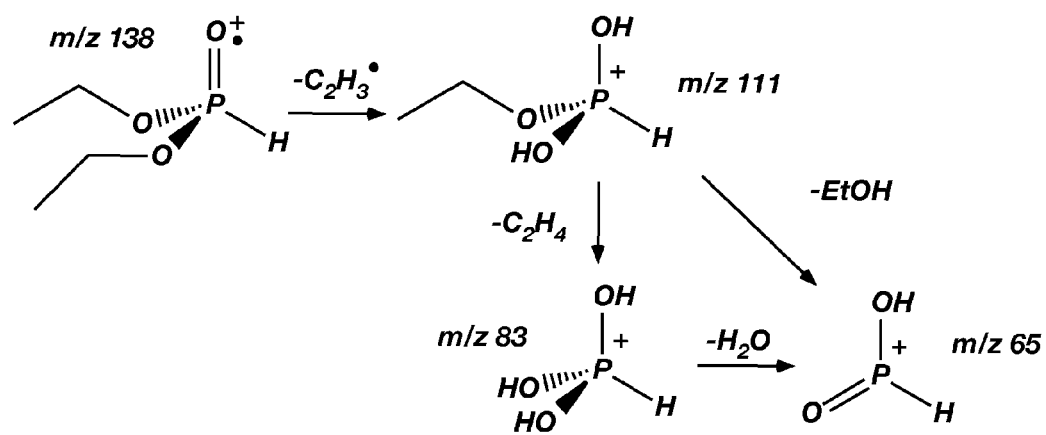
FIG. 10 is a schematic diagram of the mass spectrometric fragmentation of DEPt collected using a device according to an embodiment of the present disclosure (metal body).

The portable extraction device 200 was placed over a glass surface to which DEPt had been applied. The valve of the portable extraction device 200 was opened, and the SPME fiber was exposed to a vacuum environment for five (5) minutes, after which time the valve was closed. As shown in FIGS. 8A through 8C, analysis of the SPME fiber principally showed air detected at retention times (RT) of less than about two (2) minutes, and column bleed at a RT of about 25 minutes. Referring to FIG. 9, a small peak at a RT of about 13.4 min was ascribed to DEPt on the basis of its mass spectrum. FIGS. 9 and 10 illustrate a low abundance ion as m/z 138 corresponds to the DEPt molecular ion, which undergoes facile elimination of a $C_2H_3$ radical to furnish m/z 111, and a serial elimination of $C_2H_4$ and or $C_2H_5OH$ to make m/z 83 and m/z 65, respectively. The overall response of the GC/MS is modest, however, examinations of the single ion chromatograms shown in FIGS. 8B and 8C show that the traces for both m/z 111 and m/z 83, respectively, are well above background, indicating that lower quantities may be well above detection limits. Other small peaks observed in the chromatogram had mass spectra that corresponded to PDMS that likely originated either from the SPME or from the column.

Figure 11A:
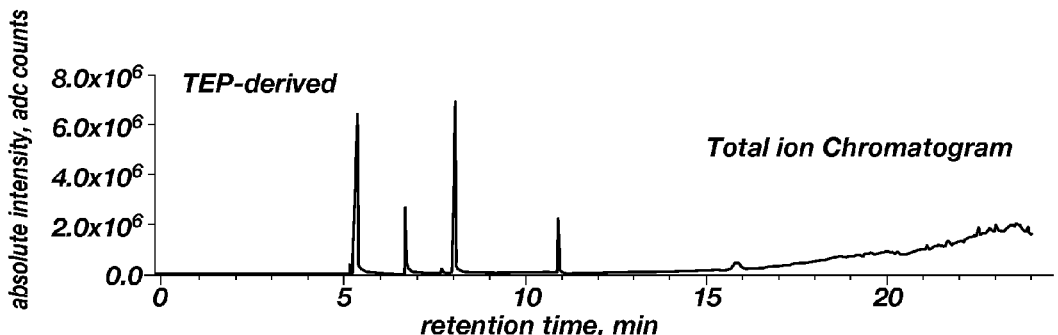
FIGS. 11A through 11C are TD/GC/MS profiles of triethyl phosphate (TEP) collected from glass using a device according to an embodiment of the present disclosure (metal body).
Figure 11B:
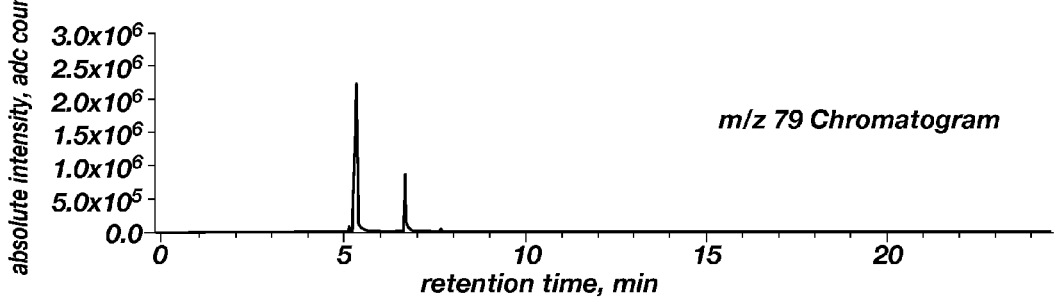
Figure 11C:
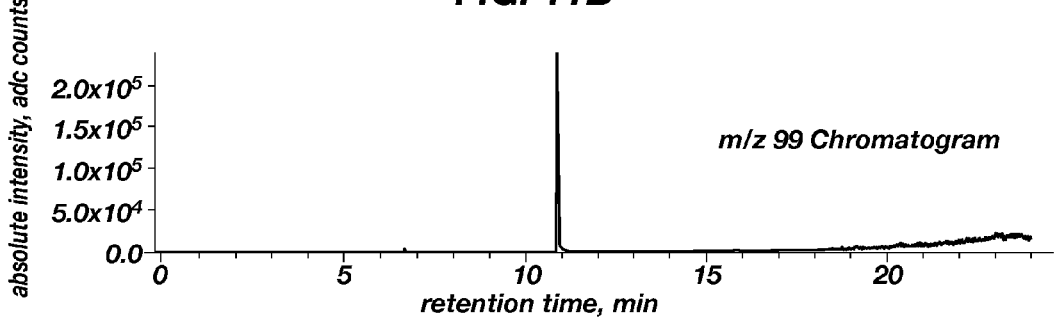
Figure 12:
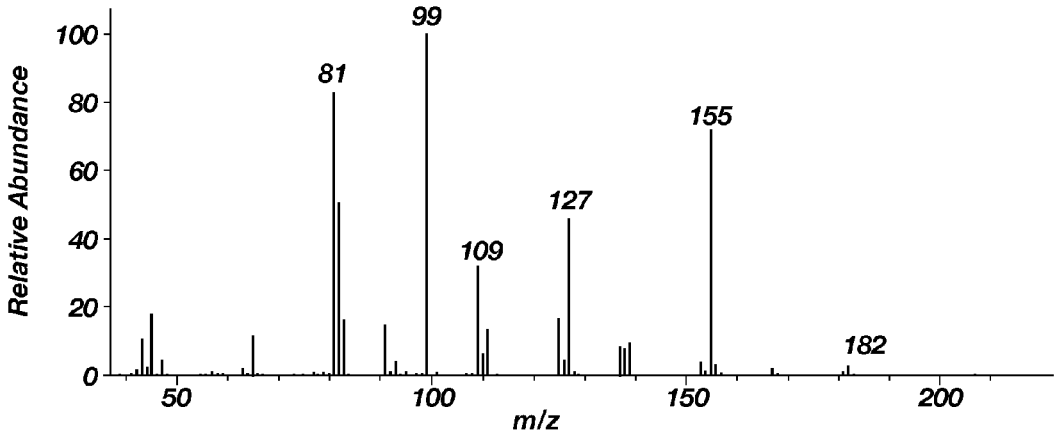
FIG. 12 is a mass spectrum of TEP at a RT of about 10.9 minutes obtained from a sample collected from glass using a device according to an embodiment of the present disclosure (metal body).
Figure 13:
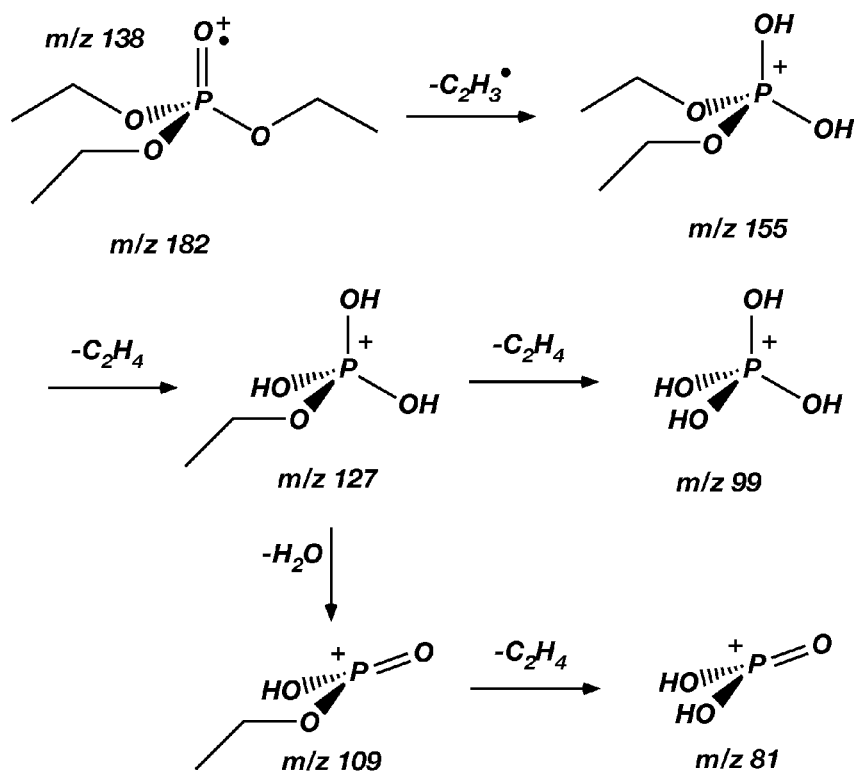
FIG. 13 is a schematic diagram of the mass spectrometric fragmentation of TEP collected from glass using a device according to an embodiment of the present disclosure (metal body).

Referring to FIGS. 11A through 11C, analysis of triethyl phosphate (TEP) applied to glass surfaces resulted in a GC/MS chromatogram that contained four peaks, all of which were likely derived from TEP or are a carryover from prior experiments. FIG. 12, which is a mass spectrum of compounds eluting at a RT of about 10.9 minutes, displayed a mass spectrum that corresponds to intact TEP, as indicated by a low-abundance peak at m/z 182 that is consistent with the ionized molecule. Several abundant fragment ions that arise from losses of $C_2H_3$ radical (forming m/z 155) and subsequent losses of $C_2H_4$ and or $H_2O$. Serial losses of two $C_2H_4$ molecules from m/z 155 produce $[H_4PO_4]^+$ at m/z 99, which is typical of fragmentation seen in the mass spectra of the trialkylphosphate derivatives. FIG. 13 is a mass spectrometric fragmentation of TEP.

As shown in FIG. 11C, m/z 99 is a strong indicator for the presence of the trialkylphosphates. In several analyses, other peaks were observed at a RT of about 5.3 minutes, about 6.6 minutes and about 8.1 minutes. The mass spectra of these compounds clearly indicated that they were organophosphorus compounds. The abundant ion at m/z 79 is suggestive of methyl phosphonate derivatives, as previously discussed, and it is prominent in the spectra of compounds eluting at about 5.3 minutes and about 6.6 minutes, which are shown in FIG. 11B.

Figure 14:
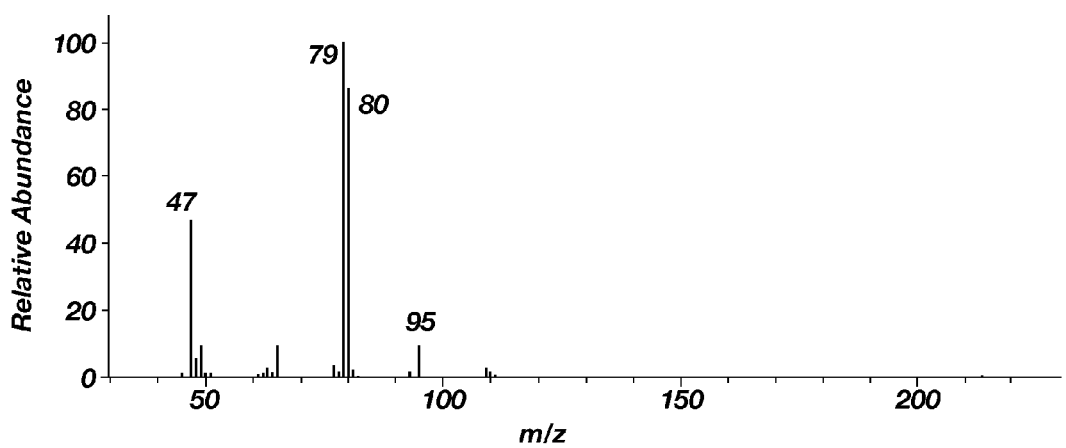
FIG. 14 is a mass spectrum of compound eluting at a RT of about 5.3 minutes obtained from a sample collected from glass from a glass surface exposed to TEP using a device according to an embodiment of the present disclosure (metal body).
Figure 15:
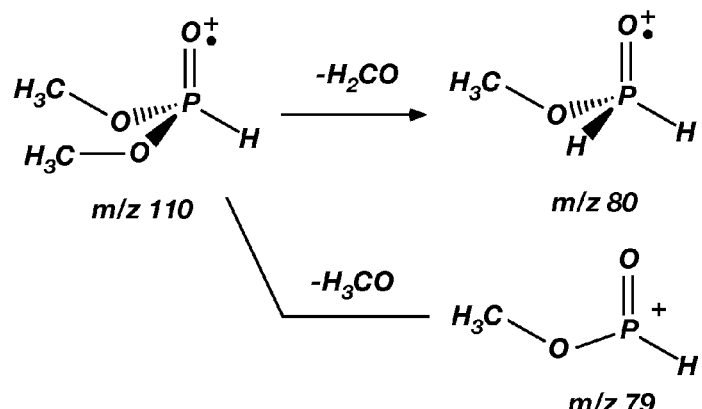
FIG. 15 is a schematic diagram of the mass spectrometric fragmentation for dimethylphosphite (DMPt) collected from glass using a device according to an embodiment of the present disclosure (metal body).

FIG. 14 is a mass spectrum for the peak at a RT of about 5.3 minutes and contains abundant peaks at m/z 80 and m/z 79 that indicate dimethylphosphite (DMPt). DMPt did not likely originate from degradation of TEP and, thus, may be an impurity in the TEP standard, or an impurity derived from carryover of the DEPt. DMPt was not seen in the DEPt analysis, however, it may be formed by alkoxy exchange with the methanol solvent. FIG. 15 is schematic diagram of mass spectrometric fragmentation for DMPt.

Figure 16:
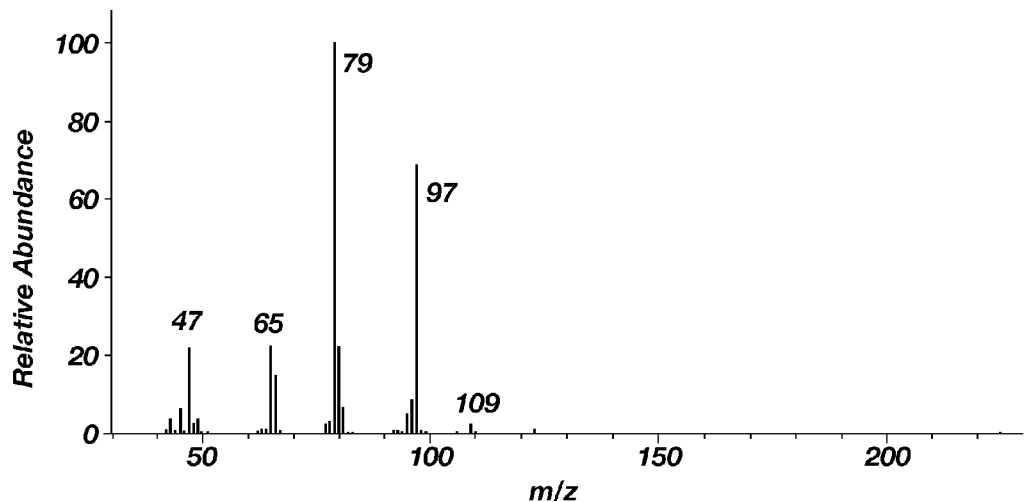
FIG. 16 is a mass spectrum of compound eluting at a RT of about 6.65 minutes obtained from a sample collected from glass using a device according to an embodiment of the present disclosure (metal body).
Figure 17:
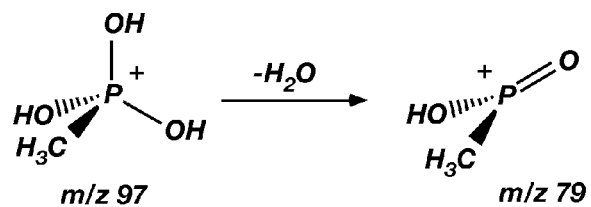
FIG. 17 is a schematic diagram of the mass spectrometric fragmentation for ethyl methyl phosphite (EMPt) collected from glass using a device according to an embodiment of the present disclosure (metal body).

FIG. 16, which shows the mass spectrum of a compound eluting at a RT of about 6.65 minutes, is consistent with ethyl methyl phosphite (EMPt), in which case the abundant ion at m/z 97 arises from elimination of the $C_2H_3$ radical, a process that is followed by dehydration to form the ion at m/z 79. FIG. 17 is a proposed mass spectrometric fragmentation for EMPt.

Figure 18:
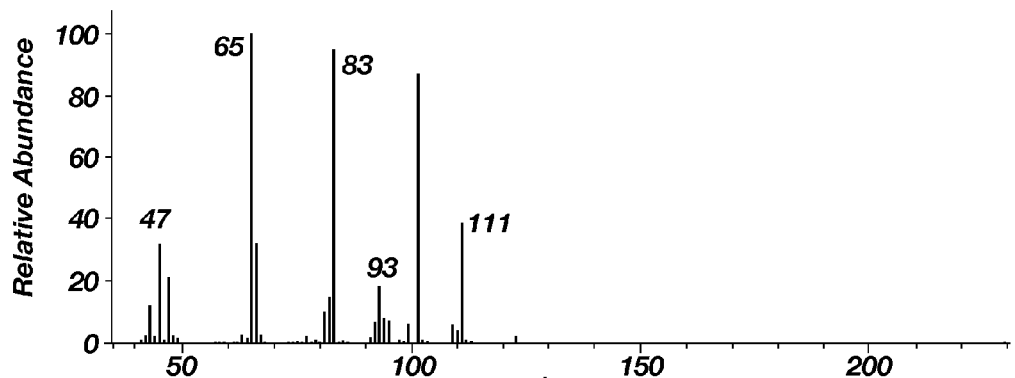
FIG. 18 is a mass spectrum of the compound eluting at a RT of about 8.05 minutes, probably diethyl phosphite (DEPt), obtained from a sample from glass collected using a device according to an embodiment of the present disclosure (metal body).

Referring to FIG. 18, a mass spectrum of compound eluting at a RT of about 8.05 minutes that is indicative of DEPt is depicted (see also FIG. 9).

Figure 19:
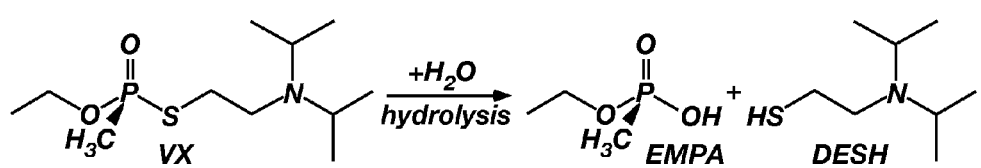
FIG. 19 is an illustration of hydrolysis of O-ethyl S-[2-(diisopropylamino)ethyl] methylphosphonothiolate (VX), which produces ethyl methylphosphonic acid (EMPA) and diisopropylaminoethanethiol (DESH).

As shown in FIG. 19, ethyl methylphosphonic acid (EMPA) is both a synthon for, and a degradation product of O-ethyl S-[2-(diisopropylamino)ethyl] methylphosphonothiolate (VX). Diisopropylaminoethanethiol (DESH) is also a hydrolysis product of VX. The methylphosphonic acids are moderately strong acids, having $pK_a$ values of between about 2.3 and about 2.5, and hence may be present in the conjugate base form in many environments. This phenomenon serves to make volatilization difficult, and in fact, the EMPA conjugate base will strongly bind to many surfaces. Nevertheless, the PVE was able to volatilize and absorb a significant amount of DEMP, which is the esterified acid EMPA, as indicated by a strong signal at a RT of about 17 minutes in the total ion chromatogram, as shown in FIG. 20A.

Figure 20A:
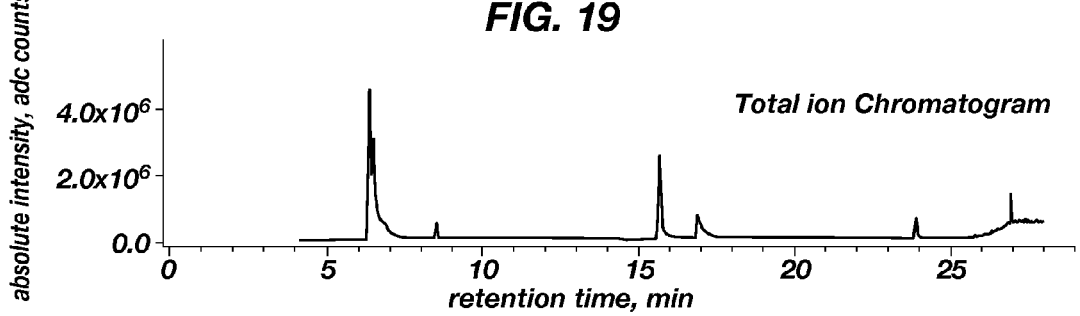
FIGS. 20A through 20C are TD/GC/MS profiles of compounds collected from glass exposed to a solution of ethyl methylphosphonic acid (EMPA). Samples were acquired using a device according to an embodiment of the present disclosure (metal body).
Figure 20B:
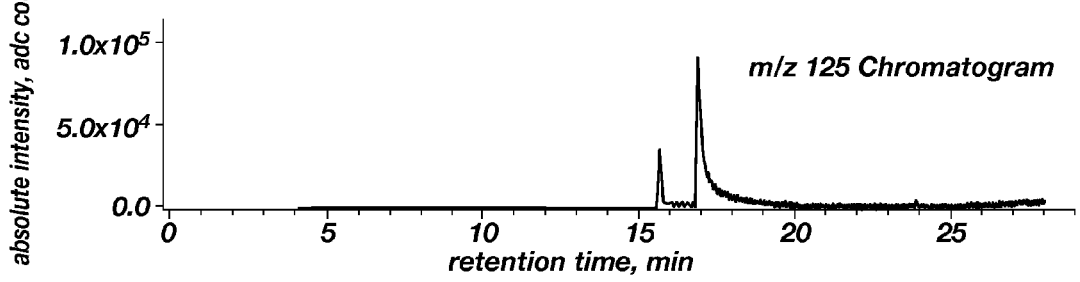
Figure 20C:
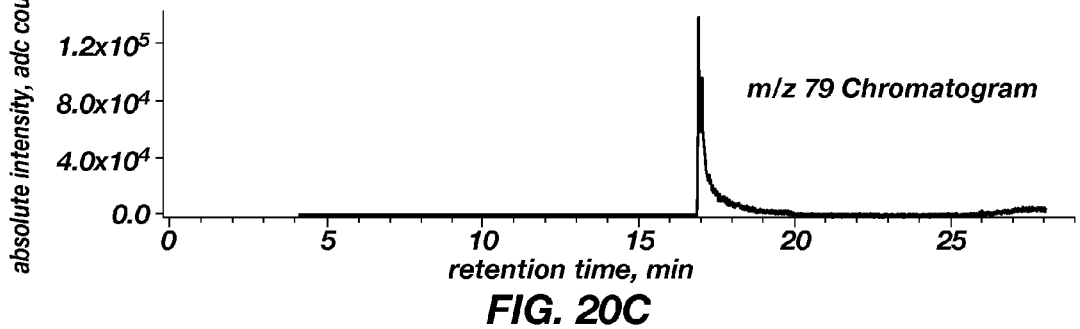
Figure 21:
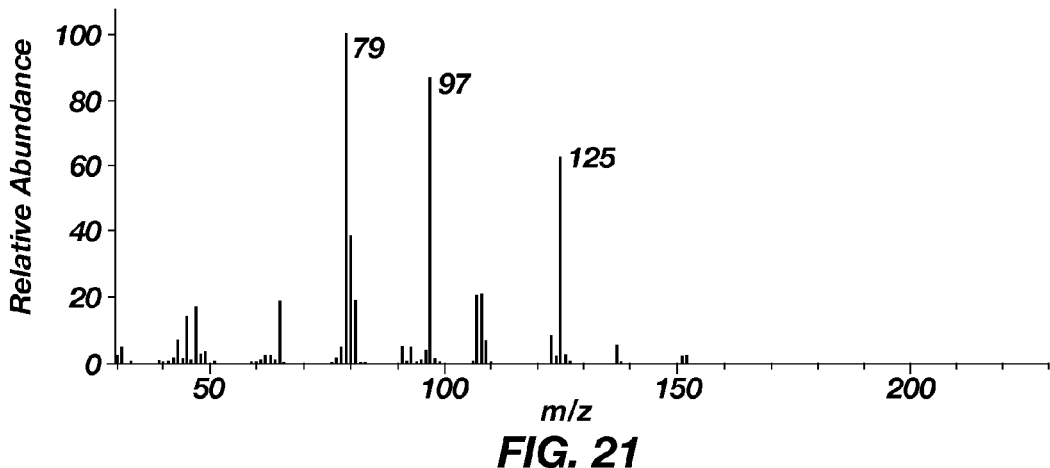
FIG. 21 is a mass spectrum of DEMP eluting at a RT of about 17 minutes shown in FIGS. 20A through 20C.
Figure 22:
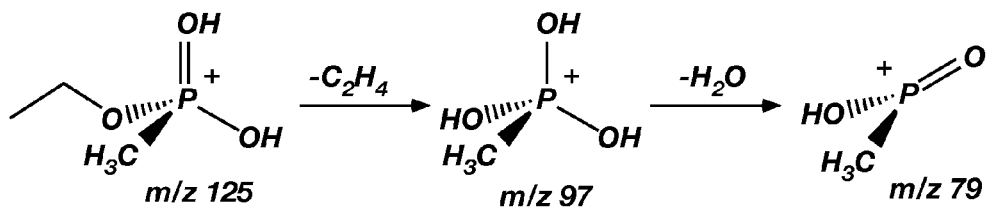
FIG. 22 is a schematic mass spectrometric fragmentation for DEMP.

The gas chromatograms shown in FIGS. 20A through 20C and the mass spectrum shown in FIG. 21 establishes the identity of DEMP, with a low abundance ion at m/z 152 corresponding to the protonated molecule. The intense ion at m/z 125 arises by elimination of the $C_2H_3$ radical, and undergoes a further fragmentation by loss of $C_2H_4$ to form m/z 97, followed by loss of $H_2O$ to form m/z 79 as shown in FIG. 22.

Figure 23A:
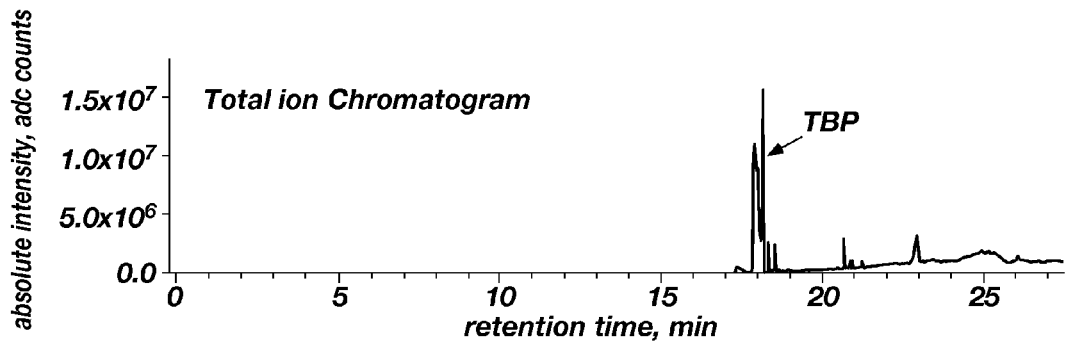
FIGS. 23A through 23C are TD/GC/MS profiles of tributyl phosphate (TBP) collected from a glass surface using a device according to an embodiment of the present disclosure (metal body).
Figure 23B:
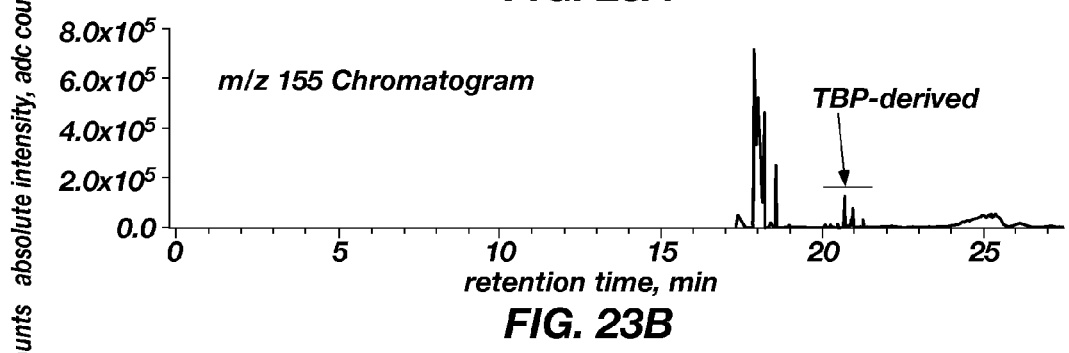
Figure 23C:
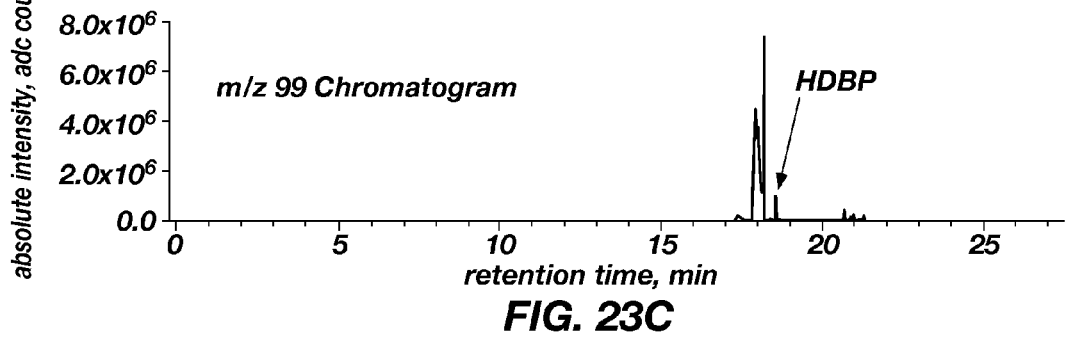
Figure 24:
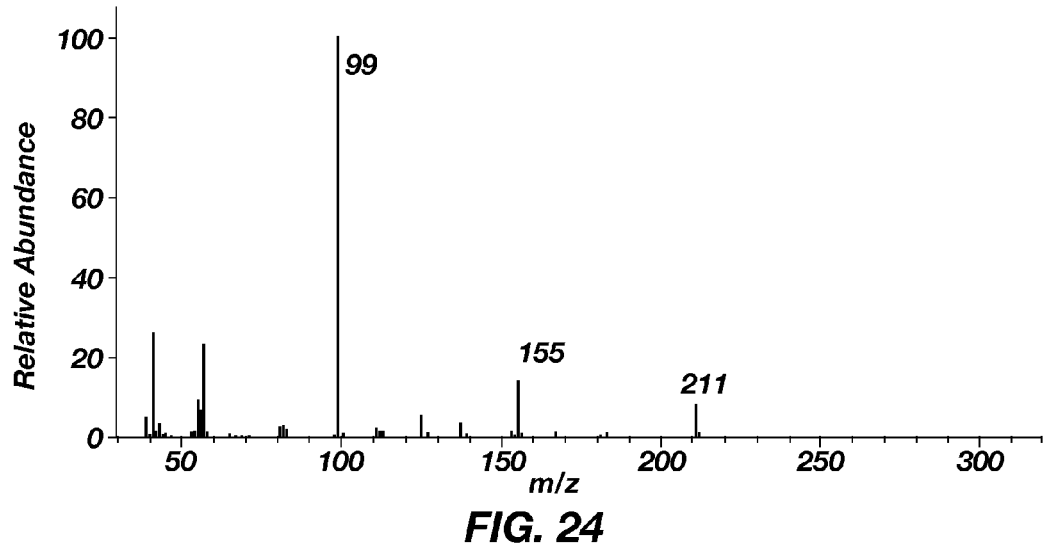
FIG. 24 is a mass spectrum of TBP collected from glass exposed to TBP using a device according to an embodiment of the present disclosure (metal body).
Figure 25:
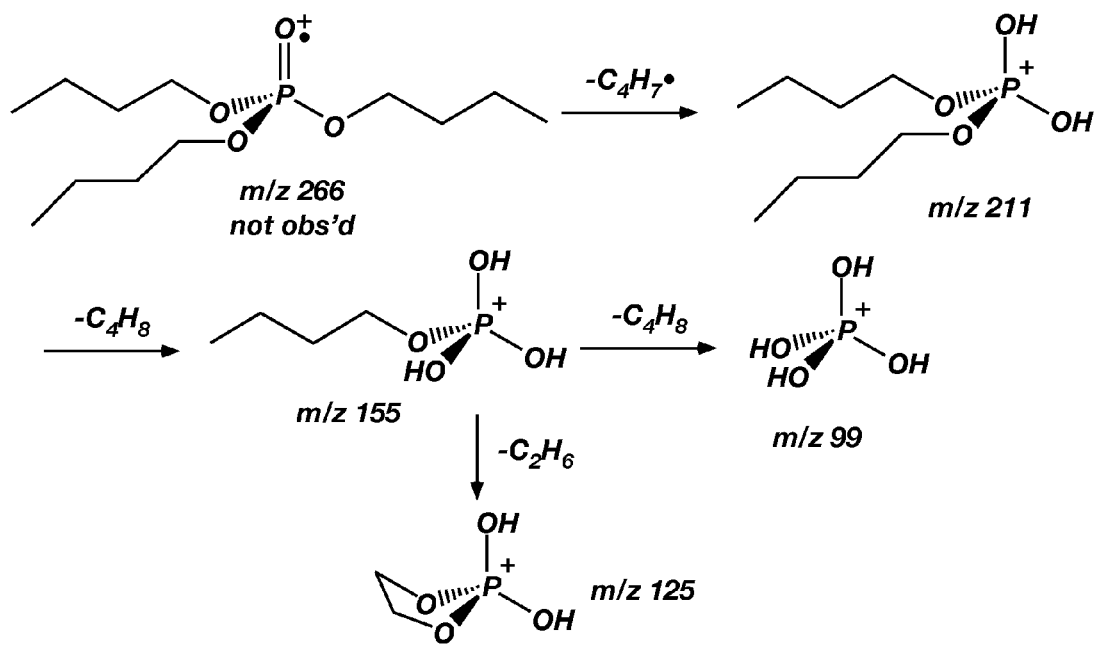
FIG. 25 is a schematic diagram of the mass spectrometric fragmentation of TPB.

TBP is the least volatile of the compounds in this example. It has a molecular weight of 266 g/mol, nearly equivalent to VX, is highly lipophilic, and strongly adsorbs to surfaces through Lewis base/acid interactions of the phosphoryl group. For these reasons it is used as a stimulant for VX, however TBP is also of interest because it is used as an extractant in nuclear fuel reprocessing. As shown in FIGS. 23A through 23C, a gas chromatogram measured from a PVE sample of glass exposed to TBP showed a poorly resolved peak at about 18 minutes. Another peak at 18.7 min is likely hexyl, dibutyl phosphate that is present as an impurity in the TBP. The profile of the chromatographic peak, no doubt, is due to adsorption occurring at the injector or in the MS interface, indicating that chromatographic optimization is needed for more condensable, less volatile compounds. Despite the chromatographic problems, the mass spectrum correlated with that of TBP (FIGS. 24 and 25).

Figure 26:
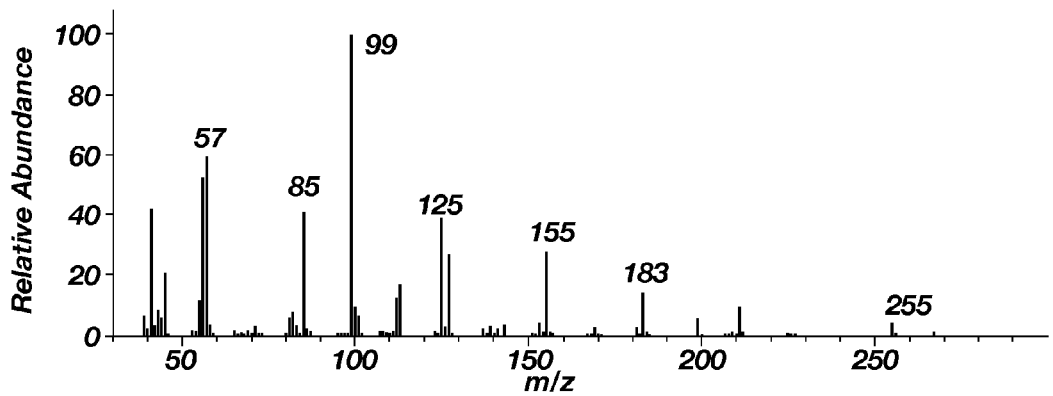
FIG. 26 is a mass spectrum of a TBP-derived compound collected from glass exposed to TBP using a device according to an embodiment of the present disclosure (metal body).

As shown in FIG. 26, mass spectra of other compounds observed in the GC/MS analysis appeared to be TBP-related. A spectrum of compound at a RT of about 18.7 minutes, which is shown in FIGS. 23A through 23C, contains the same ensemble of peaks, as does TBP, but with several additional peaks. For example, the ion at m/z 183 is 28µ higher than m/z 155, suggesting the presence of a hexyl substituting for one of the butyl groups, in which case the identity of the compound may be hexyl, dibutyl phosphate. This assignment is supported by the abundant ion at m/z 85 that may be derived from the hexyl cation $C_6H_{13}^+$ but does not account for the low abundance ion at m/z 255, and so this compound has not yet been identified.

In addition to the peak at retention time 18.7, there were several lower abundance compounds eluting between about 20 and about 20.5 minutes that were unquestionably butyl organophosphoryl in nature, as indicated by the single ion chromatograms for m/z 99 and m/z 155 (FIGS. 23A through 23C). These compounds either could be derived from reactions occurring on the glass surface, or are present as impurities in the TBP spike solutions. Their appearance shows that the PVE sampling is picking up synthetic impurities in the synthetic mixtures.

Example 4

A matrix of high priority is painted wallboard (PWB), because it is a very common fixed surface in many indoor environments. Compared with glass, it may be expected that the PWB may present different challenges for sampling CAS compounds, in part because the organic, painted coating will be absorptive, and in part, because a high chemical background might obscure the GC/MS signature of the CAS compounds. In this example, a portable vacuum extraction according to an embodiment of the present disclosure was used to sample chemical compounds from a surface of painted wallboard.

Figure 27A:
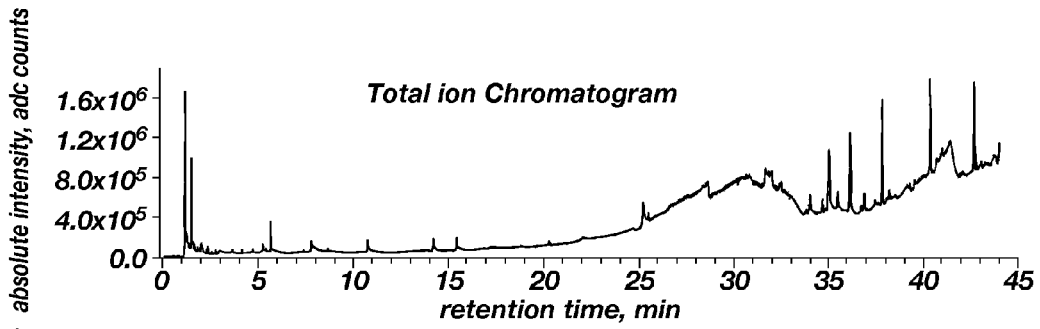
FIGS. 27A through 27C are TD/GC/MS profiles of DMMP collected from painted wallboard using a device according to an embodiment of the present disclosure (metal body).
Figure 27B:
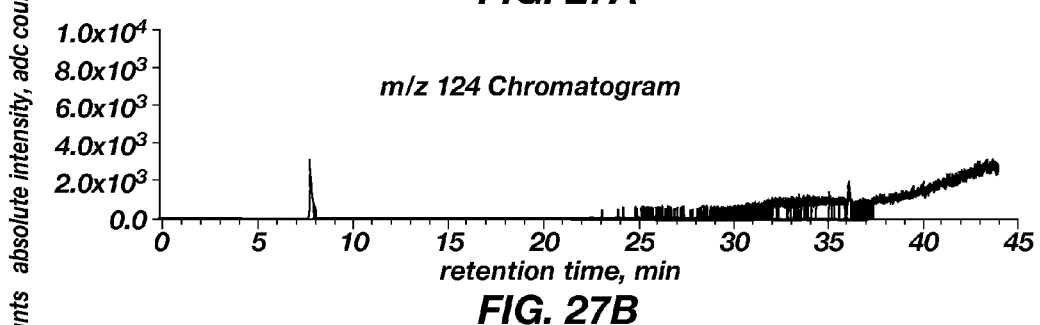
Figure 27C:
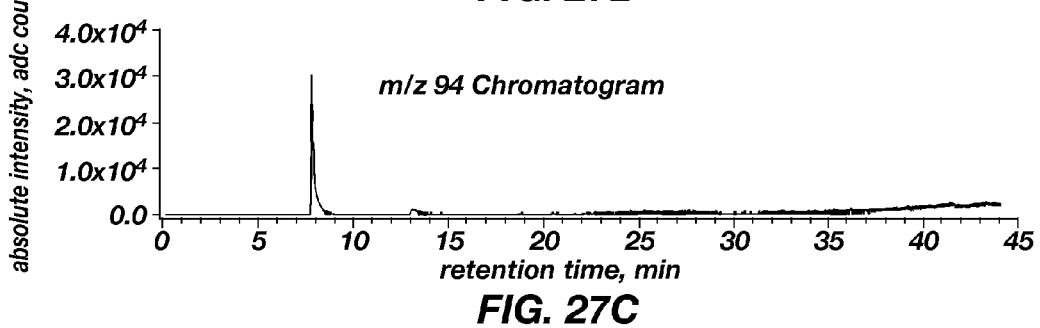
Figure 28:
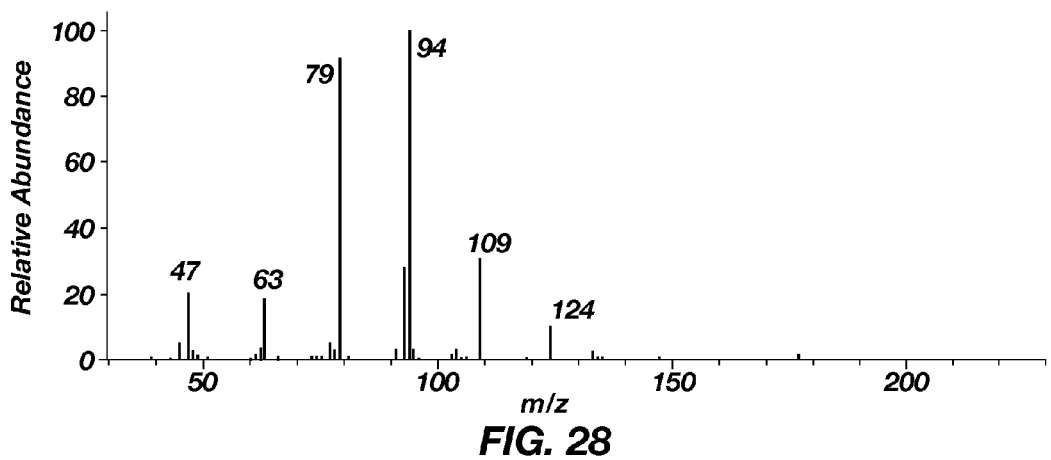
FIG. 28 is a mass spectrum of DMMP acquired from the peak of FIGS. 27A through 27C eluting at a RT of about 7.8 minutes.
Figure 29:
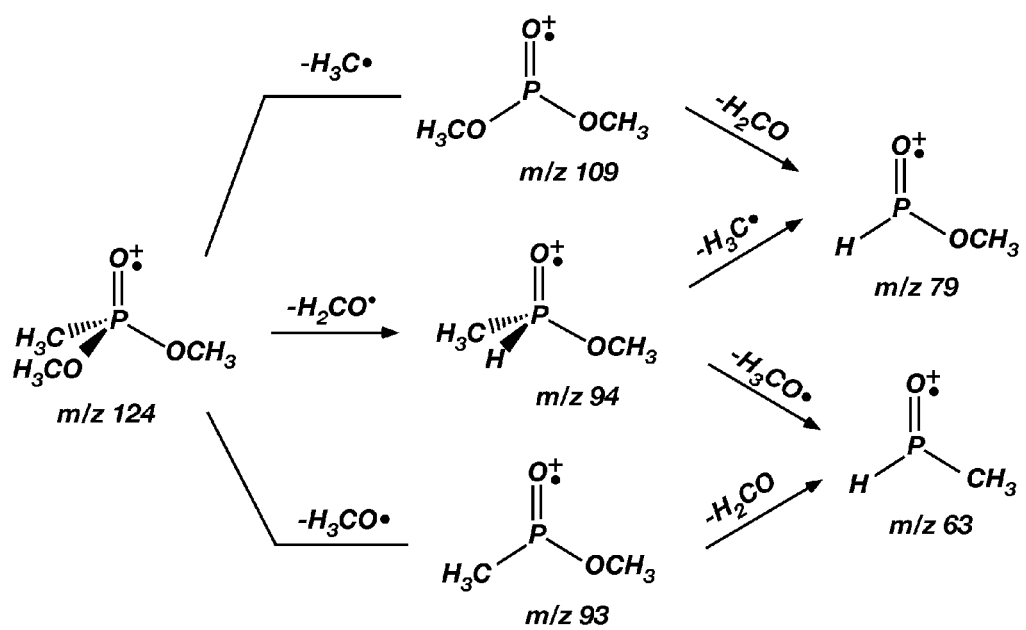
FIG. 29 is the schematic diagram of the mass spectrometric fragmentation for DMMP.

FIGS. 27A through 27C are TD/GC/MS profiles of DMMP collected from painted wallboard. Initial GC/MS chromatograms showed a background derived from the painted wallboard was significantly higher in comparison to a background derived from the glass surfaces, particularly at RT values of about 20 minutes. However, the DMMP that was added to the painted wallboard was detected at about 7.8 minutes. Referring to FIG. 28, a mass spectrum showed a low abundance molecular ion at m/z 124, with all other significant fragment ions interpreted in terms of losses of formaldehyde, a methoxy radical, and or a methyl radical. The individual ion chromatograms did not reveal any further DMMP-derived ions. FIG. 29 is the schematic for the mass spectrometric fragmentation for DMMP.

Figure 30A:
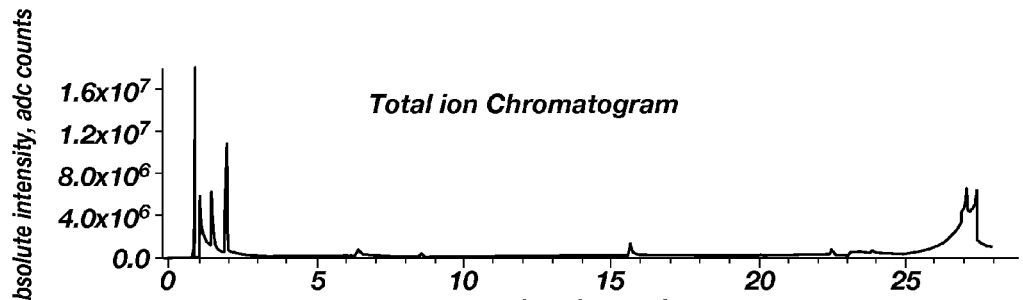
FIGS. 30A through 30C are a collection of TD/GC/MS profiles of DESH hydrochloride collected from glass using a device according to an embodiment of the present disclosure (metal body).
Figure 30B:
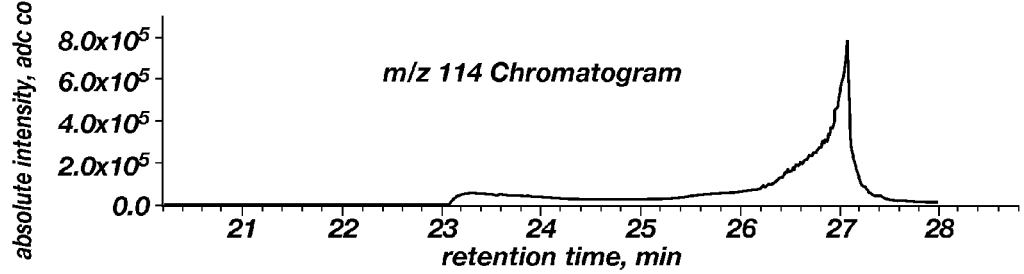
Figure 30C:
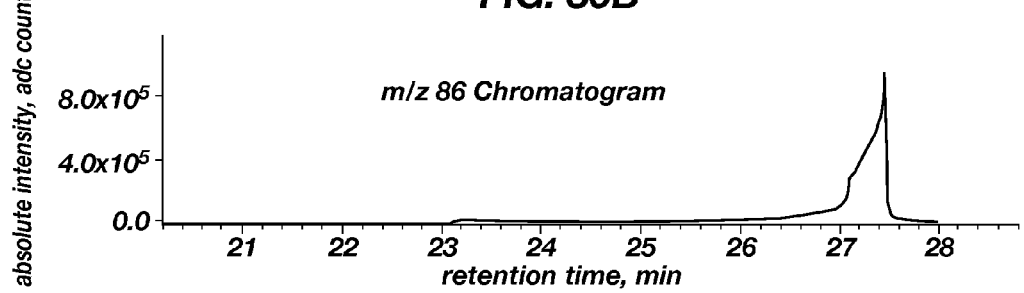
Figure 31:
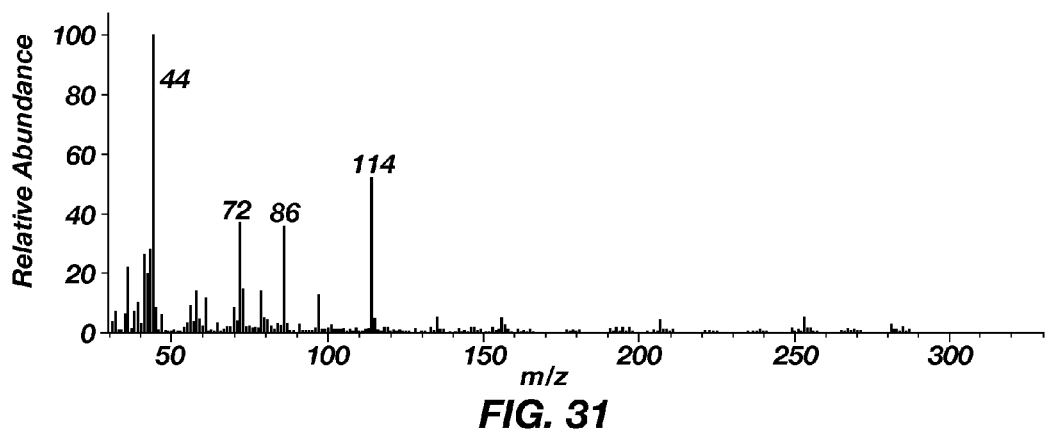
FIG. 31 is a mass spectrum of DESH eluting at a RT of about 27.1 minutes as shown in FIG. 30B.
Figure 32:
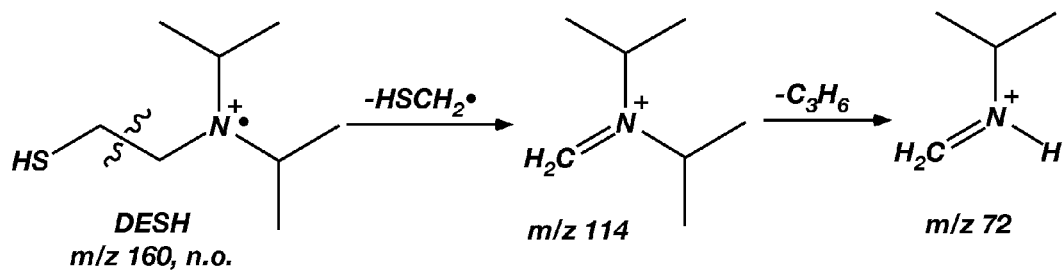
FIG. 32 is a schematic diagram for the formation of m/z 114 and m/z 72 shown in FIG. 31 by fragmentation of the DESH radical cation.

FIGS. 30A through 30C are a collection of TD/GC/MS profiles of DESH hydrochloride applied to glass. N,N-diisopropylaminoethane thiol (DESH) is both a synthon for, and a degradation product of VX (FIG. 19). The chromatographic profile showed a broadened two-topped peak at RT of about 27 minutes, with a four-minute leading edge. Referring to FIGS. 30B and 31, the mass spectra demonstrate that the compound eluting at about 27.1 minutes may be either DESH, or a closely related compound. As shown in FIG. 32, elimination of the $HSCH_2$ radical from the DESH radical cation produces m/z 114, which then eliminates $C_3H_6$ to furnish m/z 72. Loss of the HS radical accounts for formation of m/z 128, which surprisingly is not detected; instead, an abundant ion at m/z 86 is formed, which may ordinarily be rationalized as loss of $C_3H_6$ from m/z 128; m/z 86 eliminates $C_3H_6$ to form m/z 44.

Figure 33:
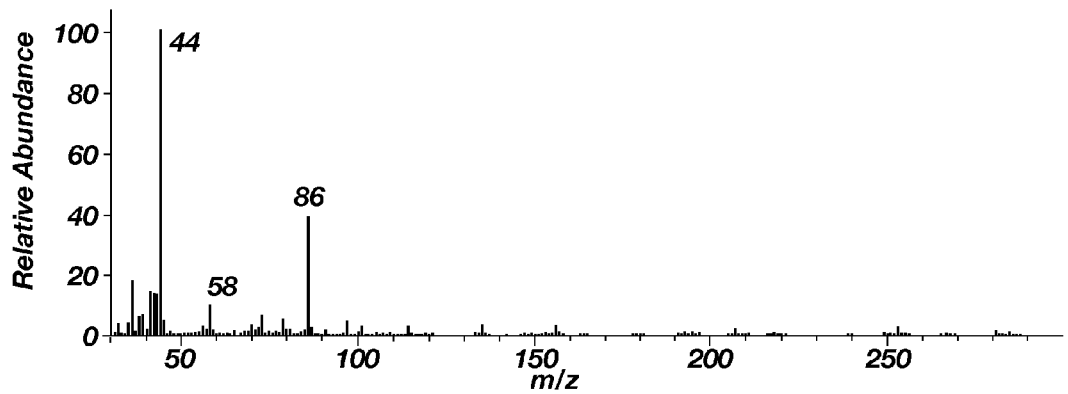
FIG. 33 is a mass spectrum of a DESH-derived compound eluting at a RT of about 27.5 minutes as shown in FIG. 30C.
Figure 34:
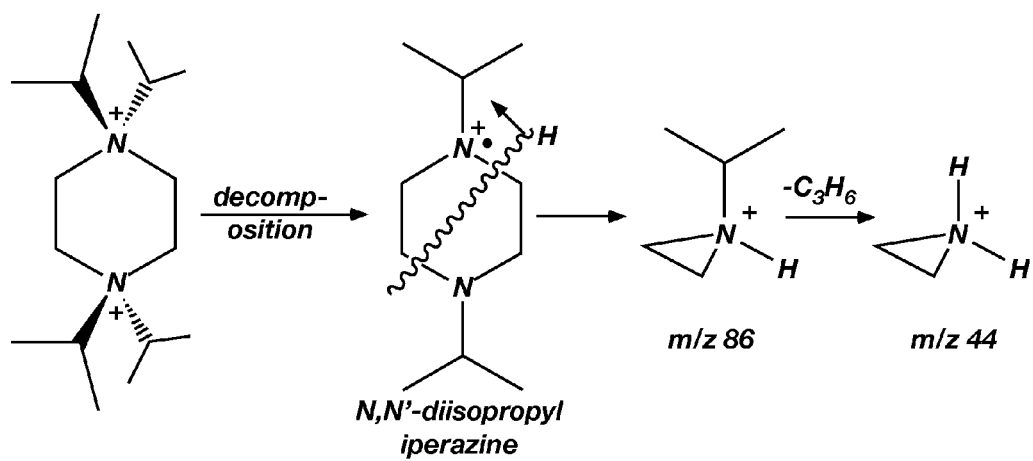
FIG. 34 shows a schematic diagram for the formation of ions at m/z 86 and m/z 44 from slow-eluting compounds related to DESH.

Referring back to FIG. 30C, the m/z 86 ion profile shows that it is not associated with m/z 114, and instead arises from a compound eluting about 0.4 minute later and at about 27.5 minutes. FIG. 33 is a mass spectrum of compound eluting at a RT of about 27.5 minutes. While not wishing to be bound by any particular theory, it is believed that the m/z 86 ion structure is that of the protonated isopropylaziridinium cation, that may be formed from further reaction of the amine moiety of the DESH precursor. For example, in solution the ethyl diisopropylamine moiety is known to dimerize forming the N,N, N',N'-tetraisopropyl piperazine dication, and decomposition of this compound may well produce N,N'-diisopropyl piperazine that may be expected to fragment by forming the isopropylaziridinium cation. FIG. 34 provides a scheme for the formation of ions at m/z 86 and m/z 44 from slow-eluting compounds related to DESH, which, while not wishing to be bound by any particular theory, are believed to be piperazine derivatives that are collected by the vacuum extractor device.

The devices and methods of the present disclosure enable efficient sampling of fixed surfaces contaminated with chemical compounds, such as CAS compounds. Fast and efficient sampling coupled with TD/GC/MS analysis is expected to provide the forensics community with a tool that may provide chemical evidence from an exposed environment, whether or not actual samples may be easily collected for transport back to the laboratory.

Example 5

In the following examples, mixtures of chemical compounds in microgram quantities were applied to painted wallboard, and sampled using the field vacuum extraction device 400 described with respect to FIGS. 4A through 4C (i.e., f-PVE) using a polydimethyl-siloxane-based SPME as the sorbent material 406. Subsequent TD/GC/MS analysis of the exposed SPME showed recovery of alkyl phosphites, alkyl phosphates, and even the acidic methyl phosphonic acid, which was surprising because acidic methyl phosphonic acid is well known as a problematic analyte because of its high surface reactivity. Further experiments were successfully conducted on samples that had been exposed to acidic phosphonates and phosphoryl halides.

FIGS. 35A through 35C and 36 demonstrate that sulfides and their hydrolysates are recoverable from a surface using the field vacuum extraction device 400 described with respect to FIGS. 4A through 4C. 2-Chloroethyl ethyl sulfide (CEES, which is a surrogate compound for the chemical warfare agent mustard), and a hydrolysate of CEES (i.e., methoxyethylethyl sulfide (MeOEES)) were applied to a surface of a glass sample. The surface of the glass sample was sampled using the field vacuum extraction device 400 and the SPME was analyzed using TD/GC/MS analysis. The results of the TD/GC/MS analysis obtained from the polydimethyl-siloxane-based SPME are shown in FIGS. 35A through 35C. As shown in FIG. 36, CEES and MeOEES and were recovered from the glass using the field vacuum extraction device 400.

Figure 37:
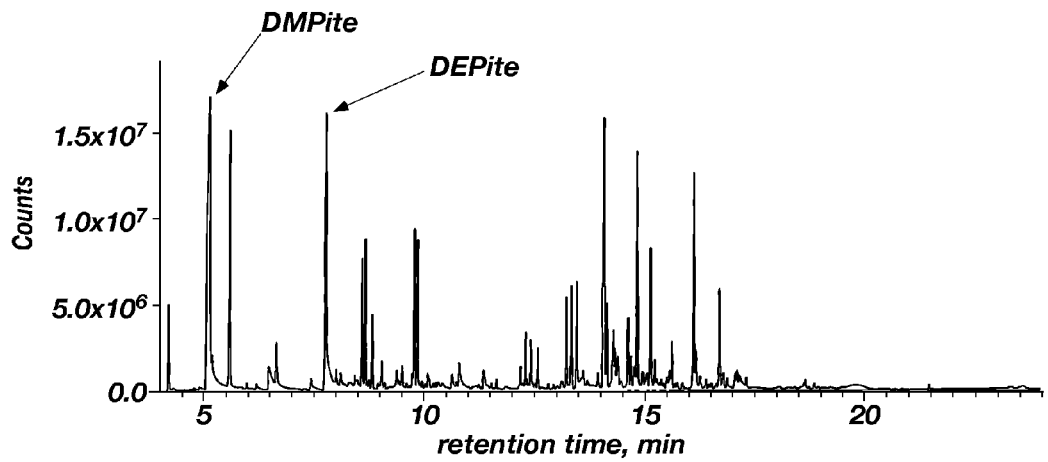
FIG. 37 shows TD/GC/MS profiles of an alkyl phosphite mixture collected from glass using a device according to an embodiment of the present disclosure (plastic syringe body).
Figure 38:
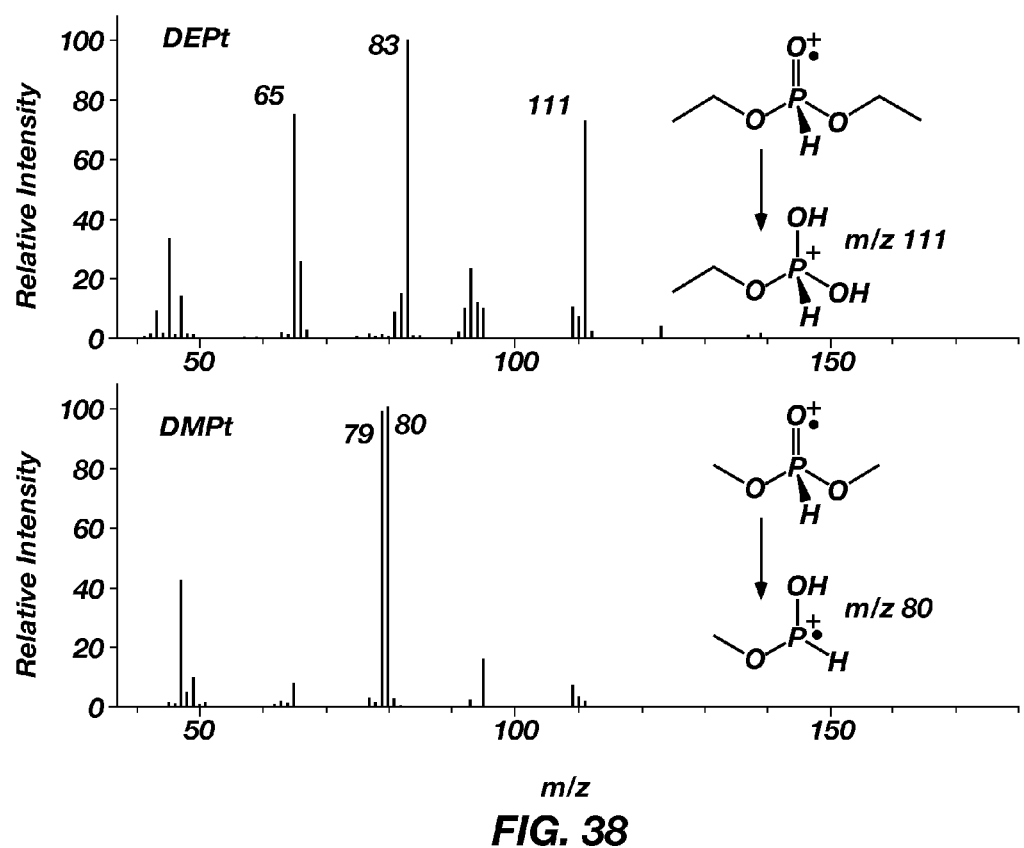
FIG. 38 shows a mass spectrum of DMPt, and DEPt, corresponding to the peaks shown in FIG. 37.

FIGS. 37 and 38 demonstrate that phosphoryl derivatives are recoverable from a surface using the field vacuum extraction device 400 described with respect to FIGS. 4A through 4C. A mixture of alkyl phosphites was applied to a surface of a glass sample. The surface of the glass sample was sampled using the field vacuum extraction device 400 and the SPME was analyzed using TD/GC/MS analysis. The results of the TD/GC/MS analysis obtained from the polydimethyl-siloxane-based SPME are shown in FIGS. 37 and 38. Dimethyl phosphite (DMPt or DMPite) and diethyl phosphite (DEPt or DEPite) were recovered from the glass using the field vacuum extraction device 400 as were chemical compounds believed to be derived from the surface and possibly from polymer materials of the field vacuum extraction device 400, such as those forming the chamber 408 or the seal 410. The high number of counts shown in FIG. 37 demonstrates that even small quantities of phosphoryl derivatives, such as phosphites, are recoverable using the field vacuum extraction device 400.

Figure 39:
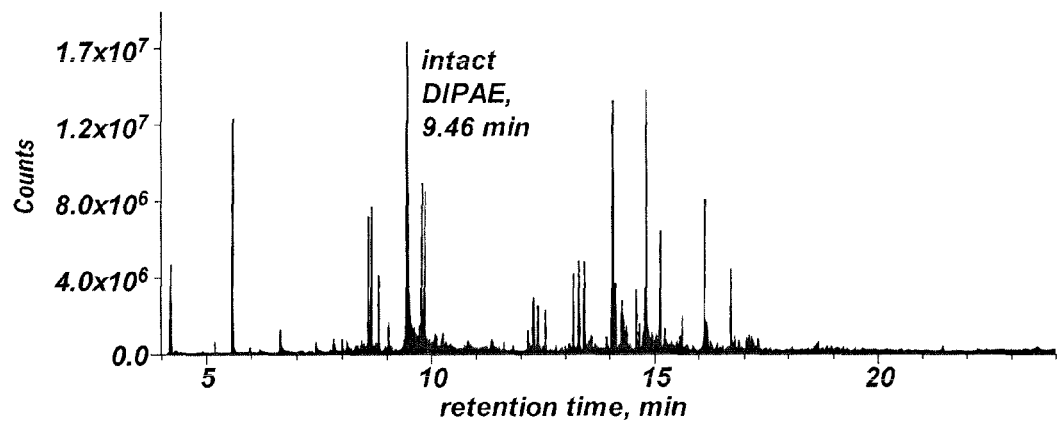
FIG. 39 shows TD/GC/MS profiles of diisopropylaminoethanol (DIPAE) collected from a glass surface using a device according to an embodiment of the present disclosure (plastic syringe body).
Figure 40:
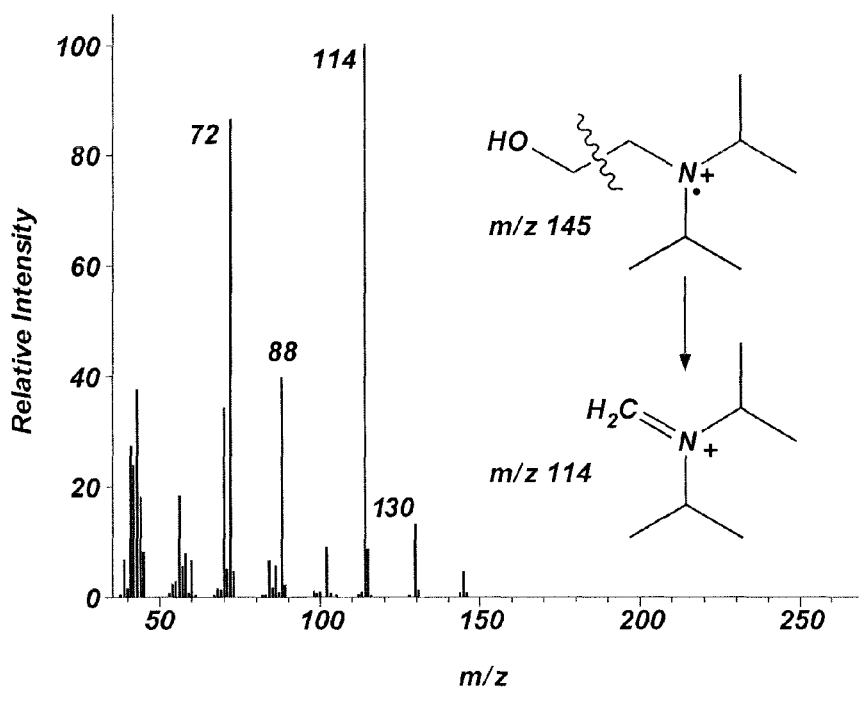
FIG. 40 shows a mass spectrum of DIPAE acquired from the peak shown in FIG. 39.

FIGS. 39 and 40 demonstrate that amines are recoverable from a surface using the field vacuum extraction device 400 described with respect to FIGS. 4A through 4C. Diisopropylaminoethanol (DIPAE) derived from VX degradation and synthesis was applied to a surface of a glass sample. The surface of the glass sample was sampled using the field vacuum extraction device 400 and the SPME was analyzed using GC analysis. The results of the TD/GC/MS analysis obtained from the polydimethyl-siloxane-based SPME are shown in FIGS. 39 and 40 and show that DIPAE was efficiently recovered from the glass using the field vacuum extraction device 400. These results were surprising since DIPAE strongly adsorbs to surfaces and, thus, impedes recovery from the surfaces using conventional methods.

Figure 41:
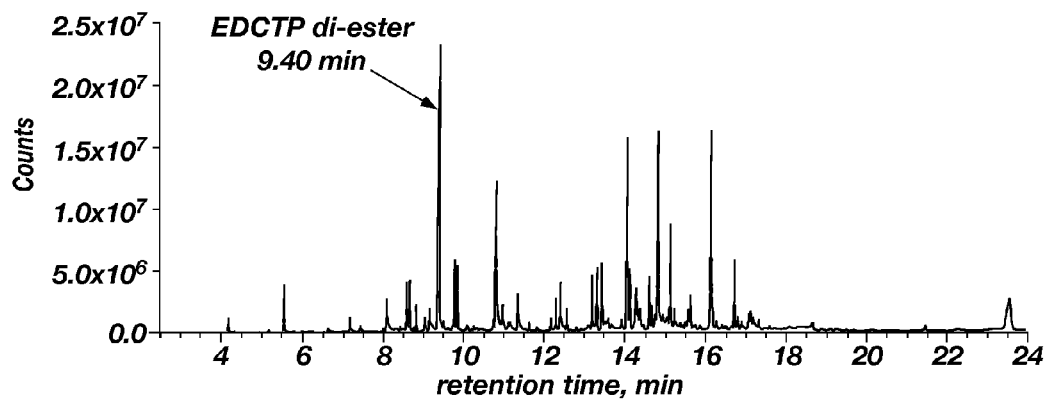
FIG. 41 shows TD/GC/MS profiles of compounds collected from a surface exposed to a solution of ethyldichlorothiophosphate using a device according to an embodiment of the present disclosure (plastic syringe body).
Figure 42:
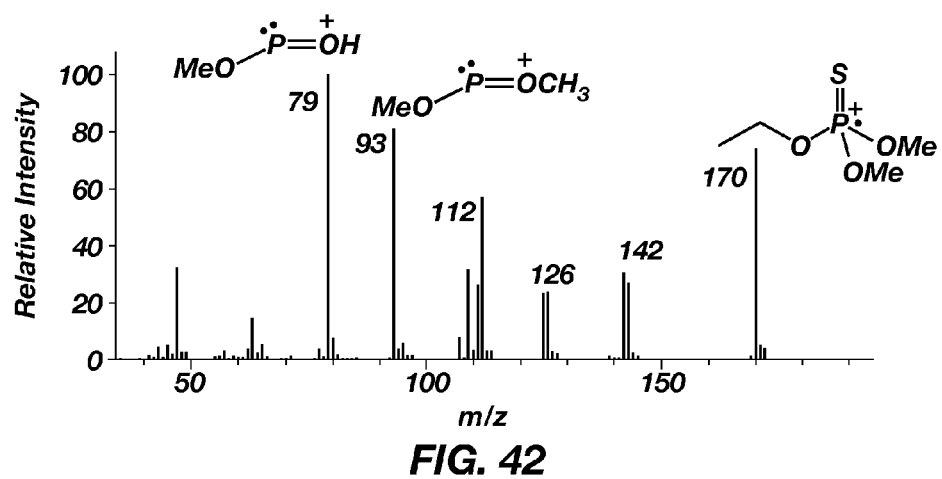
FIG. 42 shows a mass spectrum of compounds acquired from the peak shown in FIG. 41.

FIGS. 41 and 42 demonstrate that derivatives of ethyl dichlorothiophosphate that are formed in situ are recoverable from a surface using the field vacuum extraction device 400 described with respect to FIGS. 4A through 4C. Ethyl dichlorothiophosphate (EDCTP) may be hydrolyzed in the presence of a solvent to form esters. The surface of the glass sample was sampled using the field vacuum extraction device 400 and the SPME was analyzed using TD/GC/MS analysis. The results of the TD/GC/MS analysis obtained from the polydimethyl-siloxane-based SPME demonstrate that a di-ester of EDCTP was efficiently recovered from the glass using the field vacuum extraction device 400. A variety of thiophosphoryl derivatives was also recovered.

Figure 43:
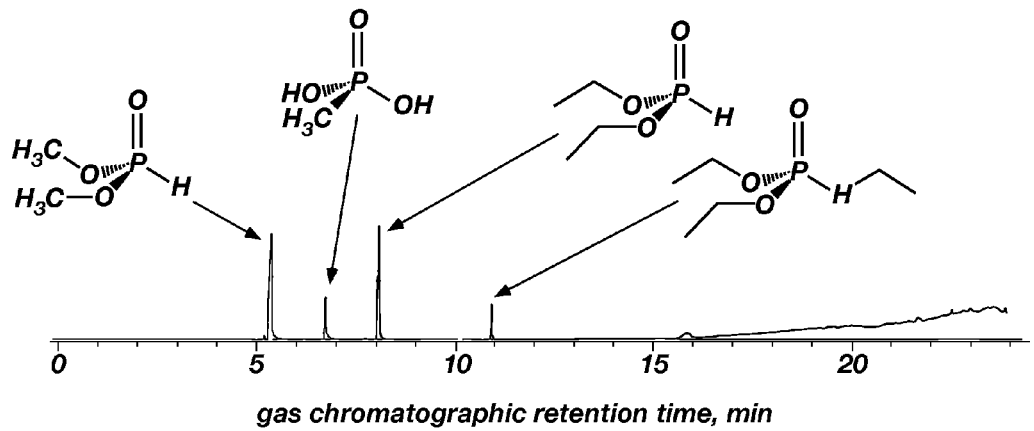
FIG. 43 is chromatographic trace produced by GC/MS analysis of an SPME sample exposed during sampling of a wallboard surface exposed to a phosphate-phosphite mixture using a device according to an embodiment of the present disclosure (plastic syringe body).

A mixture of CAS compounds in microgram quantities were applied to painted wallboard, and sampled using the FVE with a polydimethyl-siloxane-based SPME. The results of the TD/GC/MS analysis of the exposed SPME are shown in FIG. 43 and show recovery of alkyl phosphites and alkyl phosphates. The CAS compounds sampled are (from left to right) dimethyl phosphite, ethyl methyl phosphite, diethyl phosphite, and triethyl phosphate.

Figure 44:
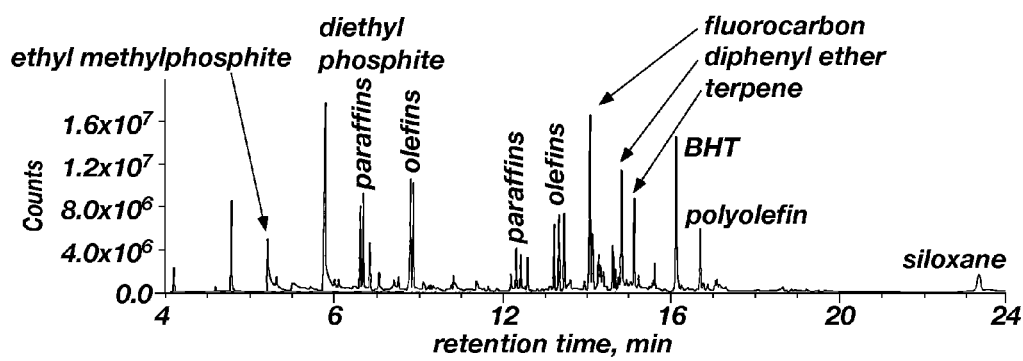
FIG. 44 is chromatogram of a sample pulled from glass exposed to diethyl phosphite using a device according to an embodiment of the present disclosure (plastic syringe body).

FIG. 44 demonstrates that the field vacuum extraction device 400 described with respect to FIGS. 4A through 4C will collect a wide array of organic compounds from the chemical environment. A sample was collected from glass exposed to a standard solution of diethyl phosphite applied in a solution with methanol. In addition to recovering this compound (eluting compounds from the chromatograph at a RT of about 7.8 minutes), a second derivative, ethyl methylphosphite was also recovered (eluting compounds from the chromatograph at a RT of about 5.4 minutes). A number of other compounds were also collected and then measured. Although each of these compounds has not been unequivocally identified, FIG. 44 demonstrates that the organic compounds collected are from several chemical families: paraffins (straight and branched), olefins (straight and branched), fluorocarbons, ethers, terpenes, butylated hydroxytoluene (BHT), and siloxanes.

Figure 45:
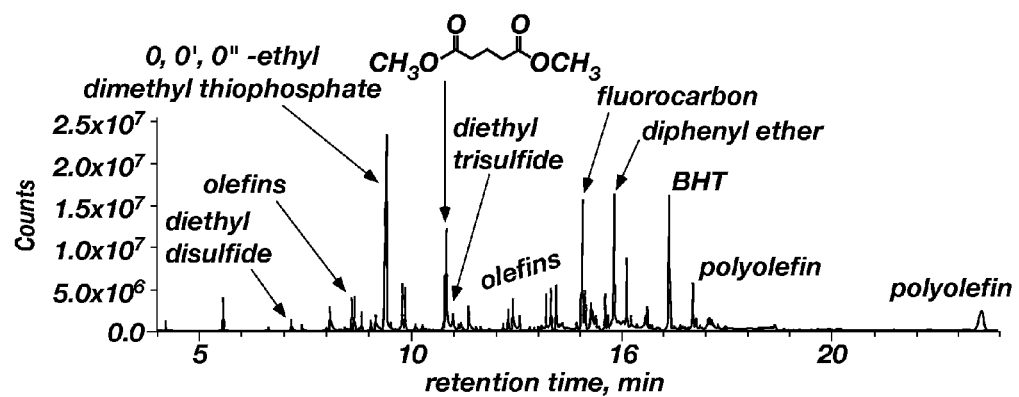
FIG. 45 is a chromatogram of a sample pulled from glass exposed to ethyldichlorothiophosphate using a device according to an embodiment of the present disclosure (plastic syringe body).

FIG. 45 demonstrates that the field vacuum extraction device 400 described with respect to FIGS. 4A through 4C may be used to characterize surfaces that have been exposed to compounds that are reactive or strongly surface adsorptive. FIG. 45 shows a chromatogram generated from a sample collected from glass exposed to O-ethyldichlorothiophosphate using the field vacuum extraction device 400 described with respect to FIGS. 4A through 4C, and displays a strong peak corresponding to the methylated ester, which was formed from a reaction of the dichloride with solvent on the surface. In addition, distinctive peaks corresponding to diethyl disulfide and diethyl trisulfide are measured. These compounds enable identification of the original exposure mixture.

Example 6

This example involved application of small amounts of CAS compounds to surfaces that were then sampled using the field vacuum extraction device 400 described with respect to FIGS. 4A through 4C, which included SPME fibers as the sorbent material. The SPME fibers were analyzed using TD/GC/MS. Compounds were selected in order to mimic as closely as possible those having forensic value, either because they are used in synthesis, typical synthetic byproducts, or degradation products. Standard solutions were generated for the test compounds by mixing them with methanol to a concentration of about 10 µg/µl. Dissolution using methanol resulted in partial hydrolysis of several of the compounds, which complicated the quantitative interpretation of the experiments, but enriched the compound diversity and provided a better mimic of what occurs when an impure CWA is released. Compounds that were formed by hydrolysis reactions are described herein.

Glass was used as a fixed surface as this material is of significant forensic value and because its surface could be effectively cleaned, thereby removing background from the subsequent GC/MS analyses that were performed. This latter consideration is important because it simplified the analyses and subsequent interpretations, easing identification of signature compounds, impurities, and degradation products. Additional experiments used painted wallboard or paper as the fixed surface.

Figure 46:
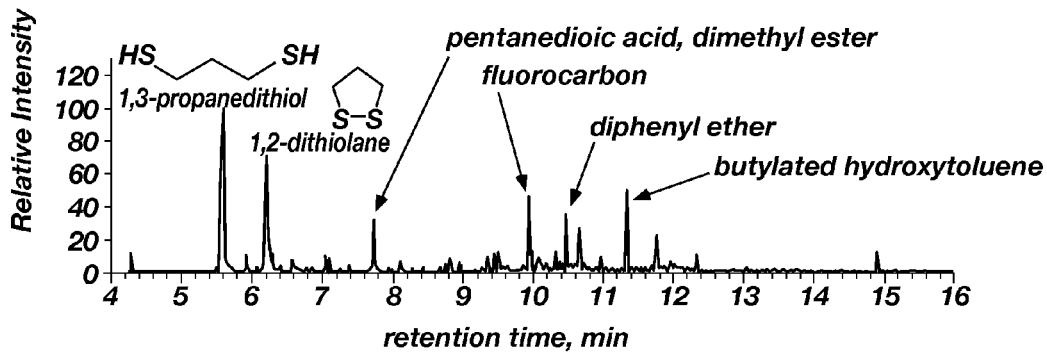

FIG. 46 is a TD/GC/MS obtained from sampling glass exposed to 1,3-propanedithiol (PDT) using the field vacuum extraction device 400. PDT was used as a surrogate for mercaptan degradation products, and the standard contained both PDT and dithiolane. The sulfhydryl functional groups of PDT have the potential for strong binding to surfaces, and thus the compound poses a sampling challenge. Dithiolane may result from intramolecular oxidative coupling and is also of interest because it provides a simple disulfide compound for evaluation. PDT was applied as a methanolic solution to a glass surface and then sampled using the field vacuum extraction device 400. Efficient collection of PDT and dithiolane from glass was demonstrated by the chromatogram resulting from the analysis of the SPME fiber. The mass spectrum of the compound eluting at about 5.6 minutes corresponded to PDT, while the compound eluting at about 6.2 minutes was dithiolane. The intensity of the chromatographic signal for the PDT molecular ion was about $3.2 \times 10^6$ counts, and when compared to the background (about $10^3$ counts), suggests that the minimum detectable quantity and, hence, recovery may be on the order of 40 nanograms (ng) for this compound. The results demonstrate that smaller quantities could be recovered by optimizing collection and analysis methods.

The molecular ion for dithiolane (m/z 106) was present at an abundance of $5 \times 10^6$ counts, a value greater than that for the molecular ion for PDT, which did not reflect the relative concentrations in the standard solution: in the analysis of the standard, the ratio was $3.6 \times 10^6$ counts for 1,3-propanedithiol (m/z 108) to $1.6 \times 10^6$ for dithiolane (m/z 106). This indicates that the less adsorptive dithiolane may be collected, a result consistent with the likelihood that PDT is more strongly surface-bound compared to the dithiolane.

Figure 47:
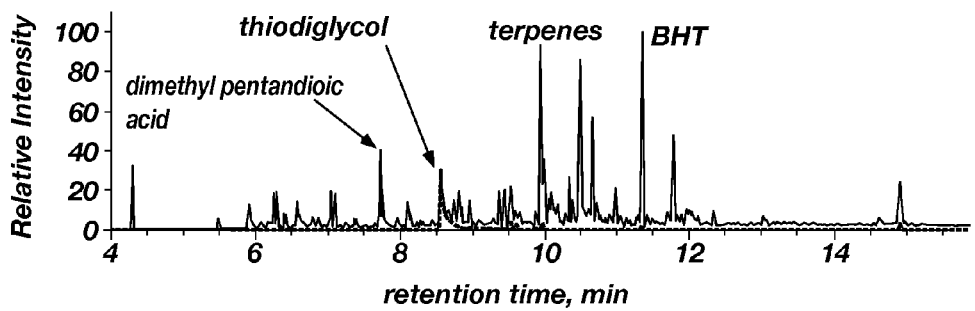

FIG. 47 is a TD/GC/MS of a sample obtained from glass exposed to 2,2'-thiodiethanol (thiodiglycol or TDG) using the field vacuum extraction device 400. The trace in the finer line is the total ion chromatogram and the trace in the thicker line is the m/z 61 single ion chromatogram. Sampling of glass exposed to the TDG solution produced a sample chromatogram with a tailing peak at about 8.6 minutes. Single ion chromatograms for the diagnostic mass spectrometric peaks at m/z 104 and m/z 61 were well above background, again suggesting that recovery of nanogram quantities is possible. Overall signal-to-noise was excellent, however, the results may indicate more aggressive surface binding by the hydroxyl groups of TDG compared to the sulfhydryl groups of PDT (FIG. 46). Other peaks in the chromatogram were derived from a variety of esters, terpenes and the plasticizer butylated hydroxytoluene (BHT).

Figure 48:
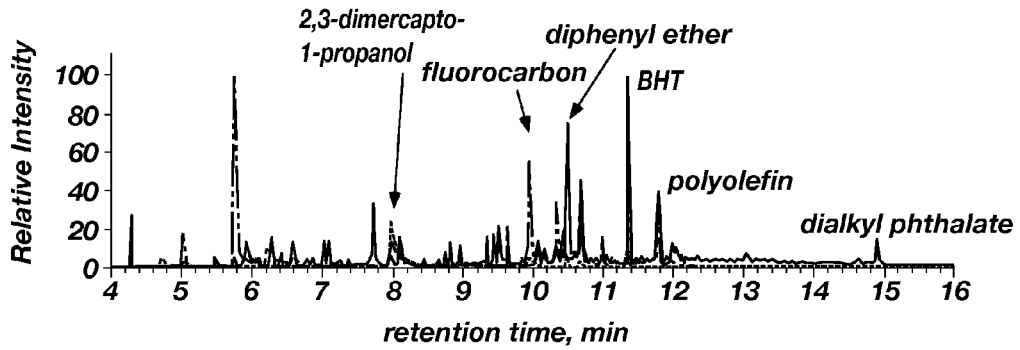

FIG. 48 provides results of sampling glass exposed to 2,3-dimercapto-1-propanol (DM-1-P) using the field vacuum extraction device 400. Analysis of the sample generated a complex sample chromatogram consisting of major peaks derived from terpenes, a few fluorocarbons, diphenyl ether, butylated hydroxytoluene and other indigenous "background" compounds. DM-1-P did not appear as an intense peak compared to the rest of the chemical background, but was readily identified on the basis of salient ions at m/z 106 and m/z 90 (losses of $H_2O$ and $H_2S$ from the molecular ion at m/z 124, respectively). These appear as tailing peaks at around 8 minutes. Trimercapto propane, an impurity originally observed in the analyses of the solution standard, was not observed.

Figure 49:
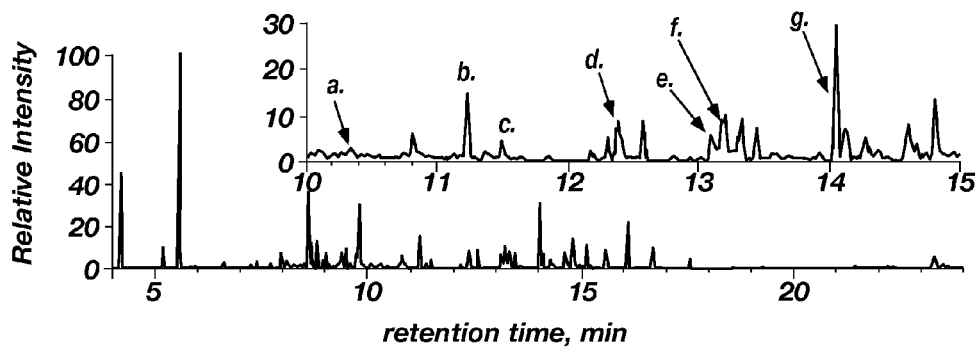

FIG. 49 provides results of sampling glass exposed to diethyl dithiophosphate (DEDTP) that presented multiple sampling challenges because the compound used for the standards contained significant impurities, and as a result the exposure resulted in delivery of multiple compounds. Hence, the chromatogram from the TD/GC/MS analysis of the sample obtained using the field vacuum extraction device 400 was complex. Seven different DEDTP-derived compounds were recovered by the PVE and identified on the basis of their mass spectra. The compounds are indicated in FIG. 49 as follows: (a) O,O'-diethyl-S-methyl thiophosphate, (b) O,O', O"-trimethyl thiophosphate, (c) O,O',S-trimethyl dithiophosphate, (d) DEDTP, (e) triethyl dithiophosphate isomer, (f) O,O'-diethyl-S-methyl dithiophosphate, and (g) O,O',S-triethyl dithiophosphate. The impurities arise from hydrolysis occurring either on in the standard compound, in the sample solution where methanol was used as a solvent, or on the surface. These reactions result in formation of higher ethyl and methyl derivatives, which are present in the standard solution along with DEDTP. Many of these compounds may also form in a CWA release environment, particularly if decontamination techniques were applied before sampling occurred since decontamination generally results in at least one of hydrolysis and oxidation.

Figure 50:
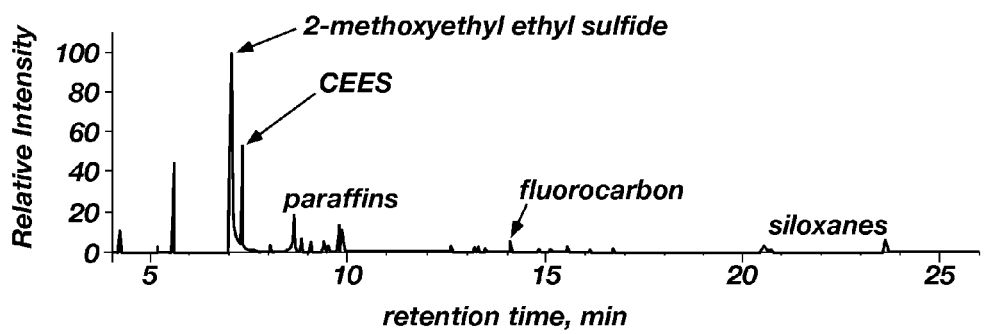

FIG. 50 is a TD/GC/MS analysis of sample obtained from glass exposed to a diethyl ethylphosphonate (DEEP) standard solution using the field vacuum extraction device 400. DEEP is both a synthetic byproduct (of VX manufacture) and a transesterification product. DEEP did not undergo hydrolysis. Because DEEP does not contain any hydroxyl or sulfhydryl functional groups, it probably does not adsorb as strongly to surfaces, which results in a sample chromatogram that is fairly uncomplicated with a very abundant peak derived from DEEP at about 10.1 minutes, as shown in FIG. 50. The quantitation ion for DEEP (m/z 111, derived from serial losses of $C_2H_3$ and $C_2H_4$ from the molecular ion at m/z 166) has an abundance of nearly $3\times10^6$, with a typical background of $1\times10^3$.

Figure 51:
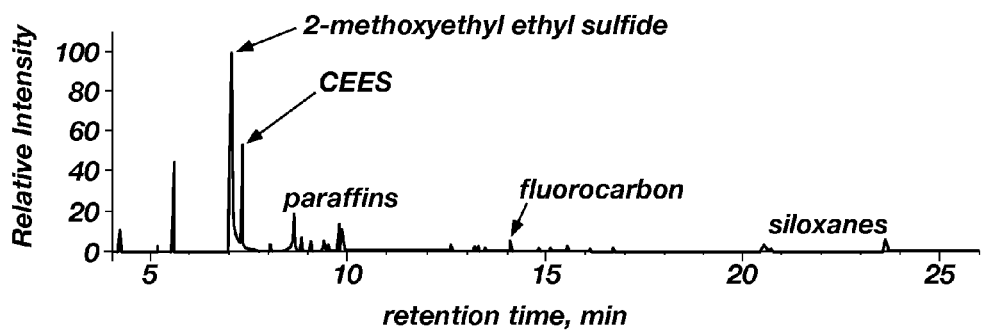

FIG. 51 is a TD/GC/MS analysis of sample obtained from glass exposed to a 2-chloroethyl ethyl sulfide (CEES) standard solution using the field vacuum extraction device 400. CEES was included in the array of test compounds because it is a surrogate for intact bis(2-chloroethyl)sulfide (H). The standard contained not only CEES, but also methoxyethyl ethyl sulfide, which was formed as a result of methanolysis occurring in the standard solution, and both compounds were identified in abundance in the chromatogram generated from the analysis of the PVE sample. The signature mass spectrometric ion upon which minimum detection would be made is m/z 75 for both compounds (corresponding to $[C_2H_5S=CH_2]^+$), and was about $10^4$ times greater than background. Given that the exposure quantity here was about 20 mg of each compound, the signal-to-noise ratio demonstrates that collection and detection of about 2 nanograms (ng) may be achieved using the field vacuum extraction device 400.

Figure 52:
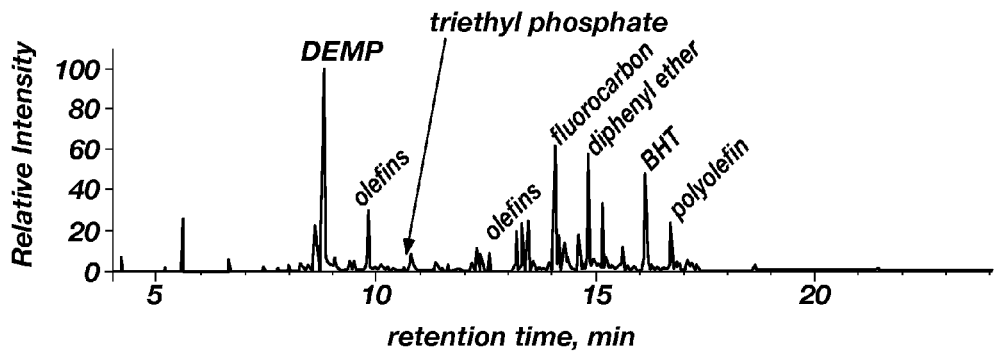

FIG. 52 is a TD/GC/MS analysis of sample obtained from glass exposed to a diethyl methylphosphonate (DEMP) solution using the field vacuum extraction device 400. Like DEEP, Diethyl methylphosphonate (DEMP) is both a synthetic byproduct and hydrolysis product of VX manufacture and release. It does not undergo appreciable hydrolysis, and is not as strongly surface active as hydroxyl or sulfhydryl compounds, and hence it is efficiently recovered from surfaces using the PVE. The TD/GC/MS chromatogram of the PVE SPME sample is fairly simple, with a dominant compound eluting at about 8.8 minutes having a mass spectrum corresponding to DEMP.

The quantitation ion at m/z 125 (loss of $C_2H_3$ from the DEMP molecular ion) has a signal-to-noise in excess of $10^4$, suggesting detection of quantities in the low nanogram range is possible with the PVE-analysis approach used here. It is worthwhile noting that triethylphosphate was also detected eluting at 10.6 min; this compound was a trace impurity in the DEMP standard solution.

Figure 53:
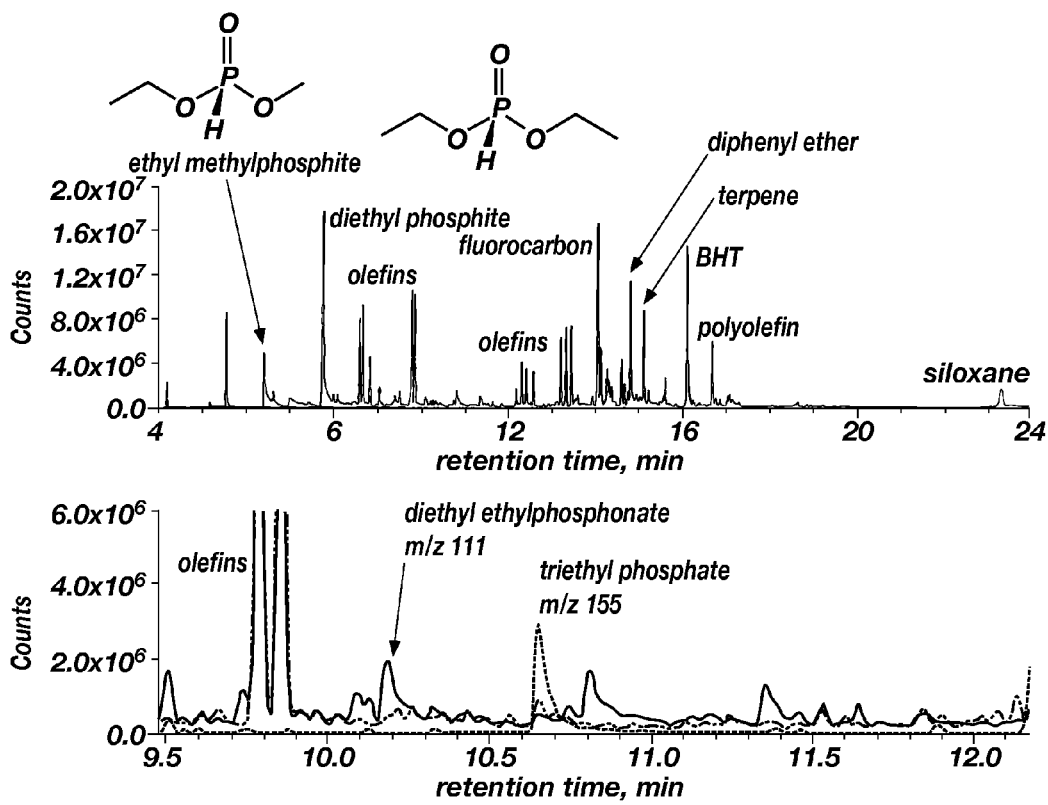

FIG. 53 is the chromatographic output of the TD/GC/MS analysis of sample obtained from glass exposed to an diethyl phosphite (DEPite) using the field vacuum extraction device 400. The top chromatogram is a total ion chromatogram and the bottom chromatogram includes a total ion chromatogram and a single ion chromatogram for m/z 155 expanded one hundred times and a single ion chromatogram for m/z 111 expanded one hundred times. The diethyl phosphite (DEPite) standard solution contained a significant quantity of ethyl methyl phosphite (EMPite), and traces of diethyl ethyl phosphonate (DEEP) and triethylphosphate (TEP). Both the DEPite and EMPite were readily recovered using the field vacuum extraction device 400, and detected in the TD/GC/MS chromatogram eluting at about 7.8 minutes and about 6.4 minutes, respectively (FIG. 53, top). Abundances of the quantitation ions suggested recovery/detection limits in the tens of nanograms range may be readily achievable. Both the TEP and DEEP were also detected well above background (FIG. 53, bottom). The detection of DEMP is significant because it was present in the standard at a concentration about 0.005 times the DEPite concentration, which implies that the quantity of these compounds deposited on the glass was on the order of 80 ng. The DEMP quantitation ion signal was about twenty times background. Detection of this quantity was consistent with detection limit estimates based on a signal-to-noise ration of the major compounds, and suggests that the latter estimates are overestimates.

Figure 54:
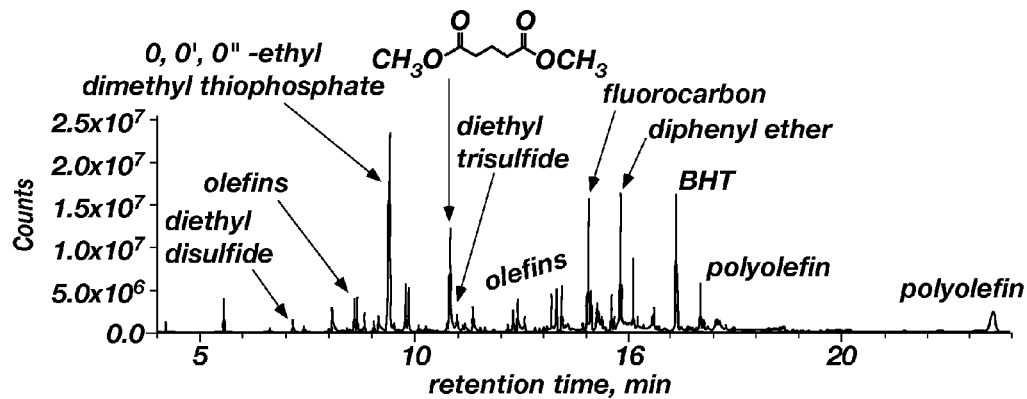

FIG. 54 is a TD/GC/MS analysis of sample obtained from glass exposed to an O-ethyl dichlorothiophosphate (EDCTP) solution using the field vacuum extraction device 400. An abundant peak corresponding to O,O',O"-ethyl dimethylthiophosphate eluted at 9.4 minutes. This ester was produced by methanolysis of the dichloride in the standard solution. Two other minor peaks were also observed, diethyl disulfide eluting at about 7.2 minutes, and diethyl trisulfide eluting at about 10 minutes. These compounds are the result of oxidative coupling of ethyl mercaptan, a degradation product of ethyl dichlorodithiophosphate. Of interest are compounds that were present in the standard solution, but were not sampled from the glass. Because the EDCTP is a reactive compound, several additional compounds were present, viz., EDCTP itself, O,O'-ethyl, methyl chlorothiophosphate, and O,O'-diethyl chlorothiophosphate. While not wishing to be bound by theory, the chloro compounds may have reacted with the glass surface, forming a non-extractable adduct, or may have completely hydrolyzed in the methanol solvent, forming acids that may not volatilize, or go through the GC column.

Figure 55:
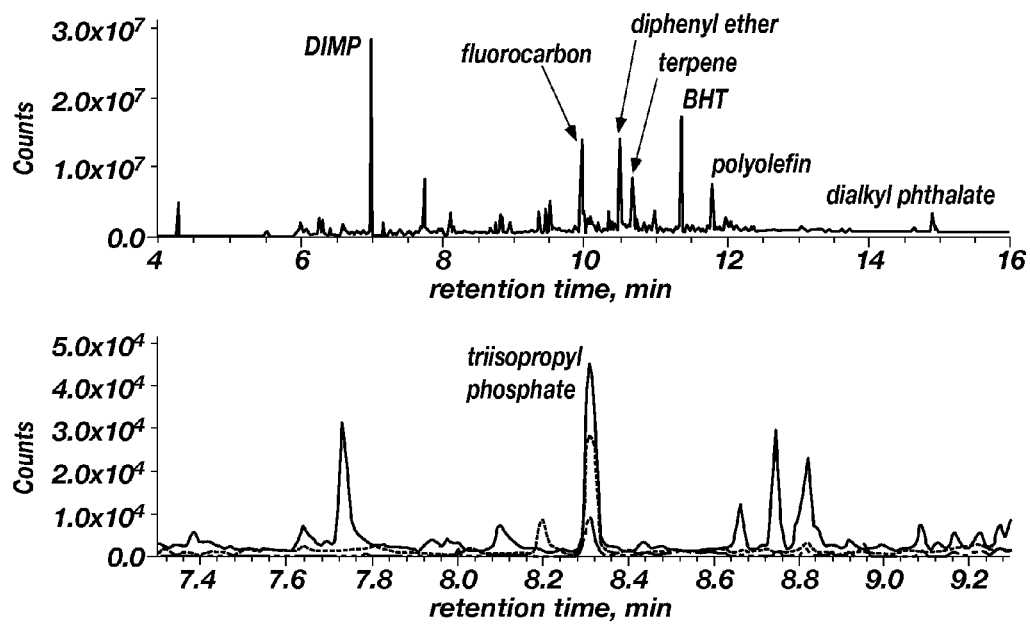

FIG. 55 is a TD/GC/MS analysis of sample obtained from glass exposed to 40 μg of diisopropyl methylphosphonate (DIMP) using the field vacuum extraction device 400, which eluted at about 7 minutes. In addition, a trace impurity in the DIMP standard solution, triisopropyl phosphate (TIP) was also picked up, and clearly identified at about 8.32 minutes. The fraction of the standard that was TIP was on the order of $2\times10^{-3}$, suggesting that about 80 ng was initially present on the glass. The signal-to-noise ratio of the salient ions is on the order of 20, indicating that collection and measurement of quantities in the low nanogram range should be possible.

Figure 56:
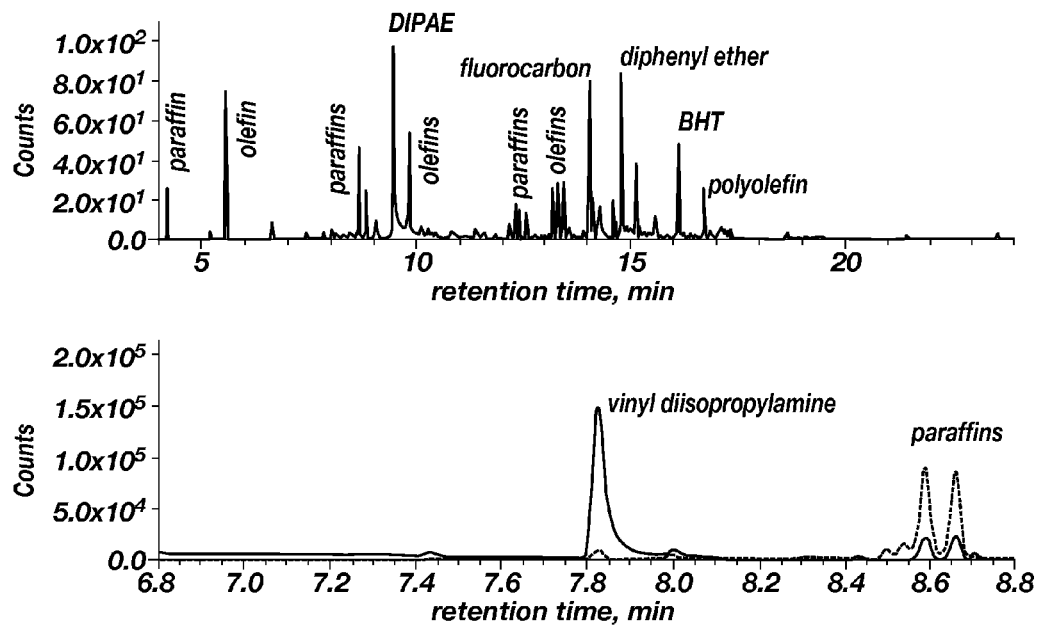

FIG. 56 is a TD/GC/MS analysis of sample obtained from glass exposed to diisopropylaminoethanol (DIPAE) using the field vacuum extraction device 400. The DIPAE standard solution produced a TD/GC/MS analysis with the target compound eluting at about 9.46 minutes. DIPAE is a hydrolysis product of VX, and may also form from VX hydrolysis. Hence, it is an important CAS compound. The abundance of the peak suggests that detection into the low nanogram range should be readily achievable. In addition, an earlier eluting peak displayed a mass spectrum consistent with vinyl diisopropylamine, and while this was barely noticeable in the total ion chromatogram, it was readily apparent using the target ion at m/z 86 (corresponding to an ion composition of [(i-Pr)(vinyl)NH$_2$]$^+$). Recovery of a small trace of impurity validates the efficacy of the field vacuum extraction device 400 for sampling CAS compounds.

Figure 57:
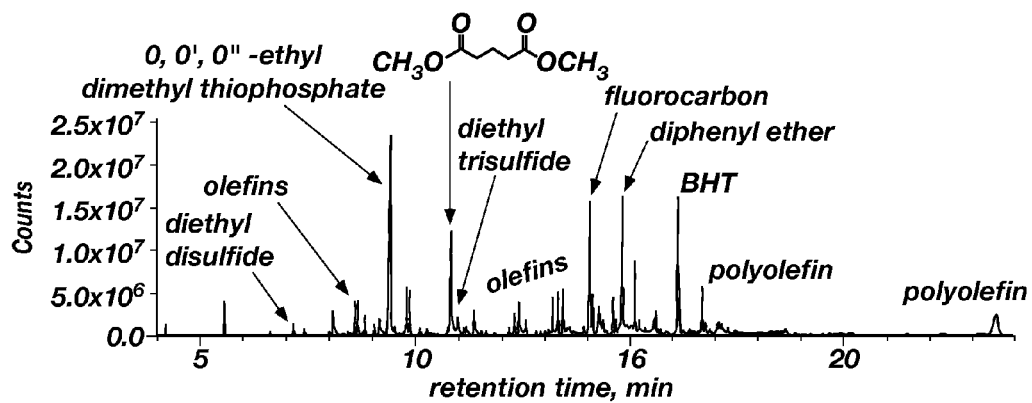

FIG. 57 is a TD/GC/MS analysis of sample obtained from glass exposed to O-ethyl dichlorothiophosphate (EDCTP) solution using the field vacuum extraction device 400. Analysis of the sample produced an abundant peak corresponding to O,O',O''-ethyl dimethylthiophosphate, eluting at 9.4 minutes. This ester was produced by methanolysis of the dichloride in the standard solution. Two other minor peaks were also observed, diethyl disulfide eluting at about 7.2 minutes, and diethyl trisulfide eluting at about 10 minutes. These compounds are the result of oxidative coupling of ethyl mercaptan, a degradation product of ethyl dichlorodithiophosphate. Of interest are compounds that were present in the standard solution, but were not sampled from the glass. Because the EDCTP is a reactive compound, several additional compounds were present, viz., EDCTP itself, O,O'-ethyl, methyl chlorothiophosphate, and O,O'-diethyl chlorothiophosphate. The chloro compounds may have reacted with the glass surface, forming a non-extractable adduct, or may have completely hydrolyzed in the methanol solvent, forming acids that may not volatilize, or go through the GC column.

Figure 58:
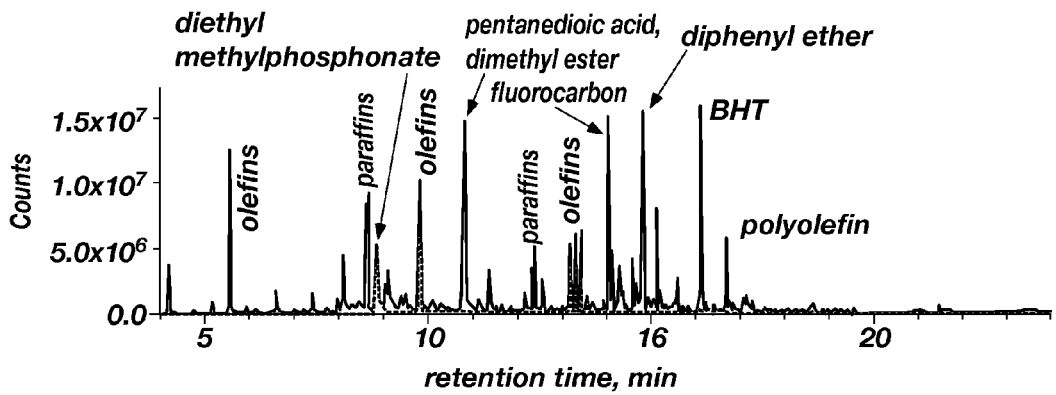

FIG. 58 is a TD/GC/MS analysis of sample obtained from glass exposed to ethyl methylphosphonic acid (EMPA) using the field vacuum extraction device 400. The intact acid is not sampled, however, the ethyl derivative diethyl methylphosphonate (DEMP) is formed in situ, and is effectively sampled using the FVE device. A rich background of organics is also collected from the surface.

Figure 59:
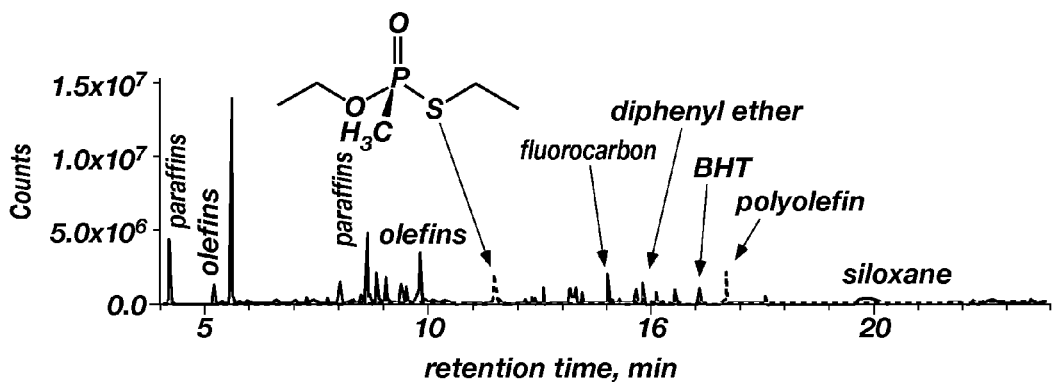

FIG. 59 is a TD/GC/MS analysis of sample obtained from glass exposed to ethyl methylphosphonothioic acid (EMPTA) using the field vacuum extraction device 400. The intact acid was not recovered, but the ethyl ester O,S-diethyl methylphosphonothioate was detected at ~11.45 min.

Figure 60:
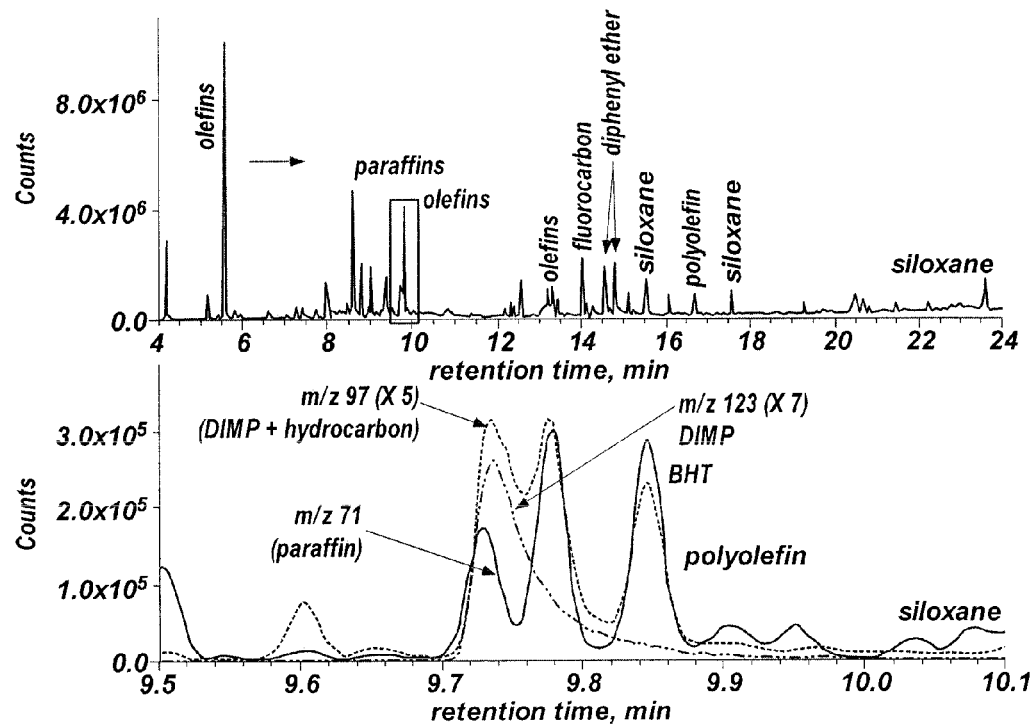

The top trace in FIG. 60 is a total ion chromatogram, acquired from a surface exposed to IMPA. IMPA is another hydrolysis product of GB, and hence represents an important class of CAS compounds. Being a reactive compound, intact IMPA was not detected in the experiment. However, the isopropyl derivative diisopropyl methylphosphonate (DIMP) was detected. DIMP co-eluted with olefin compounds (RT of about 9.7 min, highlighted by a surrounding box in FIG. 60, top). The olefin compounds eluting at about 9.7 minutes are expanded in the bottom trace. Specifically, the bottom traces in FIGS. 61A and 61B are single ion chromatograms for m/z 71 chromatogram (olefin-derived), for m/z 123 (from DIMP), and for m/z 97 (from DIMP).

Figure 61A:
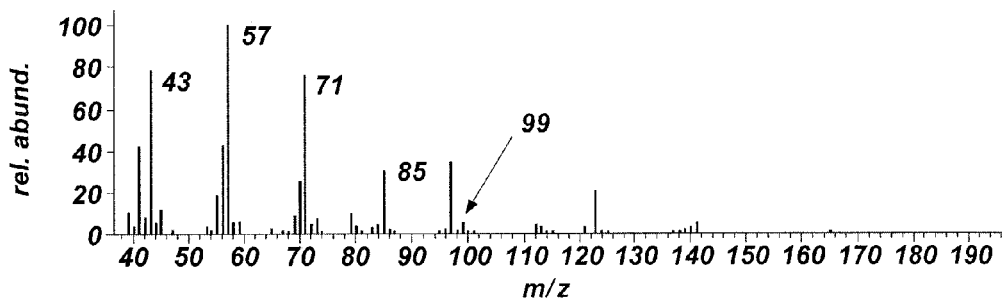
Figure 61B:
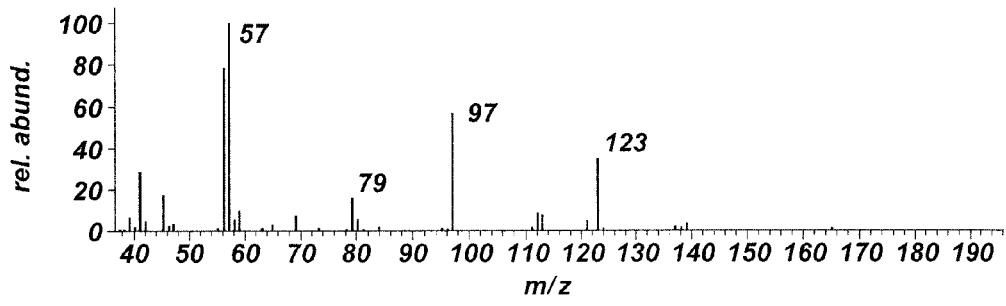

The mass spectrum of the olefin/paraffin background of FIG. 61A was clearly not consistent with that of DIMP. However, the deconvoluted spectrum that deconvoluted at retention time of about 9.74 minutes was explicitly diagnostic for DIMP (FIG. 61B).

Figure 62:
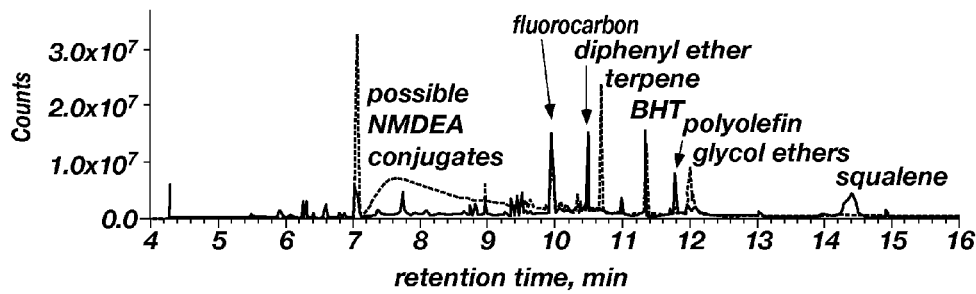
Figure 63:
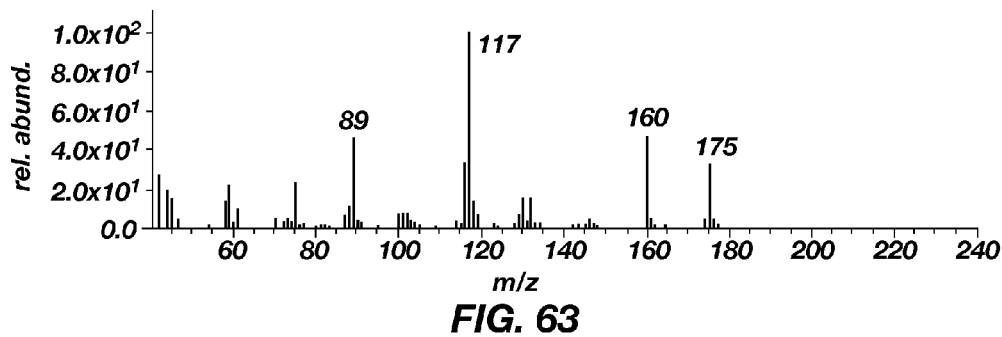

FIG. 62 is a TD/GC/MS analysis of sample obtained from glass exposed to an N-methyl diethanolamine (NMDEA) standard solution using the field vacuum extraction device 400. The solid line is the total ion chromatogram and the dashed line is m/z 117 (hypothesized to be from NMDEA stationary phase conjugates) expanded×100. The GC/MS analysis of the NMDEA standard solution did not produce a chromatographic peak with a corresponding mass spectrum that could readily be interpreted in terms of NMDEA. The compound has a molecular weight of 119, but no molecular ion at this m/z value or corresponding to the protonated form at m/z 120 was observed. The protonated form may eliminate H$_2$O to form an ion at m/z 102, while the radical cation should eliminate a CH$_2$OH radical to form m/z 88. No significant fragment ions were observed at these masses. Instead, the chromatogram of the standard solution exhibited a broad peak with a maximum at about 12 minutes, and tailing off for several minutes thereafter. FIG. 63 is a mass spectrum that arose from this broadened peak, which contained abundant ions at m/z 175, 160, 117 and 89. While not wishing to be bound by any particular theory, is thought to be reaction of NMDEA with the column stationary phase, which may explain the broadened appearance of this peak. The recovery of the conjugate shows that while the detection signature was perturbed by the TD/GC/MS analysis, it was nevertheless indicative of recovery of NMDEA.

In the TD/GC/MS analysis shown in FIG. 62, a normal paraffin-olefin background is present, along with the broadened peak that had been observed in the analysis of the NMDEA standard solution. The mass spectrum shown in FIG. 63 was very similar to that acquired in the standard analysis, and was characterized by an abundant m/z 117. Plotting the m/z 117 ion chromatogram highlights the broadened elution, and also shows a sharp peak eluting at about 7.05 minutes. This result is interpreted in terms of the PVE volatilizing and absorbing the NMDEA, after which it is transferred to the GC/MS, where it reacts with the stationary phase as it goes through the column.

Figure 64:
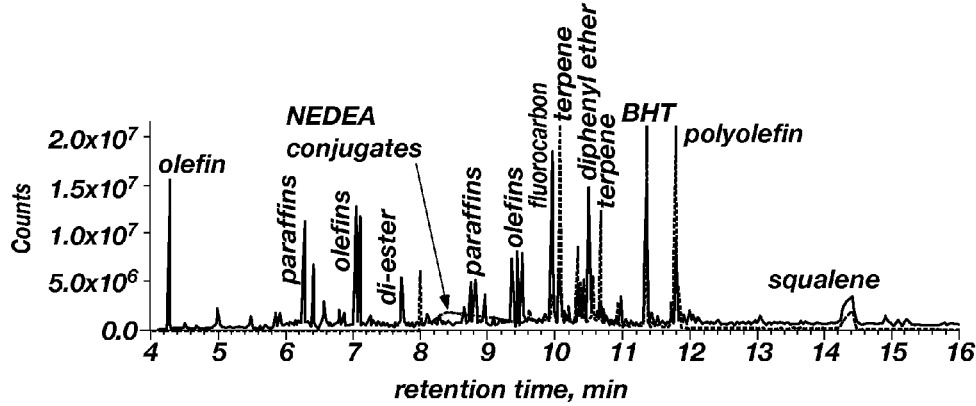
Figure 65:
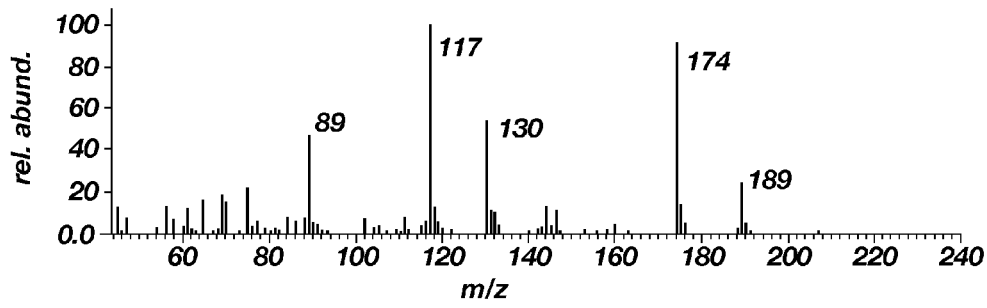

FIG. 64 is a TD/GC/MS analysis of glass exposed to an N-ethyl diethanolamine (NEDEA) standard solution obtained using the field vacuum extraction device 400. The GC/MS analysis of the NEDEA standard solution displayed behavior very similar to that seen for the NMDEA analyses, i.e., a sharp chromatographic peak with a mass spectrum that corresponded to NEDEA was not generated. The compound has a molecular weight of 133, but no molecular ion at this m/z value or corresponding to the protonated form at m/z 134 was observed. The protonated may eliminate H$_2$O to form an ion at m/z 116, while the radical cation should eliminate either a CH$_3$ radical or a CH$_2$OH radical to form either m/z 118 or m/z 102. No significant fragment ions were observed at these masses. Instead, the chromatogram of the standard solution exhibited a broad peak with maximum at about 11.8 minutes, and tailing off for several minutes thereafter. FIG. 65 is a mass spectrum that arose from this broadened peak contained abundant ions at m/z 189, 174, 130, 117, and 89. Ions at m/z 117 and m/z 89 were identical to those for NMDEA, the ions at m/z 189 and m/z 174 were also the same, only shifted higher in mass by 14μ, as expected for an ethyl-for-methyl substitution (the difference between NEDEA and NMDEA). This spectrum has not been unequivocally interpreted, but is thought to be due to the reaction of NMDEA with the column stationary phase, which may be consistent with the broadened appearance of this peak. The TD/GC/MS chromatogram generated by analysis of the sample obtained using the field vacuum extraction device 400 contained a broadened peak with the mass spectrum specified above, only eluting slightly later at about 8.5 minutes. While not wishing to be bound by any particular theory, is thought to be reaction of NEDEA with the column stationary phase, which may explain the broadened appearance of this peak.

Figure 66:
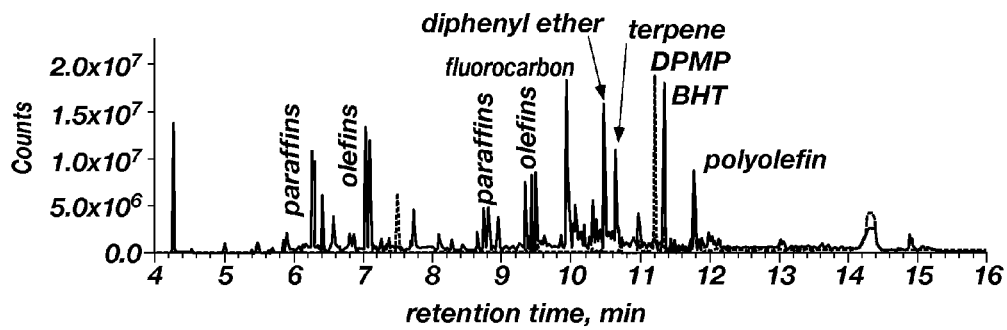

FIG. 66 is a TD/GC/MS analysis of sample obtained from glass exposed to pinacolyl methylphosphonic acid (PMPA) standard solution using the field vacuum extraction device 400. PMPA is the principal hydrolysis product of soman (GD) and, thus, is important as a CAS compound of interest. PMPA is a moderately strong acid of about pKa~3.3, which limits its volatility and serves to make the compound strongly sorptive to many surfaces. Thus, it is a difficult compound to recover from the environment, and generally does not go through a GC. Analysis of the 10 μg/μl standard solution confirmed this expectation, in that no PMPA was observed eluting from the column. However, the PMPA contained a low-level impurity, dipinacolyl methylphosphonate (DPMP), which eluted at 16 minutes in the analysis of the standard solution, and was characterized by a mass spectrum with abundant ions at m/z 124, 123 and 97. These are signature ions for DPMP in the analysis of the PVE sample. The TD/GC/MS analysis of the sample from exposed glass revealed a low abundance peak eluting at about 11.97 minutes. When the m/z 123 signature ion was plotted, which clearly identified this chromatographic peak as a possibility for DPMP, and the mass spectrum confirmed the assignment. Other peaks in the chromatogram were typical of normal background for the field vacuum extraction device 400 and TD/GC/MS sampling and analysis combination.

Figure 67:
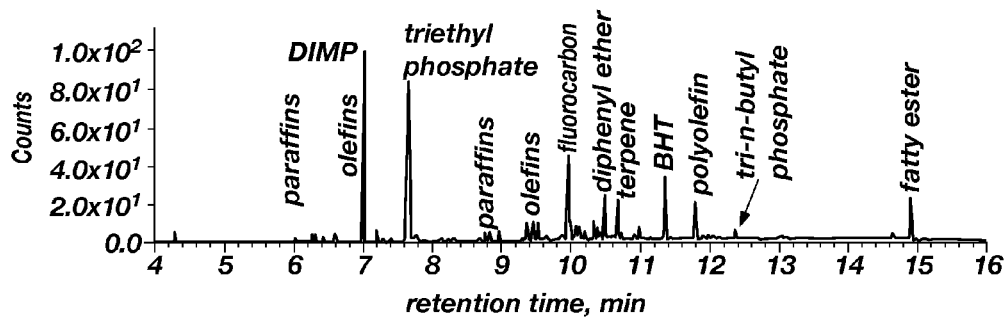

FIG. 67 is a TD/GC/MS analysis of a sample obtained from glass exposed to a standard solution of triethyl phosphate (TEP) and DIMP using the field vacuum extraction device 400. The TEP solution was co-spiked with DIMP to evaluate detectability for both compounds in the same experiment. FIG. 67 displays prominent peaks for both compounds, DIMP eluting at about 7.0 minutes, and TEP eluting at about 7.6 minutes. TEP and DIMP were detected with high signal-to-noise levels, and hence the field vacuum extraction device 400 is expected to be able to recover low concentrations. In addition, two other phosphoryl compounds were detected, the first eluting at about 8.32 minutes whose mass spectrum was consistent with that of an organophosphate derivative. The second compound was tri-n-butyl phosphate, eluting at about 12.34 minutes. The detection demonstrates the ability of the field vacuum extraction device 400 to recover trace impurities from fixed surfaces.

Figure 68:
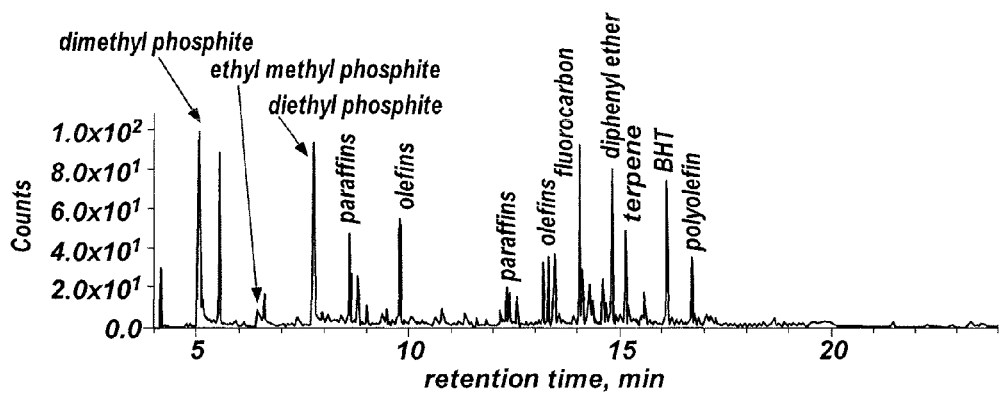
Figure 69A:
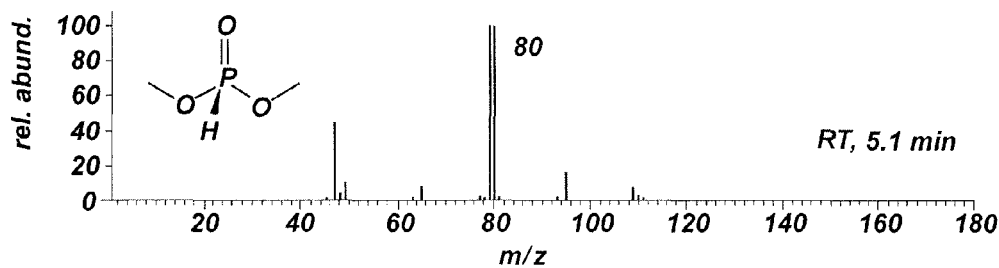
Figure 69B:
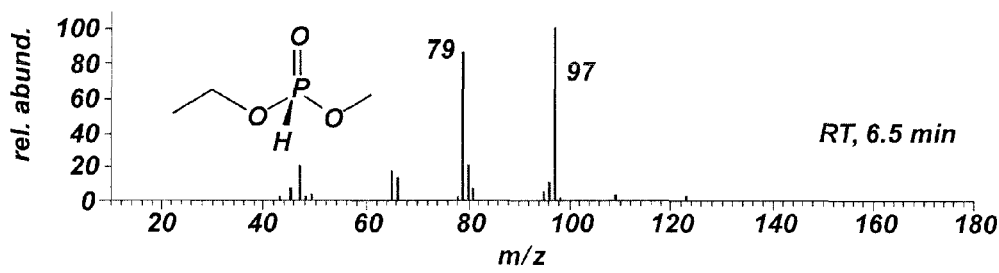
Figure 69C:
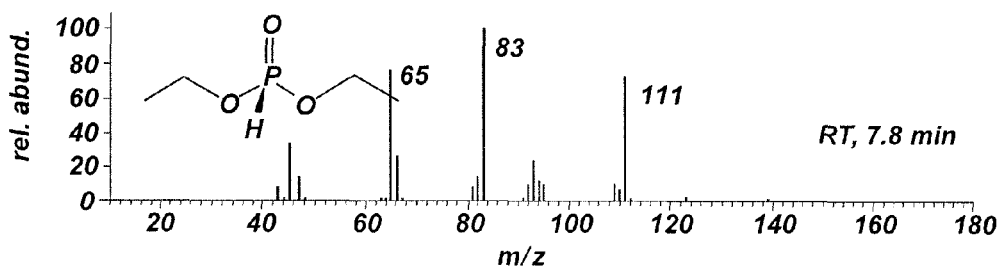

FIG. 68 is a TD/GC/MS analysis of a sample obtained from glass exposed to a standard solution of triethylphosphite (TEPite) and DIMP using the field vacuum extraction device 400. Analysis of a PVE sample of glass exposed to a standard solution of TEPite did not result in detection of the target compound. Instead, the TD/GC/MS chromatogram contained abundant peaks corresponding to diethyl phosphite (DEPite) and dimethyl phosphite (DMPite) at retention times of about 7.8 minutes and about 5.1 minutes, respectively. In addition, a smaller peak was observed at about 6.4 minutes. FIGS. 69A through 69C contain mass spectra of the peaks observed at about 5.1 minutes, about 6.5 minutes and about 7.8 minutes. The mass spectra are consistent with a phosphoryl compound, and have been interpreted as ethyl methyl phosphite. The presence of the methyl and ethyl phosphite derivatives suggests that the methanol solvent may be hydrolyzing the ethoxy groups originally attached to TEPite. It is unlikely that the field vacuum extraction device 400 is causing the chemical modifications. This data indicates the ability of the field vacuum extraction device 400 to pick up trace contaminants.

Figure 70:
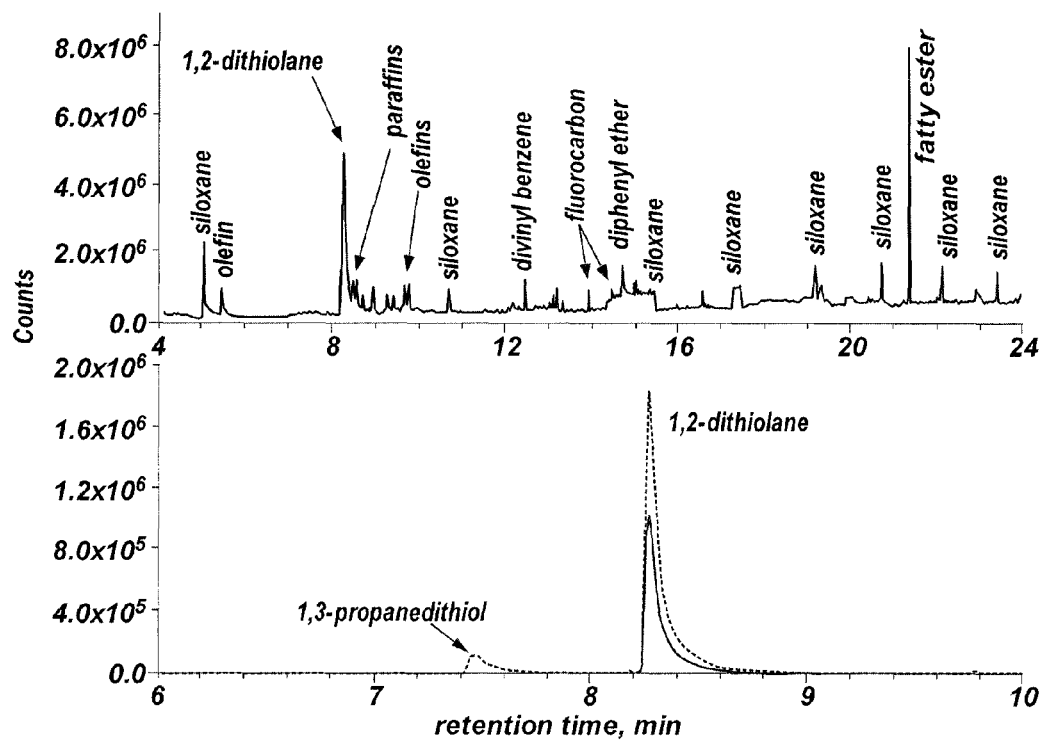

FIG. 70 is a TD/GC/MS analysis of a sample obtained from painted wallboard exposed to 1,3-propanedithiol (1,3-PDT) standard solution using the field vacuum extraction device 400. The top of FIG. 70 is a total ion chromatograph, which shows abundant 1,2-dithiolane peaks and significant siloxane peaks. The bottom of FIG. 70 includes single ion chromatographs; the solid line being m/z 106, the molecular ion for 1,2-dithiolane and the dashed line being m/z 108 expanded by twenty times, the molecular ion for 1,3-PDT. The TD/GC/MS analysis of the PVE sample of wallboard exposed to 1,3-PDT revealed a different envelope of compounds in the chemical background, typified by many more siloxane compounds, as well as olefins, paraffins, and divinyl benzene. The dominant signal from the standard solution was due to the compound eluting at about 8.3 minutes, which was assigned as 1,2-dithiolane, based on the mass spectrum. The 1,2-dithiolane compound was a significant impurity (about 16%) in the standard solution and, thus, was applied to the wallboard together with the 1,3-PDT. In addition, 1,3-PDT was detected, eluting slightly before the 1,2-dithiolane at about 7.5 minutes. It was not noticeable in the total ion chromatogram, but was distinguished by the single ion chromatogram for m/z 106. The mass spectrum generated for this peak was consistent with the compound assignment. The intensity of the 1,3-PDT chromatographic peak was significantly less than expected based on the analysis of the standard solution. Either the 1,3-PDT was oxidizing in the methanolic solution to produce the 1,2-dithiolane between the time of the standard analysis and the wallboard experiment, or the recovery was lower. In fact, recovery from glass suggested that the 1,2-dithiolane should account for about 40% of the total (up from 16% in the standard solution analyzed by direct injection). In the wallboard experiment, 1,2-dithiolane accounts for on the order of about 95% of the compound applied. Another explanation is that the 1,3-PDT is absorbing into the polymer more aggressively than is the 1,2-dithiolane, and hence is recovered and detected much less efficiently.

Figure 71A:
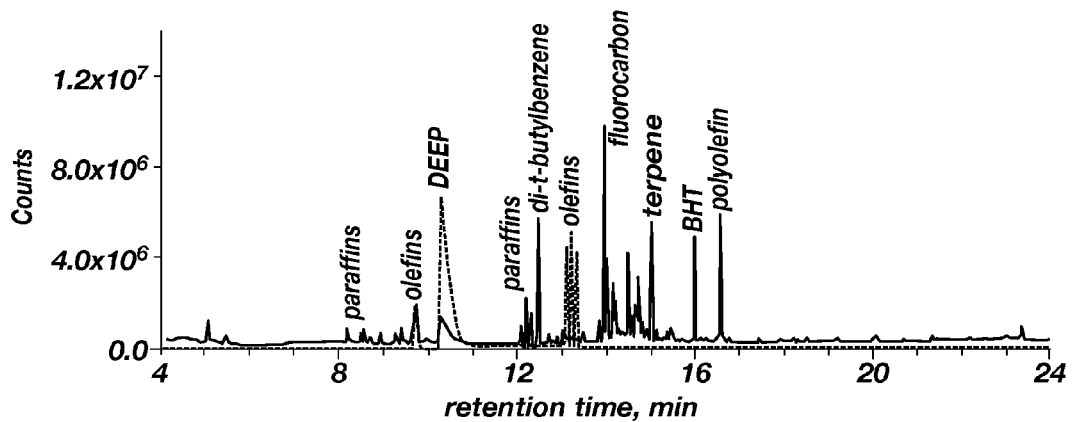
Figure 71B:
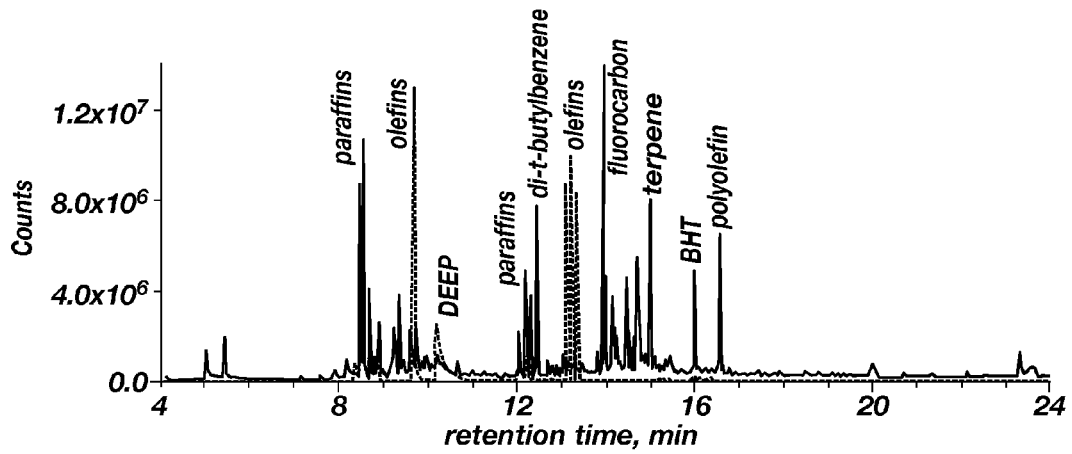

FIGS. 71A and 71B are TD/GC/MS analyses of a sample obtained from painted wallboard exposed to diethyl ethylphosphonate (DEEP) standard solution using the field vacuum extraction device 400. FIG. 71A includes a total ion chromatogram, with DEEP eluting at 10.3 minutes and a single ion chromatograph for m/z 111 (the principal fragment ion in the mass spectrum of DEEP), expanded by thirty times. FIG. 71B includes a TD/GC/MS analysis obtained from a sample collected using the field vacuum extraction device 400 about seven (7) days after exposure. The TD/GC/MS analysis samples collected from exposed wallboard samples showed that the PVE recovered significant DEEP from the exposed wallboard. DEEP elutes at about 10.3 minutes with a significant chromatographic tail, indicating that the compound is adhering to some part of the TD/GC/MS system. Wallboard exposed to DEEP was at sampled at different times since exposure ($\Delta t_{exp}$) to determine how quickly a compound may deplete after release. To do this, the intensity of the m/z 111 ion chromatographic peak (derived from DEEP) was compared at different $\Delta t_{exp}$ values. Exposed wallboard sampled after $\Delta t_{exp}$ at about seven (7) days produced a peak that was about 2.6 times lower than a sample with $\Delta t_{exp}$ at less than one (1) day. The lower recovery at longer $\Delta t_{exp}$ values was due either to diffusion into the bulk and also to volatilization. The result suggests that the matrix will function to preserve the compound, but that for many compounds, depletion is occurring as a function of time. In the DEEP/wallboard experiment, the depletion rate is estimated at about 0.14 day to about one (1) day, based on the depletion seen over the course of about seven (7) days, and assuming single exponential behavior.

Figure 72A:
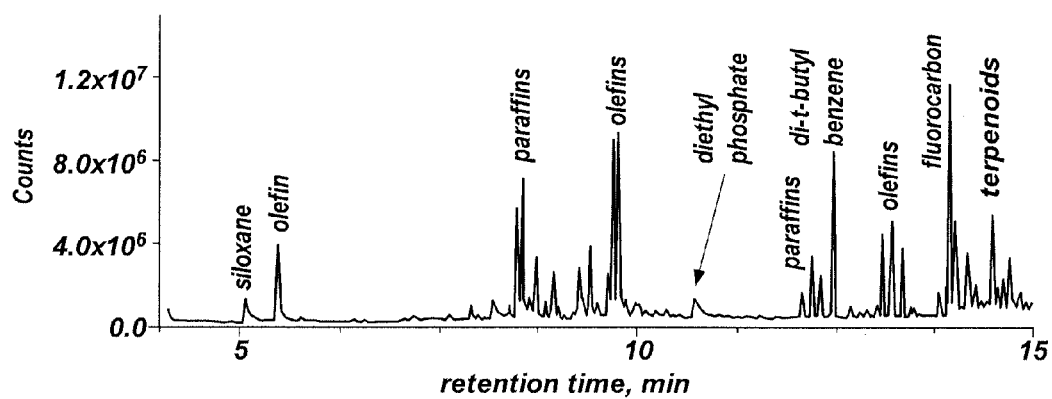
Figure 72B:
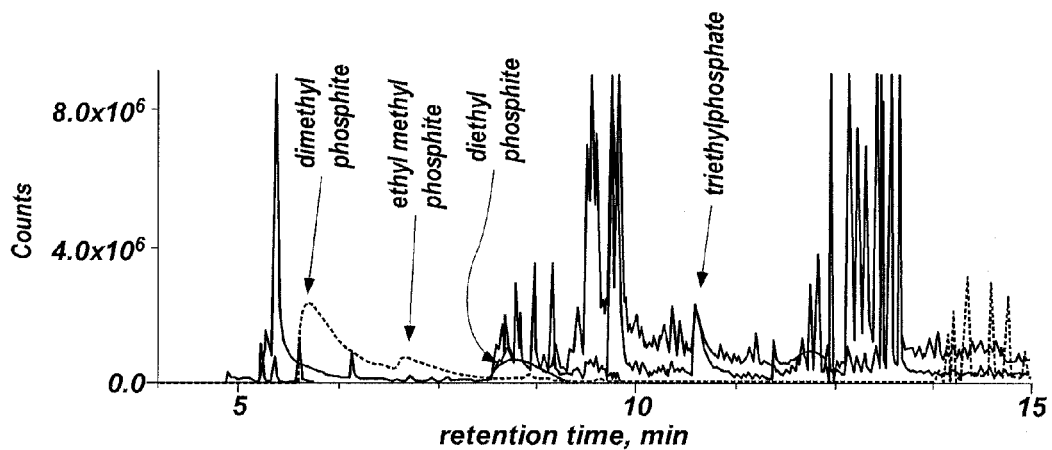

FIGS. 72A and 72B are TD/GC/MS analyses of a sample obtained from painted wallboard exposed to diethyl phosphite (DEPite) standard solution using the field vacuum extraction device 400. FIG. 72A is a total ion chromatogram. FIG. 72B is includes single ion chromatograms, expanded one hundred times for m/z 83, m/z 80, and m/z 111. Sampling of wallboard exposed to the diethylphosphite standard solution resulted in a TD/GC/MS chromatogram that contained the characteristic paraffins, olefins and siloxanes that typify the chemistry of the wallboard. The only phosphoryl-derived compound that overtly stands out in the total ion chromatogram corresponds to triethylphosphate at about 10.7 minutes, as indicated by its mass spectrum. Triethylphosphate is an impurity in the diethylphosphite standard solution. Careful inspection of the single ion chromatograms of m/z 80, m/z 83 and m/z 111 readily reveals the presence of three phosphite compounds. Both dimethylphosphite and ethyl methylphosphite display a prominent ion at m/z 80, and broadened peaks at about 5.9 minutes and about 7.1 minutes correspond to these two compounds, as indicated by the mass spectra measured at these retention times. Both of these compounds are derived from diethylphosphite as a result of hydrolysis and re-esterification with the methanol used as the solvent in the standard solutions. Diethylphosphite is also recovered by the PVE, but is identified only with more difficulty. Identification is based on the elevated baseline seen in both of the ion chromatograms of m/z 111 and m/z 83, which are diagnostic for diethylphosphite. They maximize at about 8.5 minutes. While identification was difficult in these experiments, it may be simplified by implementation of chromatography adapted for the alkylphosphites; this may sharpen the broadly eluting peaks, permitting easier chromatographic assignment and improved signal-to-noise in the mass spectra.

Figure 73A:
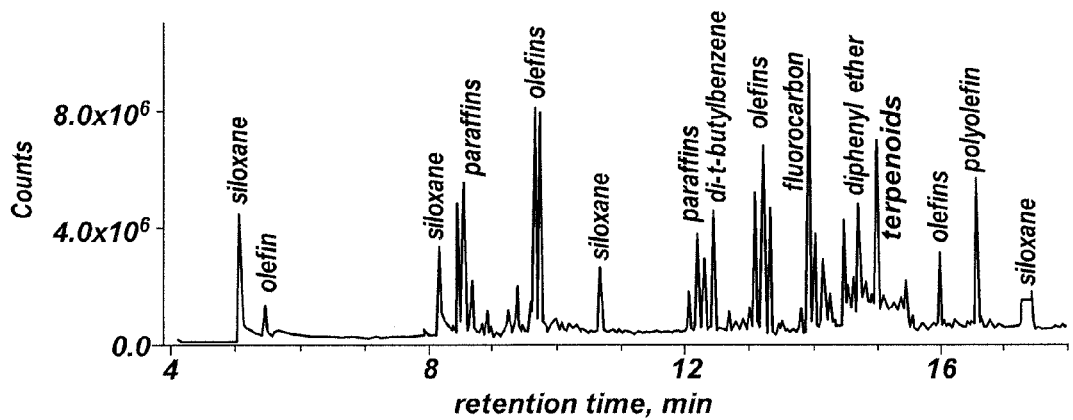
Figure 73B:
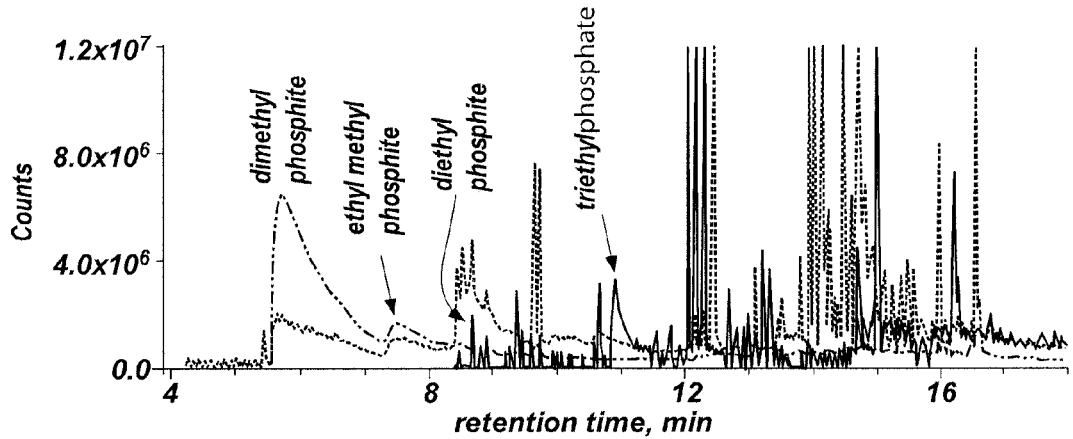

FIGS. 73A and 73B are TD/GC/MS analyses of samples obtained from painted wallboard exposed to triethylphosphite (TEPite) standard solution using the field vacuum extraction device 400. FIG. 73A is a total ion chromatogram. FIG. 73B includes single ion chromatograms for m/z 79 (expanded one hundred times) at m/z 65 (expanded four hundred times), and at m/z 155 (expanded eight hundred times). Four different phosphoryl-bearing compounds were collected using the field vacuum extraction device 400 on wallboard that was exposed to TEPite. None of the compounds were intact TEPite, but all were derived from it. Dimethylphosphite eluted at about 5.7 minutes and appeared as a broadened, tailing peak in the m/z 79 ion chromatogram (FIG. 73B). Ethyl methylphosphite displayed the same profile but eluted at 7.5 min in the m/z 79 chromatogram, which appears as a prominent fragment ion in the mass spectra of both compounds. Diethyl phosphite is also observed, eluting at about 8.5 minutes, with the same broadened profile. It is not defined by a unique single ion, but the compound may be identified by examining the chromatographic profiles of m/z 65, m/z 83 and m/z 111, which are all prominent in the mass spectrum of diethylphosphite. The elution behavior is illustrated by FIG. 73B; the spikes on the top of the broad peak are derived from co-eluting paraffins and siloxanes near this retention time. The fourth phosphoryl compound was triethylphosphate, which elutes at about 10.9 minutes. It cannot be observed in the total ion chromatogram, but is clearly seen in the m/z 155 ion chromatogram (FIG. 73B). As in the case of the phosphites, the compound is clearly recovered. Triethylphosphate is probably formed from oxidation of the TEPite, which is not present in the standard solution. Instead, it may react with either by hydrolysis, methanolysis, or by oxidation.

Figure 74:
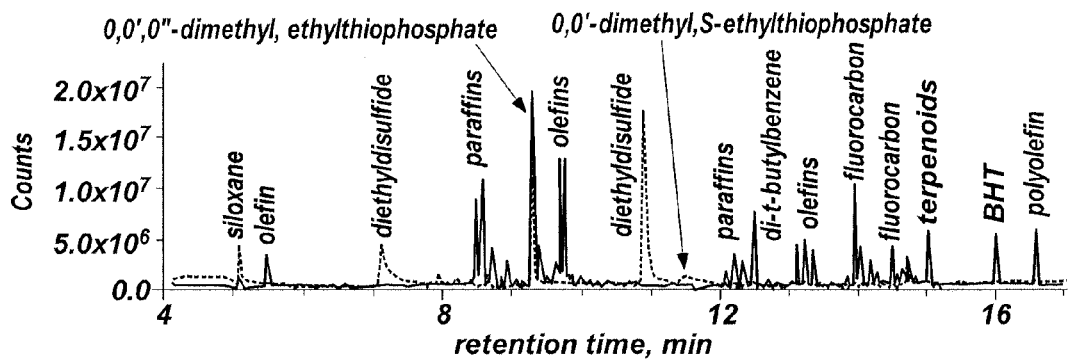

FIG. 74 is a TD/GC/MS analysis of a sample obtained from painted wallboard exposed to ethyl dichlorothiophosphate (EDCTP) standard solution. The analysis shows both a total ion chromatogram and a single ion chromatogram for m/z 61, expanded eight hundred times. Sampling of wallboard exposed to the EDCTP standard solution resulted in recovery of the methanolysis product O,O',O"-dimethyl, ethylthiophosphate eluting at about 9.3 minutes. Intact chlorothiophosphate derivatives did not survive the environment on the wallboard. While not wishing to be bound by any particular theory, the chloro derivatives may have undergone hydrolysis, forming O-ethylthiophosphoric acid, which strongly bound to surface reactive moieties. Another low abundance thiophosphate eluted at about 11.5 minutes, and had a mass spectrum consistent with O,O'-dimethyl,S-ethylthiophosphate. This compound was not observed in the analyses of the standard, and represents recovery of a very trace impurity by the field vacuum extraction device 400. The EDCTP standard solution also contained low levels of sulfides that were readily detected. Diethyldisulfide and diethyltrisulfide eluted at about 7.1 minutes and about 10.9 minutes, respectively. These compounds were readily identified on the basis of their mass spectra.

In the examples described herein, the primary CAS compound was recovered. Normal applications were in the microgram range; however, the response of the TD/GC/MS was generally greater than about $10^7$ counts. These robust analytical responses show that the field vacuum extraction device 400 may be used to recover quantities of chemical compounds in the low nanogram range, a conclusion supported by the detection of impurities and hydrolysis products.

The envelope of test compounds spanned a range of phosphoryl, sulfide, alcohol, and amine functional groups, which represent the majority of the chemistry that may be encountered in a CAS collection. With only a few exceptions, the compounds were efficiently recovered, which indicates that the field vacuum extraction device 400 may be effective for a broad range of chemical compounds.

Impurities and hydrolysis products collected using the field vacuum extraction device 400 shown in the examples described herein are indicative of compounds representative of impurities that may accompany a CWA release, and may constitute the CAS compounds that are desired when sampling fixed surfaces using the field vacuum extraction device 400. The impurities were present only at very low levels, with fractional abundances of perhaps less than or equal to 0.001, and yet were still readily recovered by the PVE suggesting that low nanogram quantities are recoverable.

Thus, the field vacuum extraction device 400 has been shown to be effective for collecting several classes of target compounds, including sulfides, amines, phosphines, phosphates, and phosphonates. These examples demonstrate that the field vacuum extraction device 400 is capable of collecting organic compounds as well as hydrolysis products indicative of chemistry occurring on the surfaces between the organic compounds and indigenous compounds in the surface environment. The efficacy of the field vacuum extraction device 400 is demonstrated by the experiments described herein, combined with the fact that the field vacuum extraction device 400 may be fabricated from off-the-shelf components and its operational simplicity. The device is small, inexpensive, easy-to-operate and effective for non-destructive sampling from fixed surfaces. The samples produced, viz., exposed SPME fibers, are amenable to analysis in a large number of laboratories, and, in addition, the syringe barrel and plunger seal are disposable, thereby eliminating carry-over concerns. Additionally, the recovered samples sorbed onto the SPME fibers may be stored for transport to laboratories or archival purposes.

The invention has been described herein in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A device for extracting at least one chemical compound from a surface, comprising:
    a chamber including an open end;
    a plunger slidably inserted from an end of the chamber opposite the open end and having a cavity extending therethrough, the plunger fitted within the chamber such that retraction thereof results in a decrease in pressure within the chamber;
    a sorbent material sized and configured to be inserted through the cavity in the plunger and into the chamber; and
    a seal structure positioned proximate the open end of the chamber for preventing air from entering the chamber through the open end of the chamber upon retraction of the plunger.

2. The device of claim 1, wherein the plunger further comprises a stopper material over at least one end of the cavity therethrough, the stopper material comprising a perforable material.

3. The device of claim 1, wherein the plunger comprises a polymer material or polytetrafluoroethylene.

4. The device of claim 1, wherein the sorbent material comprises at least one of a solid-phase microextraction fiber, activated carbon, and a synthetic zeolite.

5. The device of claim 4, wherein the solid-phase microextraction fiber comprises at least one of polydimethylsiloxane, polyacrylate, carboxen-polydimethylsiloxane, and polydimethylsiloxane-divinylbenzene.

6. The device of claim 1, wherein the sorbent material is sized and configured to be inserted through the cavity into the chamber.

7. The device of claim 1, wherein the plunger is fitted within the chamber such that retraction thereof creates a vacuum pressure within the chamber.

8. The device of claim 1, wherein the seal structure comprises a viscoelastic material.

9. A device for extracting at least one chemical compound from a surface, comprising:
    a collector having a sealing material affixed to an open end thereof;
    a vacuum chamber having a first end coupled to a vacuum source and a second end opposite the first end coupled to the collector;
    a sorbent material disposed within the vacuum chamber and extending through an aperture in the vacuum chamber; and
    an injector for inserting the sorbent material through the aperture in the vacuum chamber.

10. The device of claim 9, wherein the sealing material comprises at least one of a polymer material.

11. The device of claim 9, wherein the vacuum chamber comprises a chamber coupled with the vacuum source.

12. The device of claim 9, wherein the vacuum chamber comprises an evacuated chamber sealed by at least one valve.

13. The device of claim 12, wherein a pressure within the evacuated chamber is less than atmospheric pressure.

14. The device of claim 9, wherein the vacuum chamber comprises a first chamber disposed adjacent a second chamber and at least one valve disposed between the first chamber and the second chamber.

15. The device of claim 14, further comprising at least another valve disposed between the second chamber and the vacuum source.

16. The device of claim 9, wherein the sorbent material comprises at least one of a solid-phase microextraction fiber, activated carbon, and a synthetic zeolite.

17. A method of detecting at least one chemical compound, comprising:
    sealing a chamber to a surface having the at least one chemical compound thereon;
    decreasing pressure within the chamber to volatilize at least a portion of the at least one chemical compound;
    introducing a sorbent material to volatilized chemical compounds within the chamber; and
    analyzing the sorbent material to detect the at least one chemical compound.

18. The method of claim 17, wherein introducing a sorbent material to the volatilized chemical compound within the chamber comprises introducing at least one of a solid-phase microextraction fiber, activated carbon, and a synthetic zeolite to the volatilized chemical compound within the chamber.

19. The method of claim 18, wherein the solid-phase microextraction fiber comprises at least one of polydimethylsiloxane, polyacrylate, carboxen-polydimethylsiloxane, and polydimethylsiloxane-divinylbenzene.

20. The method of claim 17, wherein sealing a chamber to a surface having the at least one chemical compound thereon comprises pressing a sealing material disposed on a collector at one of end of the chamber to the surface, the sealing material comprising at least one of a polymer material and a viscoelastic material.

21. The method of claim 17, wherein decreasing pressure within the chamber to volatilize at least a portion of the at least one chemical compound comprises applying a vacuum pressure to the chamber such that the pressure over the surface within the chamber is decreased.

22. The method of claim 17, wherein introducing a sorbent material to volatilized chemical compounds within the chamber comprises introducing the sorbent material to at least one of a volatilized chemical warfare agent, a volatilized chemical attribution signature, and volatilized hydrolysis products thereof within the chamber.

23. The method of claim 17, wherein introducing a sorbent material to volatilized chemical compounds within the chamber comprises introducing the sorbent material to at least one of diisopropylaminoethane thiol, 2,3-dimercapto-1-propanol, 3-mercapto-1,2-propanediol, N-ethyl diethanol amine, N-methyl diethanolamine, 1,3-propanedithiol, dithiolane, 2,2'-thiodiethanol, diethyl dithiophosphate, diethyl methylphosphonate, diisopropyl methylphosphonate, dipinacolyl methylphosphonic acid, diethyl ethylphosphonate, diethyl phosphite, O-ethyl methylphosphonothioate, triethyl phosphite, 2-chloroethylethylsulfide, ethyl dichlorothiophosphate, esters of ethyl dichlorophosphate, 1,3-PDT, 2,2-tetrachlorodiphenylethane, N-methylethylenediamine, and hydrolysis products thereof within the chamber.

24. The method of claim 17, wherein analyzing the sorbent material to detect the at least one chemical compound comprises determining at least one of a synthetic route, stabilization, storage, and method of release of the at least one chemical compound.

25. A device for extracting at least one chemical compound from a surface, comprising:

a collector having a sealing material affixed to an open end thereof;

a vacuum chamber having a first end coupled to a vacuum source and a second end opposite the first end coupled to the collector, the vacuum chamber comprising an evacuated chamber sealed by at least one valve; and a sorbent material disposed within the vacuum chamber and extending through an aperture in the vacuum chamber.

26. A device for extracting at least one chemical compound from a surface, comprising:

a collector having a sealing material affixed to an open end thereof;

a vacuum chamber having a first end coupled to a vacuum source and a second end opposite the first end coupled to the collector, the vacuum chamber comprising a first chamber disposed adjacent a second chamber and at least one valve disposed between the first chamber and the second chamber; and a sorbent material disposed within the vacuum chamber and extending through an aperture in the vacuum chamber.

\* \* \* \* \*